United States Patent
Chen et al.

(10) Patent No.: US 6,303,793 B1
(45) Date of Patent: Oct. 16, 2001

(54) 4-ALKENYL-AND 4-ALKYNYLOXINDOLES

(75) Inventors: Yi Chen, Nutley; Apostolos Dermatakis, North Brunswick; Jin-Jun Liu, Warren; Kin-Chun Luk, North Caldwell, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/566,054

(22) Filed: May 5, 2000

Related U.S. Application Data

(62) Division of application No. 09/464,502, filed on Dec. 15, 1999, now Pat. No. 6,130,239.
(60) Provisional application No. 60/112,591, filed on Dec. 17, 1998, and provisional application No. 60/149,073, filed on Aug. 16, 1999.

(51) Int. Cl.[7] ......................... C07D 209/34; C07D 209/04
(52) U.S. Cl. ............................................. 548/486; 548/469
(58) Field of Search ....................... 548/486, 469

(56) References Cited

U.S. PATENT DOCUMENTS

| | | |
|---|---|---|
| 4,556,672 | 12/1985 | Kadin . |
| 5,086,186 | * 2/1992 | Kelly ..................................... 548/468 |
| 5,206,261 | 4/1993 | Kawaguchi et al. . |
| 5,322,950 | 6/1994 | Sircar et al. . |
| 5,374,652 | 12/1994 | Buzzetti et al. . |
| 5,397,787 | 3/1995 | Buzzetti et al. . |
| 5,409,949 | 4/1995 | Buzzetti et al. . |
| 5,488,057 | 1/1996 | Buzzetti et al. . |
| 5,576,330 | 11/1996 | Buzzetti et al. . |
| 5,792,783 | 8/1998 | Tang et al. . |
| 5,834,504 | 11/1998 | Tang et al. . |
| 5,883,113 | 3/1999 | Tang et al. . |
| 5,883,116 | 3/1999 | Tang et al. . |
| 5,886,020 | 3/1999 | Tang et al. . |

FOREIGN PATENT DOCUMENTS

| | | |
|---|---|---|
| 0436333 A2 | 12/1990 | (EP) . |
| 0580502 | 7/1993 | (EP) . |
| WO 92/07830 | 5/1992 | (WO) . |
| WO 95/01349 | 1/1995 | (WO) . |
| WO 96/00226 | 1/1996 | (WO) . |
| WO 96/16964 | 6/1996 | (WO) . |
| WO 96/22976 | 8/1996 | (WO) . |
| WO 96/32380 | 10/1996 | (WO) . |
| WO 96/40116 | 12/1996 | (WO) . |
| WO 97/11692 | 4/1997 | (WO) . |
| WO 97/16447 | 5/1997 | (WO) . |
| WO 97/45409 | 12/1997 | (WO) . |
| WO 97/46551 | 12/1997 | (WO) . |
| WO 98/07695 | 2/1998 | (WO) . |
| WO 98/24432 | 6/1998 | (WO) . |
| WO 98/50356 | 11/1998 | (WO) . |
| WO 99/10325 | 3/1999 | (WO) . |
| WO 99/15500 | 4/1999 | (WO) . |
| WO 99/48868 | 9/1999 | (WO) . |
| WO 99/61422 | 12/1999 | (WO) . |
| WO 00 08202 | 2/2000 | (WO) . |
| WO 00 12084 | 3/2000 | (WO) . |

OTHER PUBLICATIONS

Abstract Acc. No. 94–028085/199404 (Abstract of EP 0580502).
Sun et al., J. Med. Chem., 41:2588–2603 (1998).
Sun et al., "Synthesis and Biological Evaluation of Novel–3–[(Substituted pyrrol–2–yl) methylidenyl] indolin–2–ones as Potent and Selective Inhibitors of the Flk–1/KDR Receptor Tyrosine Kinase", Abstract presented at Trip Report: ACS National Meeting, Dallas, Texas, Apr. 1998.

* cited by examiner

Primary Examiner—C. S. Aulakh
(74) Attorney, Agent, or Firm—George W. Johnston; Patricia S. Rocha-Tramaloni

(57) ABSTRACT

Disclosed are novel 4-alkenyl- and 4-alkynyl oxindoles having the formula

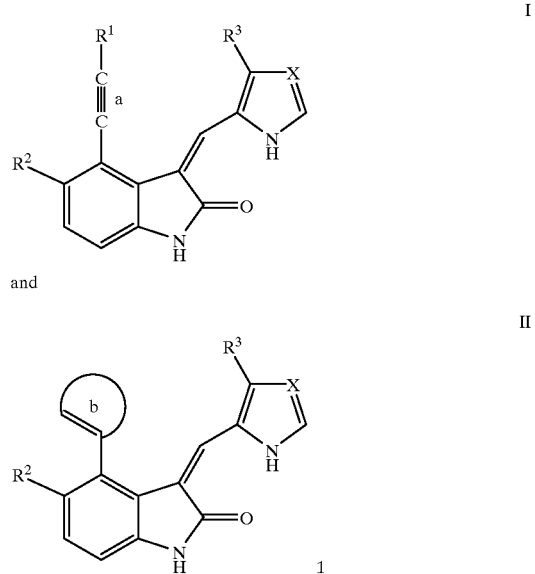

and the pharmaceutically acceptable salts thereof, wherein $R^1$, $R^2$, $R^3$, a, b, and X are as defined herein. These compounds inhibit cyclin-dependent kinases (CDKs), in particular CDK2. These compounds and their pharmaceutically acceptable salts, and prodrugs of said compounds, are anti-proliferative agents useful in the treatment or control of cell proliferative disorders, in particular cancer, more particularly, the treatment or control of breast and colon tumors. Also disclosed are pharmaceutical compositions containing the compounds of formula I and II as well as intermediates useful in the preparation of the compounds of formula I and II.

3 Claims, No Drawings

4-ALKENYL-AND 4-ALKYNYLOXINDOLES

CROSS REFERENCE TO RELATED APPLICATIONS

This is a divisional of application Ser. No. 09/464,502 filed on Dec. 15, 1999, now U.S. Pat. No. 6,130,239 which claims benefit of provisional application No. 60/112,591 filed Dec. 17, 1998, which claims benefit of Ser. No. 60/149,073 filed Aug. 16, 1999.

FIELD OF THE INVENTION

The present invention is directed to novel 4-alkenyl- and 4-alkynyl oxindoles which inhibit cyclin-dependent kinases (CDKs), in particular CDK2. These compounds and their pharmaceutically acceptable salts, and prodrugs of said compounds, are anti-proliferative agents useful in the treatment or control of cell proliferative disorders, in particular cancer. The invention is also directed to pharmaceutical compositions containing such compounds, and to methods for the treatment and/or prevention of cancer, particularly in the treatment or control of solid tumors. The compounds of the invention are especially useful in the treatment or control of breast and colon tumors. The invention is also directed to intermediates useful in the preparation of the above anti-proliferative agents.

BACKGROUND OF THE INVENTION

Uncontrolled cell proliferation is the hallmark of cancer. Cancerous tumor cells typically have some form of damage to the genes that directly or indirectly regulate the cell-division cycle.

Cyclin-dependent kinases (CDKS) are enzymes which are critical to cell cycle control. See, e.g., Coleman et al., "Chemical Inhibitors of Cyclin-dependent Kinases," *Annual Reports in Medicinal Chemistry*, vol. 32, 1997, pp. 171–179. These enzymes regulate the transitions between the different phases of the cell cycle, such as the progression from the $G_1$ phase to the S phase (the period of active DNA synthesis), or the progression from the $G_2$ phase to the M phase, in which active mitosis and cell-division occurs. See, e.g., the articles on this subject appearing in *Science*, vol. 274, Dec. 6, 1996, pp 1643–1677.

CDKs are composed of a catalytic CDK subunit and a regulatory cyclin subunit. The cyclin subunit is the key regulator of CDK activity, with each CDK interacting with a specific subset of cyclins: e.g. cyclin A (CDK1, CDK2). The different kinase/cyclin pairs regulate progression through specific stages of the cell cycle. See, e.g., Coleman, supra.

Aberrations in the cell cycle control system have been implicated in the uncontrolled growth of cancerous cells. See, e.g., Kamb, "Cell-Cycle Regulators and Cancer," *Trends in Genetics*, vol. 11, 1995, pp. 136–140; and Coleman, supra. In addition, changes in the expression of or in the genes encoding CDK's or their regulators have been observed in a number of tumors. See, e.g., Webster, "The Therapeutic Potential of Targeting the Cell Cycle," *Exp. Opin. Invest. Drugs*, Vol. 7, pp. 865–887 (1998), and references cited therein. Thus, there is an extensive body of literature validating the use of compounds inhibiting CDKs as anti-proliferative therapeutic agents. See, e.g. U.S. Pat. No. 5,621,082 to Xiong et al; EP 0 666 270 A2; WO 97/16447; and the references cited in Coleman, supra, in particular reference no. 10. Thus, it is desirable to identify chemical inhibitors of CDK kinase activity.

It is particularly desirable to identify small molecule compounds that may be readily synthesized and are effective in inhibiting one or more CDKs or CDK/cyclin complexes, for treating one or more types of tumors.

Indolinone (also known as oxindole) compounds asserted to be useful in the regulating abnormal cell proliferation through tyrosine kinase inhibition are disclosed in WO 96/40116, WO 98/07695, WO 95/01349, WO 96/32380, WO 96/22976, WO 96/16964 (tyrosine kinase inhibitors), and WO 98/50356 (2-indolinone derivatives as modulators of protein kinase activity). Oxindole derivatives have also been described for various other therapeutic uses: U.S. Pat. No. 5,206,261 (improvement of cerebral function); WO 92/07830 (peptide antagonists); EP 580 502 A1 (antioxidants).

There continues to be a need for easily synthesized, small molecule compounds for the treatment of one or more types of tumors, in particular through regulation of CDKs. It is thus an object of this invention to provide such compounds and compositions containing such compounds.

SUMMARY OF THE INVENTION

The present invention relates to 4-alkenyl- and 4-alkynyloxindoles capable of inhibiting the activity of one or more CDKs, in particular CDK2. Such compounds are useful for the treatment of cancer, in particular solid tumors. In particular the compounds of the present invention are especially useful in the treatment or control of breast and colon tumors. The invention is also directed to intermediate compounds useful in the preparation of the above-mentioned 4-alkenyl- and 4-alkynyloxindoles.

The compounds of the present invention are 4-alkenyl- and 4-alkynyloxindoles having the following formula:

I

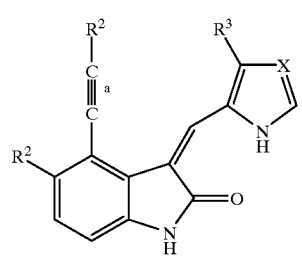

and prodrugs and pharmaceutically active metabolites of compounds of formula I, and the pharmaceutically acceptable salts of the foregoing compounds, wherein:

$R^1$ is selected from the group consisting of
- —H,
- —COR⁴,
- —COOR⁴,
- —CONR⁶R⁷,
- lower alkyl which optionally may be substituted from the group consisting of —OR⁵, —NR⁶R⁷, cycloalkyl, heterocycle, —COR⁴, —COOR⁴, —CONR⁶R⁷, —CN, —NO₂, —SO₂R⁴, —SO₂NR⁶R⁷ and halogen,
- cycloalkyl which optionally may be substituted from the group consisting of —OR⁵, —NR⁶R⁷, lower alkyl, heterocycle, —COR⁴, —COOR⁴, —CONR⁶R⁷, —CN, —NO₂, —SO₂R⁴, —SO₂NR⁶R⁷ and halogen, and
- heterocycle which optionally may be substituted from the group consisting of —OR⁵, —NR⁶R⁷, lower alkyl, cycloalkyl, —COR$^4$, —COOR$^4$, —CONR$^6$R$^7$, —CN, —NO$_2$, —SO$_2$R$^4$, —SO$_2$NR$^6$R$^7$ and halogen;

R$^2$ is selected from the group consisting of
—H,
—OR$^4$,
—COOR$^4$,
—CONR$^6$R$^7$,
—NR$^6$R$^7$,
halogen,
—NO$_2$,
—CN,
—SO$_2$NR$^6$R$^7$,
—SO$_2$R$^4$,
perfluoroalkyl, and
lower alkyl which optionally may be substituted by the group consisting of —OR$^8$ and —NR$^6$R$^7$;

R$^3$ is selected from the group consisting of
—H,
—OR$^4$,
—COR$^4$,
—COOR$^4$,
—CONR$^6$R$^7$,
halogen,
—CN,
—NR$^6$R$^7$,
perfluoroalkyl, and
lower alkyl which optionally may be substituted by the group consisting of —OR$^8$ and —NR$^6$R$^7$;

R$^4$ is selected from the group consisting of
—H,
lower alkyl which optionally may be substituted by the group consisting of —OR$^5$, —COOR$^8$, —COR$^8$, —CONR$^8$R$^9$, —NR$^6$R$^7$, cycloalkyl, heterocycle, —CN, —NO$_2$, —SO$_2$R$^8$, and —SO$_2$NR$^8$R$^9$,
cycloalkyl which optionally may be substituted by the group consisting of —OR$^5$, —COOR$^8$, —COR$^8$, —CONR$^8$R$^9$, —NR$^6$R$^7$, lower alkyl, heterocycle, —CN, —NO$_2$, —SO$_2$R$^8$, and —SO$_2$NR$^8$R$^9$, and
heterocycle which optionally may be substituted by the group consisting of —OR$^5$, —COOR$^8$, —COR$^8$, —CONR$^8$R$^9$, —NR$^6$R$^7$, lower alkyl, cycloalkyl, —CN, —NO$_2$, —SO$_2$R$^8$, and —SO$_2$NR$^8$R$^9$;

R$^5$ is selected from the group consisting of
—H,
—COR$^8$,
—CONR$^8$R$^9$, and
lower alkyl which optionally may be substituted by the group consisting of —OR$^9$, —NR$^9$R$^{10}$, —N(COR$^9$)—R$^{10}$, —COR$^9$, —CONR$^9$R$^{10}$, and —COOR$^9$;

R$^6$ and R$^7$ are each independently selected from the group consisting of
—H,
—COR$^8$,
—COOR$^8$,
—CONR$^8$R$^9$,
—SO$_2$R$^8$,
—SO$_2$NR$^8$R$^9$,
lower alkyl which optionally may be substituted by the group consisting of
—OR$^5$,
—NR$^8$R$^9$,
—COOR$^8$,
COR$^8$,
—CONR$^8$R$^9$,
—CN,
—NO$_2$,
—SO$_2$R$^8$,
—SO$_2$NR$^8$R$^9$,
cycloalkyl which optionally may be substituted by the group consisting of —OR$^5$, —COOR$^8$, —COR$^8$, —CONR$^8$R$^9$, —NR$^8$R$^9$, lower alkyl, heterocycle, —CN, —NO$_2$, —SO$_2$R$^8$, and —SO$_2$NR$^8$R$^9$,
heterocycle which optionally may be substituted by the group consisting of —OR$^5$, —COOR$^8$, —COR$^8$, —CONR$^8$R$^9$, —NR$^8$R$^9$, lower alkyl, cycloalkyl, —CN, —NO$_2$, —SO$_2$R$^8$, and —SO$_2$NR$^8$R$^9$,
aryl which optionally may be substituted by the group consisting of —OR$^5$, —COOR$^8$, —COR$^8$, —CONR$^8$R$^9$, —NR$^8$R$^9$, lower alkyl, heterocycle, —CN, —NO$_2$, —SO$_2$R$^8$, and —SO$_2$NR$^8$R$^9$, and
heteroaryl which optionally may be substituted by the group consisting of —OR$^5$, —COOR$^8$, —COR$^8$, —CONR$^8$R$^9$, —NR$^8$R$^9$, lower alkyl, heterocycle, —CN, —NO$_2$, —SO$_2$R$^8$, and —SO$_2$NR$^8$R$^9$,
cycloalkyl which optionally may be substituted by the group consisting of —OR$^5$, —COOR$^8$, —COR$^8$, —CONR$^8$R$^9$, —NR$^8$R$^9$, lower alkyl, heterocycle, —CN, —NO$_2$, —SO$_2$R$^8$, and —SO$_2$NR$^8$R$^9$,
heterocycle which optionally may be substituted by the group consisting of —OR$^5$, —COOR$^8$, —COR$^8$, —CONR$^8$R$^9$, —NR$^8$R$^9$, lower alkyl, cycloalkyl, —CN, —NO$_2$, —SO$_2$R$^8$, and —SO$_2$NR$^8$R$^9$,
aryl which optionally may be substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$, and
heteroaryl which optionally may be substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$;
or alternatively, —NR$^6$R$^7$ can optionally form a ring having 3 to 7 atoms, said ring optionally including one or more additional hetero atoms and being optionally substituted by the group consisting of one or more of lower alkyl, —OR$^5$, —COR$^8$, —COOR$^8$, —CONR$^8$R$^9$, and —NR$^5$R$^9$;

R$^8$ is selected from the group consisting of
—H,
lower alkyl which optionally may be substituted by the group consisting of cycloalkyl, heterocycle, aryl, heteroaryl, —OR$^9$, —NR$^9$R$^{10}$, and —N(COR$^9$)R$^{10}$,
aryl which optionally may be substituted by the group consisting of —OR$^9$, —COOR$^9$, —COR$^9$, —CONR$^{10}$R$^9$, —NR$^{10}$R$^9$, lower alkyl, cycloalkyl, heterocycle, —CN, —NO$_2$, —SO$_2$R$^9$, and —SO$_2$NR$^{10}$R$^9$, and
heteroaryl which optionally may be substituted by the group consisting of —OR$^9$, —COOR$^9$, —COR$^9$, —CONR$^{10}$R$^9$, —NR$^{10}$R$^9$, lower alkyl, cycloalkyl heterocycle, —CN, —NO$_2$, —SO$_2$R$^9$, and —SO$_2$NR$^{10}$R$^9$;
cycloalkyl which optionally may be substituted by the group consisting of —OR$^9$, —COOR$^9$, —COR$^9$, —CONR$^{10}$R$^9$, —NR$^{10}$R$^9$, lower alkyl, heterocycle, —CN, —NO$_2$, —SO$_2$R$^9$, and —SO$_2$NR$^{10}$R$^9$; and
heterocycle which optionally may be substituted by the group consisting of —OR$^9$, —COOR$^9$, —COR$^9$, —CONR$^{10}$R$^9$, —NR$^{10}$R$^9$, lower alkyl, cycloalkyl, —CN, —NO$_2$, —SO$_2$R$^9$, and —SO$_2$NR$^{10}$R$^9$;

R$^9$ is selected from the group consisting of —H and lower alkyl;

R$^{10}$ is selected from the group consisting of —H and lower alkyl;

X is selected from the group consisting of

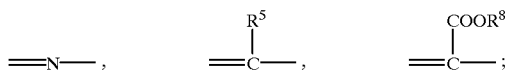

and a is an optional bond.

The present invention is also directed to compounds of formula:

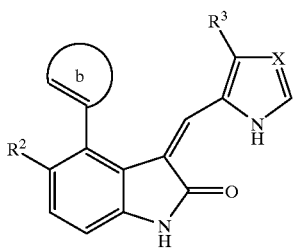

II wherein R$^2$, R$^3$ and X have the same meanings as provided above for compounds of formula I and wherein b is selected from the group consisting of
cycloalkyl which optionally may be substituted from the group consisting of —OR$^5$, —NR$^6$R$^7$, lower alkyl, heterocycle, —COR$^4$, —COOR$^4$, —CONR$^6$R$^7$, —CN, —NO$_2$, —SO$_2$R$^4$, —SO$_2$NR$^6$R$^7$ and halogen, and
heterocycle which optionally may be substituted from the group consisting of —OR$^5$, —NR$^6$R$^7$, lower alkyl, cycloalkyl, —COR$^4$, —COOR$^4$, —CONR$^6$R$^7$, —CN, —NO$_2$, —SO$_2$R$^4$, —SO$_2$NR$^6$R$^7$ and halogen.

The present invention is further directed to pharmaceutical compositions comprising a pharmaceutically effective amount of any one or more of the above-described compounds and a pharmaceutically acceptable carrier or excipient.

The present invention is also directed to a method for treating solid tumors, in particular breast or colon tumors, by administering to a human patient in need of such therapy an effective amount of a compound of formula I or II, their salts and/or prodrugs.

DETAILED DESCRIPTION OF THE INVENTION

Definitions

As used herein, the following terms shall have the following definitions.

"Aryl" means an aromatic group having 5 to 10 atoms and consisting of 1 or 2 rings. Examples of aryl groups include phenyl and 1- or 2-naphthyl.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective Amount" means an amount of at least one compound of Formula I or Formula II, or a pharmaceutically acceptable salt, prodrug or metabolite thereof, that significantly inhibits proliferation and/or prevents differentiation of a human tumor cell, including human tumor cell lines.

"Halogen" means fluorine, chlorine, bromine or iodine.

"Heteroaryl" groups are aromatic groups having 5 to 10 atoms, one or 2 rings, and containing one or more hetero atoms. Examples of heteroaryl groups are 2-, 3- or 4-pyridyl, tetrazolyl, oxadiazolyl, pyrazinyl, quinolyl, pyrrolyl, and imidazolyl.

"Hetero atom" means an atom selected from N, O and S.

"Heterocycle" means a 3- to 10-membered non-aromatic, partially or completely saturated hydrocarbon group, such as tetrahydroquinolyl, which contains one or two rings and at least one hetero atom.

"IC$_{50}$" refers to the concentration of a particular 4-alkenyl or 4-alkynyloxindole required to inhibit 50% of a specific measured activity. IC$_{50}$ can be measured, inter alia, as is described in Example 130, infra.

"Lower Alkyl" denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Pharmaceutically acceptable salt" refers to conventional acid-addition salts or base-addition salts which retain the biological effectiveness and properties of the compounds of formula I or formula II and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide.

"Pharmaceutically acceptable," such as pharmaceutically acceptable carrier, excipient, prodrug, etc., means pharmacologically acceptable and substantially non-toxic to the subject to which the particular compound is administered.

"Pharmaceutically active metabolite" means a metabolic product of a compound of formula I or formula II which is pharmaceutically acceptable and effective.

"Prodrug" refers to a compound that may be converted under physiological conditions or by solvolysis to any of the compounds of formula I or formula II or to a pharmaceutically acceptable salt of a compound of formula I or formula II. A prodrug may be inactive when administered to a subject but is converted in vivo to an active compound of formula I or formula II.

"Substituted," as in substituted alkyl, means that the substitution can occur at one or more positions and, unless otherwise indicated, that the substituents at each substitution site are independently selected from the specified options.

The Compounds

In one embodiment, the current invention is directed to compounds having the formula:

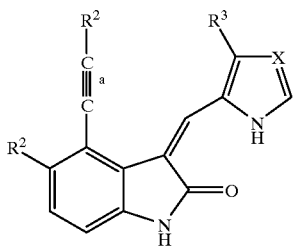

and prodrugs and pharmaceutically active metabolites of compounds of formula I, and the pharmaceutically acceptable salts of the foregoing compounds, wherein:

$R^1$ is selected from the group consisting of
—H,
—$COR^4$,
—$COOR^4$,
—$CONR^6R^7$,
lower alkyl which optionally may be substituted from the group consisting of —$OR^5$, —$NR^6R^7$, cycloalkyl, heterocycle, —$COR^4$, —$COOR^4$, —$CONR^6R^7$, —CN, —$NO_2$, —$SO_2R^4$, halogen, and —$SO_2NR^6R^7$,
cycloalkyl which optionally may be substituted from the group consisting of —$OR^5$, —$NR^6R^7$, lower alkyl, heterocycle, —$COR^4$, —$COOR^4$, —$CONR^6R^7$, —CN, —$NO_2$, —$SO_2R^4$, halogen, and —$SO_2NR^6R^7$,
heterocycle which optionally may be substituted from the group consisting of —$OR^5$, —$NR^6R^7$, lower alkyl, cycloalkyl, —$COR^4$, —$COOR^4$, —$CONR^6R^7$, —CN, —$NO_2$, —$SO_2R^4$, halogen, and —$SO_2NR^6R^7$;

$R^2$ is selected from the group consisting of
—H,
—$OR^4$,
—$COOR^4$,
—$CONR^6R^7$,
—$NR^6R^7$,
halogen,
—$NO_2$,
—CN,
—$SO_2R^4$,
—$SO_2NR^6R^7$,
perfluoroalkyl, and
lower alkyl which optionally may be substituted by the group consisting of —$OR^8$ and —$NR^6R^7$;

$R^3$ is selected from the group consisting of
—H,
$OR^4$,
—$COR^4$,
—$COOR^4$,
—$CONR^6R^7$,
halogen,
—CN,
—$NR^6R^7$,
perfluoroalkyl, and
lower alkyl which optionally may be substituted by the group consisting of —$OR^8$ and —$NR^6R^7$;

$R^4$ is selected from the group consisting of
—H,
lower alkyl which optionally may be substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, and —$SO_2NR^8R^9$,
cycloalkyl which optionally may be substituted by the group consisting of —$OR^5$, —$COOR^8$, —$COR^8$, —$CONR^8R^9$, —$NR^6R^7$, lower alkyl, heterocycle, —CN, —$NO_2$, —$SO_2R^8$, and —$SO_2NR^8R^9$, and
heterocycle which optionally may be substituted by the group consisting of —$OR^5$, —$COOR^8$, —$COR^8$, —$CONR^8R^9$, —$NR^6R^7$, lower alkyl, cycloalkyl, —CN, —$NO_2$, —$SO_2R^8$, and —$SO_2NR^8R^9$;

$R^5$ is selected from the group consisting of
—$COR^8$,
—$CONR^8R^9$, and
lower alkyl which optionally may be substituted by the group consisting of —$OR^9$, —$NR^9R^{10}$, —$N(COR^9)R^{10}$, —$COR^9$, —$CONR^9R^{10}$, and —$COOR^9$;

$R^6$ and $R^7$ are each independently selected from the group consisting of
—H,
—$COR^8$,
—$COOR^8$,
—$CONR^8R^9$,
—$SO_2R^8$,
—$SO_2NR^8R^9$,
lower alkyl which optionally may be substituted by the group consisting of —$OR^5$, —$NR^8R^9$, —$COOR^8$, —$COR^8$, —$CONR^8R^9$, —CN, —$NO_2$, —$SO_2R^8$, —$SO_2NR^8R^9$,
cycloalkyl which optionally may be substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$,
heterocycle which optionally may be substituted by the group consisting of —$OR^5$, —$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$,
aryl which optionally may be substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$, and
heteroaryl which optionally may be substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$,
cycloalkyl which optionally may be substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$,
heterocycle which optionally may be substituted by the group consisting of —$OR^5$, —$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$,
aryl which optionally may be substituted by the group consisting of —$OR^5$, —$COOR^8$, —$COR^8$, —$CONR^8R^9$, —$NR^8R^9$, lower alkyl, cycloalkyl heterocycle, —CN, —$NO_2$, —$SO_2R^8$, and —$SO_2NR^8R^9$, and
heteroaryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$;

or alternatively, —$NR^6R^7$ can optionally form a ring having 3 to 7 atoms, said ring optionally including one or more additional hetero atoms and being optionally substituted by the group consisting of one or more of lower alkyl, —$OR^5$, —$COR^8$, —$COOR^8$, $CONR^8R^9$, and —$NR^5R^9$;

$R^8$ is selected from the group consisting of
—H,
lower alkyl which optionally may be substituted by the group consisting of cycloalkyl, heterocycle, aryl, heteroaryl, —$OR^9$, —$NR^9R^{10}$, and —$N(COR^9)R^{10}$,
aryl which optionally may be substituted by the group consisting of —$OR^9$, —$COOR^9$, —$COR^9$, —$CONR^{10}R^9$, —$NR^{10}R^9$, lower alkyl, cycloalkyl, heterocycle, —CN, —$NO_2$, —$SO_2R^9$, and —$SO_2NR^{10}R^9$,
heteroaryl which optionally may be substituted by the group consisting of —$OR^9$, —$COOR^9$, —$COR^9$, —$CONR^{10}R^9$, —$NR^{10}R^9$, lower alkyl, cycloalkyl, heterocycle, —CN, —$NO_2$, —$SO_2R^9$, and —$SO_2NR^{10}R^9$;
cycloalkyl which optionally may be substituted by the group consisting of —$OR^9$, —$COOR^9$, —$COR^9$, —$CONR^{10}R^9$, —$NR^{10}R^9$, lower alkyl, heterocycle, —CN, —$NO_2$, —$SO_2R^9$, and —$SO_2NR^{10}R^9$; and
heterocycle which optionally may be substituted by the group consisting of —$OR^9$, —$COOR^9$, —$COR^9$, —$CONR^{10}R^9$, —$NR^{10}R^9$, lower alkyl, cycloalkyl, —CN, —$NO_2$, —$SO_2R^9$, and —$SO_2NR^{10}R^9$;

$R^9$ is selected from the group consisting of —H and lower alkyl;

$R^{10}$ is selected from the group consisting of —H and lower alkyl;

X is selected from the group consisting of

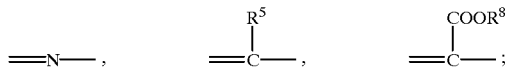

and a is an optional bond.

In a preferred embodiment of the compounds of formula I, $R^1$ is selected from the group consisting of
—$COR^4$,
lower alkyl which optionally may be substituted by the group consisting of —$OR^4$, —$NR^6R^7$, —$COR^4$, —$COOR^4$, —$CONR^6R^7$, —$NO_2$, cycloalkyl, and heterocycle,
cycloalkyl which optionally may be substituted by the group consisting of —$OR^4$, —$NR^6R^7$, —$COR^4$, —$COOR^4$, —$CONR^6R^7$, —$NO_2$, lower alkyl, and heterocycle, and
heterocycle which optionally may be substituted by the group consisting of —$OR^4$, —$NR^6R^7$, —$COR^4$, —$COOR^4$, —$CONR^6R^7$, —$NO_2$, lower alkyl, and cycloalkyl.

In another preferred embodiment of the compounds of formula I, $R^2$ is selected from the group consisting of —H, —$OR^4$, $NO_2$, perfluoroalkyl, —$NR^6R^7$, fluoride, and lower alkyl which optionally may be substituted by the group consisting of $OR^8$ and $NR^6R^7$. Preferred perfluoroalkyls include —$CF_3$.

In another preferred embodiment of the compounds of formula I, $R^3$ is selected from the group consisting of —H, —$OR^4$, —$NR^6R^7$, and -lower alkyl which optionally may be substituted by the group consisting of —$OR^8$ and —$NR^6R^7$.

In another preferred embodiment of the compounds of formula I, $R^4$ is selected from the group consisting of —H and lower alkyl which optionally may be substituted by the group consisting of —$NR^6R^7$, —$OR^5$, —$COOR^8$, —$COR^8$ and —$CONR^8R^9$.

In another preferred embodiment of the compounds of formula I, $R^5$ is selected from the group consisting of H, —$COR^8$, —$CONR^8R^9$, and lower alkyl.

In another preferred embodiment of the compounds of formula I, $R^6$ and $R^7$ are each independently selected from the group consisting of —H, —$COR^8$, —$COOR^8$, —$CONR^8R^9$, —$SO_2R^8$, and lower alkyl which optionally may be substituted by the group consisting of $OR^5$, and —$NR^8R^9$; or alternatively, —$NR^6R^7$ can optionally form a ring having 3 to 7 atoms, said ring optionally including one or more additional hetero atoms and being optionally substituted by the group consisting of one or more —$OR^5$ and —$NR^5R^9$.

In another preferred embodiment of the compounds of formula I, $R^8$ is selected from the group consisting of —H and lower alkyl which optionally may be substituted by the group consisting of aryl, heteroaryl, —$OR^9$, —$NR^9R^{10}$, and —$N(COR^9)R^{10}$.

In another preferred embodiment of the compounds of formula I, X is =$CR^5$— and "a" is a bond.

In another preferred embodiment of the compounds of formula I, X is =N— and "a" is a bond.

The following are examples of preferred compounds of formula I:

(Z)-1,3-dihydro-4-(6-hydroxy-1-hexynyl)-3-[(3-methoxy-1H-pyrrol-2-yl)methylene]-2H-indol-2-one (A), (Z)-1,3-dihydro-4-(5-hydroxy-1-pentynyl)-3-[(3-methoxy-1H-pyrrol-2-yl)methylene]-2H-indol-2-one (B), (Z)-1,3-dihydro-4-(4-hydroxy-1-butynyl)-3-[(3-methoxy-1H-pyrrol-2-yl)methylene]-2H-indol-2-one (C), rac-(Z)-1,3-dihydro-4-(3-hydroxy-3-methyl-1-pentynyl)-3-[(3-methoxy-1H-pyrrol-2-yl)methylene]-2H-indol-2-one (D), (Z)-1,3-dihydro-4-(3-hydroxy-3-methyl-1-butynyl)-3-[(3-methoxy-1H-pyrrol-2-yl)methylene]-2H-indol-2-one (L), (Z)-1,3-dihydro-4-[(1-hydroxycyclohexyl)ethynyl]-3-[(3-methoxy-1H-pyrrol-2-yl)methylene]-2H-indol-2-one (M), rac-(Z)-1,3-dihydro-4-(3-hydroxy-3-methyl-1-hexynyl)-3-[(3-methoxy-1H-pyrrol-2-yl)methylene]-2H-indol-2-one (N), rac-(Z)-1,3-dihydro-4-(3,5-dimethyl-3-hydroxy-1-hexynyl)-3-[(3-methoxy-1H-pyrrol-2-yl)methylene]-2H-indol-2-one (O), (R)-(Z)-1,3-dihydro-4-(3-hydroxy-1-octynyl)-3-[(3-methoxy-1H-pyrrol-2-yl)methylene]-2H-indol-2-one (P), rac-(Z)-1,3-dihydro-4-(3-hydroxy-1-octynyl)-3-[(3-methoxy-1H-pyrrol-2-yl)methylene]-2H-indol-2-one (Q), rac-(Z)-1,3-dihydro-4-(3-hydroxy-1-pentynyl)-3-[(3-methoxy-1H-pyrrol-2-yl)methylene]-2H-indol-2-one (R), (Z)-1,3-Dihydro-4-[3-(2-hydroxyethoxy)-1-propynyl]-3-[(3-methoxy-1H-pyrrol-2-yl)methylene]-2H-indol-2-one (S), rac-(Z)-4-[3-[(2,2-dimethyl-1,3-dioxotan-4-yl)methoxy]-1-propynyl]-1,3-dihydro-3-[(3-methoxy-1H-pyrrol-2-yl)methylene]-2H-indol-2-one (T),(S)-(Z)-1,3-dihydro-4-(3-hydroxy-1-octynyl)-3-[(3-methoxy-1H-pyrrol-2-yl)methylene]-2H-indol-2-one (U), (Z)-1,3-dihydro-4-(3-hydroxy-1-propynyl)-3-[(3-methoxy-1H-pyrrol-2-yl)methylene]-2H-indol-2-one (Y), and (Z)-1,3-dihydro-4-[(1-hydroxycyclopentyl)ethynyl]-3-[(3-methoxy-1H-pyrrol-2-yl)methylene]-2H-indol-2-one (AA).

The following are examples of additional preferred compounds of formula I:

(Z)-6-[2,3-Dihydro-3-[(3-methoxy-1H-pyrrol-2-yl)methylene]-2-oxo-1H-indol-4-yl]-5-hexynoic acid methyl ester (E), (Z)-5-[2,3-Dihydro-3-[(3-methoxy-1H-pyrrol-2-yl)methylene]-2-oxo-1H-indol-4-yl]-4-pentynoic acid methyl ester (F), (Z)-6-[2,3-Dihydro-3-[(3-methoxy-1H-pyrrol-2-yl)methylene]-2-oxo-1H-indol-4-yl]-5-hexynoic acid (G), (Z)-5-[2,3-Dihydro-3-[(3-methoxy-1H-pyrrol-2-yl)methylene]-2-oxo-1H-indol-4-yl]-4-pentynoic acid (H), (Z)-5-[2,3-Dihydro-3-[(3-methoxy-1H-pyrrol-2-yl)methylene]-2-oxo-1H-indol-4-yl]-4-pentynoic acid Sodium salt (I), (Z)-5-[2,3-Dihydro-3-[(3-methoxy-1H-pyrrol-2-yl)methylene]-2-oxo-1H-indol-4-yl]-4-pentynamide (J), (Z)-6-[2,3-Dihydro-3-[(3-methoxy-1H-pyrrol-2-yl)methylene]-2-oxo-1H-indol-4-yl]-5-hexynamide (K), (Z)-[3-[2,3-Dihydro-3-[(3-methoxy-1H-pyrrol-2-yl)methylene]-2-oxo-1H-indol-4-yl]-2-propynyl] propanedioic acid dimethyl ester (V), and (Z)-[3-[2,3-Dihydro-3-[(3-methoxy-1H-pyrrol-2-yl)methylene]-2-oxo-1H-indol-4-yl]-2-propynyl] propanedioic acid (W).

The following are examples of additional preferred compounds of formula I:

(Z)-1,3-Dihydro-4-[3-(2-hydroxyethoxy)-1-propynyl]-3-[(3-methoxy-1H-pyrrol-2-yl)methylene]-2H-indol-2-one (S), and (Z)-1,3-Dihydro-4-(3-methoxy-1-propynyl)-3-[(3-methoxy-1H-pyrrol-2-yl)methylene]-2H-indol-2-one (X).

The following are examples of additional preferred compounds of formula I:

(Z)-1,3-Dihydro-4-(3-hydroxy-1-propynyl)-3-[(3-methoxy-1H-pyrrol-2-yl)methylene]-5-nitro-2H-indol-2-one (Z), (Z)-5-Amino-1,3-dihydro-4-(3-hydroxy-1-propynyl)-3-[(3-methoxy-1H-pyrrol-2-yl)methylene]-2H-indol-2-one (BB), (Z)-N-[2,3-Dihydro-3-[(3-methoxy-1H-pyrrol-2-yl)methylene]-2-oxo-4-(3-hydroxy-1-propynyl)-1H-indol-5-yl]-2-thiopheneacetamide (CC), and (Z)-N-[2,3-Dihydro-4-(3-hydroxy-1-propynyl)-3-[(3-methoxy-1H-pyrrol-2-yl)methylene]-2-oxo-1H-indol-5-yl]-4-pyridinecarboxamide (DD).

The following are examples of additional preferred compounds of formula I:

(Z)-5-[2,3-Dihydro-3-[(3-methoxy-1H-pyrrol-2-yl)methylene]-5-nitro-2-oxo-1H-indol-4-yl]-4-pentynoic acid methyl ester (EE), (Z)-5-[5-Amino-2,3-dihydro-3-[(3-methoxy-1H-pyrrol-2-yl)methylene]-2-oxo-1H-indol-4-yl]-4-pentynoic acid methyl ester (FF), (Z)-5-[2,3-Dihydro-3-[(3-methoxy-1H-pyrrol-2-yl)methylene]-2-oxo-5-[(2-thienylacetyl)amino]-1H-indol-4-yl]-4-pentyonic acid methyl ester (GG), and (Z)-5-[2,3-Dihydro-3-[(3-methoxy-1H-pyrrol-2-yl)methylene]-2-oxo-5-[(2-thienylacetyl)amino]-1H-indol-4-yl]-4-pentynoic acid (HH).

The following are examples of additional preferred compounds of formula I:

(Z)-4-(3-Amino-1-propynyl)-1,3-dihydro-3-[(3-methoxy-1H-pyrrol-2-yl)methylene]-2H-indol-2-one trifluoroacetate salt (II), (Z)-1,3-Dihydro-3-[(3-methoxy-1H-pyrrol-2-yl)methylene]-4-[3-(N-methylamino)-1-propynyl]-2H-indol-2-one trifluoroacetate salt (JJ), (Z)-1,3-Dihydro-3-[(3-methoxy-1H-pyrrol-2-yl)methylene]-4-[3-(N-phenylmethylamino)-1-propynyl]-2H-indol-2-one (KK), (Z)-[3-[2,3-Dihydro-3-[(3-methoxy-1H-pyrrol-2-yl)methylene]-2-oxo-1H-indol-4-yl]-2-propynyl] carbamic acid methyl ester (LL), (Z)-Carbamic acid 3-[2,3-dihydro-3-[(3-methoxy-1H-pyrrol-2-yl)methylene]-2-oxo-1H-indol-4-yl]-2-propynyl ester (MM), and (Z)-N-Methylcarbamic acid 3-[2,3-dihydro-3-[(3-methoxy-1H-pyrrol-2-yl)methylene]-2-oxo-1H-indol-4-yl]-2-propynyl ester (NN).

The following are examples of additional preferred compounds of formula I:

rac-(Z)-1,3-Dihydro-5-fluoro-4-(3-hydroxy-1-pentynyl)-3-[(4-methyl-1H-imidazol-5-yl)methylene]-2H-indol-2-one (OO), (Z)-1,3-Dihydro-5-fluoro-4-(3-hydroxy-1-propynyl)-3-[(4-methyl-1H-imidazol-5-yl)methylene]-2H-indol-2-one, trifluoroacetate salt (QQ), (Z)-1,3-Dihydro-5-fluoro-4-[3-(N-methylamino)-1-propynyl]-3-[(4-methyl-1H-imidazol-5-yl)methylene]-2H-indol-2-one (RR), rac-(Z)-1,3-Dihydro-5-fluoro-4-(4-hydroxy-1-pentynyl)-3-[(4-methyl-1H-imidazol-5-yl)methylene]-2H-indol-2-one, trifluoroacetate salt (TT), (Z)-1,3-Dihydro-4-[3-(N,N-dimethylamino)-1-propynyl]-5-fluoro-3-[(4-methyl-1H-imidazol-5-yl)methylene]-2H-indol-2-one (UU), (Z)-4-[3-Amino-3-methyl-1-butynyl]-1,3-dihydro-5-fluoro-3-[(4-methyl-1H-imidazol-5-yl)methylene]-2H-indol-2-one (VV), (Z)-Carbamic acid 3-[2,3-dihydro-3-[(4-methyl-1-H-imidazol-5-yl)methylene]-5-fluoro-2-oxo-1H-indol-4-yl]-2-propynyl ester (WW), (Z)-1,3-Dihydro-5-fluoro-3-[(4-methyl-1H-imidazol-5-yl)methylene]-4-[3-(4-morpholinyl)-1-propynyl]-2H-indol-2-one (XX), (Z)-[3-[2,3-Dihydro-5-fluoro-3-[(4-methyl-1H-imidazol-5-yl)methylene]-2-oxo-1H-indol-4-yl]-2-propynyl] carbamic acid methyl ester (YY), (Z)-[3-[5-fluoro-2,3-dihydro-3-[(4-methyl-1H-imidazol-5-yl)methylene]-2-oxo-1H-indol-4-yl]-2-propynyl] urea (ZZ), rac-(Z)-2-(Acetylamino)-5-[5-fluoro-2,3,dihydro-3-[(4-methyl-1H-imidazol-5-yl)methylene]-2-oxo-1H-indol-4-yl]-4-pentynoic acid ethyl ester (AAA), (Z)-4-[3-(N,N-Diethylamino)-1-propynyl]-1,3-dihydro-5-fluoro-3-[(4-methyl-1H-imidazol-5-yl)methylene]-2H-indol-2-one (BBB), (Z)-4-[3-Amino-3-ethyl-1-pentynyl]-1,3-dihydro-5-fluoro-3-[(4-methyl-1H-imidazol-5-yl)methylene]-2H-indol-2-one (CCC), (Z)-[3-[2,3-Dihydro-5-fluoro-3-[(4-methyl-1H-imidazol-5-yl)methylene]-2-oxo-1H-indol-4-yl]-1,1-dimethyl-2-propynyl]carbamic acid methyl ester (DDD), N-[3-[2,3-Dihydro-5-fluoro-3-(5-methyl-3H-imidazol-4-yl-methylene)-2-oxo-1H-indol-4-yl]-prop-2-ynyl]-acetamide (EEE), (Z)-1,3-Dihydro-5-fluoro-3-[(4-methyl-1H-imidazol-5-yl)methylene]-4-[3-(1-piperidinyl)-1-propynyl-2H-indol-2-one (FFF), and rac-(Z)-1,3-Dihydro-4-(3-hydroxy-1-pentynyl)-3-[(4-methyl-1H-imidazol-5-yl)methylene]-5-nitro-2H-indol-2-one (PP).

The following are examples of additional preferred compounds according to this invention:

3-[2,3-dihydro-(Z)-3-[(1H-pyrrol-2-yl)methylene]-2-oxo-1H-indol-4-yl]-(E)-2-propenoic acid methyl ester (GGG), 3-[2,3-Dihydro-(Z)-3-[(3-methoxy-1H-pyrrol-2-yl)methylene]-2-oxo-1H-indol-4-yl]-(E)-2-propenoic acid methyl ester (HHH), 1,3-Dihydro-4-(3-hydroxy-propenyl)-3-[(3-methoxy-1H-pyrrol-2-yl)methylene]-indol-2-one (III), 1,3-Dihydro-4-(4-hydroxy-but-1-enyl)-3-[(3-methoxy-1H-pyrrol-2-yl)methylene]-indol-2-one (JJJ), (Z)-1,3-Dihydro-4-ethynyl-3-[(3-methoxy-1H-pyrrol-2-yl)methylene]-2H-indol-2-one, (Z)-1,3-Dihydro-3-[(3-methoxy-1H-pyrrol-2-yl)methylene]-4-(2-trimethylsityl-ethynyl)-2H-indol-2-one, (R)-(Z)-1,3-Dihydro-5-fluoro-4-(4-hydroxy-1-pentynyl)-3-[(4-methyl-1H-imidazol-5-yl)methylene]-2H-indol-2-one (KKK), (S)-(Z)-1,3-Dihydro-5-fluoro-4-(4-hydroxy-1-pentynyl)-3-[(4-methyl-1H-imidazol-5-yl)methylene]-2H-indol-2-one (LLL), rac-(Z)-1,3-Dihydro-5-fluoro-4-(3-hydroxy-1-pentynyl)-3-[(3-methoxy-1H-pyrrol-2-yl)methylene]-2H-indol-2-one (MMM), rac-(Z)-1,3-Dihydro-5-fluoro-4-(3-hydroxy-1-pentynyl)-3-[(1H-pyrrol-2-yl)methylene]-2H-indol-2-one (NNN), (Z)-1,3-Dihydro-5-fluoro-4-[3-(N-methylamino)-1-propynyl]-3-[(1H-pyrrol-2-yl)methylene]-2H-indol-2-one (OOO), (Z)-1,3-Dihydro-5-fluoro-4-[3-(N-methylamino)-1-propynyl]-3-[(3-methoxy-1H-pyrrol-2-yl)methylene]-2H-indol-2-one (PPP), (Z)-1,3-Dihydro-5-fluoro-4-[3-(N-methylamino)-1-propynyl]-3-[(3-methoxy-1H-pyrrol-2-yl)methylene]-2H-indol-2-one hydrochloride salt (QQQ), (R)-(Z)-1,3-Dihydro-5-fluoro-4-(3-hydroxy-1-butynyl)-3-[(4-methyl-1H-imidazol-5-yl)methylene]-2H-indol-2-one (RRR), (R)-(Z)-1,3-Dihydro-5-fluoro-4-(4-hydroxy-1-pentynyl)-3-[(3-methoxy-1H-pyrrol-2-yl)methylene]-2H-indol-2-one (SSS), (Z)-5-[2,3-Dihydro-5-fluoro-3-[(3-methoxy-1H-pyrrol-2-yl)methylene]-2-oxo-1H-indol-4-yl]-4-pentynoic acid methyl ester (TTT), (Z)-1,3-Dihydro-5-fluoro-4-[(1-hydroxy-cyclopentyl)ethynyl]-3-[(3-methoxy-1H-pyrrol-2-yl)methylene]-2H-indol-2-one (UUU), (S)-(Z)-1,3-Dihydro-5-fluoro-4-(4-hydroxy-1-pentynyl)-3-[(3-methoxy-1H-pyrrol-2-yl)methylene]-2H-indol-2-one (VVV), (R)-(Z)-1,3-Dihydro-5-fluoro-4-(3-hydroxy-1-butynyl)-3-[(3-methoxy-1H-pyrrol-2-yl)methylene]-2H-indol-2-one (WWW), (S)-(Z)-1,3-Dihydro-5-fluoro-4-(3-hydroxy-1-butynyl)-3-[(3-methoxy-1H-pyrrol-2-yl)methylene]-2H-indol-2-one (XXX), (S)-(Z)-1,3-Dihydro-5-fluoro-4-(3-hydroxy-1-butynyl)-3-[(4-methyl-1H-imidazol-5-yl)methylene]-2H-indol-2-one (YYY), (Z)-1,3-Dihydro-5-fluoro-4-[(4-hydroxy-tetrahydro-pyran-4-yl)ethynyl]-3-[(3-methoxy-1H-pyrrol-2-yl)methylene]-2H-indol-2-one (ZZZ), (Z)-1,3-Dihydro-4-[(4-hydroxy-tetrahydro-pyran-4-yl)ethynyl]-3-[(3-methoxy-1H-pyrrol-2-yl)methylene]-5-nitro-2H-indol-2-one (AAAA), (S)-(Z)-1,3-Dihydro-5-fluoro-3-[(3-methoxy-1H-pyrrol-2-yl)methylene]-4-[(pyrrolidin-2-yl)ethynyl]-2H-indol-2-one (BBBB), (S)-(Z)-1,3-Dihydro-5-fluoro-3-[(3-methoxy-1H-pyrrol-2-yl)methylene]-4-[(pyrrolidin-2-yl)ethynyl]-2H-indol-2-one hydrochloride salt (CCCC), (R)-(Z)-1,3-Dihydro-5-fluoro-3-[(3-methoxy-1H-pyrrol-2-yl)methylene]-4-[(pyrrolidin-2-yl)ethynyl]-2H-indol-2-one (DDDD), (Z)-3-[(4-Acetyl-1H-pyrrol-2-yl)methylene]-1,3-dihydro-5-fluoro-4-[(4-hydroxy-tetrahydro-pyran-4-yl)ethynyl]-2H-indol-2-one (EEEE), (R)-(Z)-4-(3-Amino-4-hydroxy-1-butynyl)-1,3-dihydro-5-fluoro-3-[(3-methoxy-1H-pyrrol-2-yl)methylene]-2H-indol-2-one (FFFF), (R)-(Z)-1,3-Dihydro-5-fluoro-4-[3-(3-hydroxy-pyrrolidin-1-yl)-1-propynyl]-3-[(3-methoxy-1H-pyrrol-2-yl)methylene]-2H-indol-2-one (GGGG), (S)-(Z)-4-(3-Amino-4-hydroxy-1-butynyl)-1,3-dihydro-5-fluoro-3-[(3-methoxy-1H-pyrrol-2-yl)methylene]-2H-indol-2-one (HHHH), (Z)-3-[(4-Acetyl-1H-pyrrol-2-yl)methylene]-1,3-dihydro-5-fluoro-4-[3-(N-methylamino)-1-propynyl]-2H-indol-2-one (IIII), (Z)-3-[(4-Acetyl-1H-pyrrol-2-yl)methylene]-1,3-dihydro-5-fluoro-4-[3-(N-methylamino)-1-propynyl]-2H-indol-2-one hydrochloride salt (JJJJ), (S)-(Z)-1,3-Dihydro-5-fluoro-4-[3-(3-hydroxy-pyrrolidin-1-yl)-1-propynyl]-3-[(3-methoxy-1H-pyrrol-2-yl)methylene]-2H-indol-2-one (KKKK), rac-(Z)-3-[(4-Acetyl-1H-pyrrol-2-yl)methylene]-1,3-dihydro-5-fluoro-4-[(3-hydroxy-pyrrolidin-3-yl)ethynyl]-2H-indol-2-one (LLLL), rac-(Z)-3-[(4-Acetyl-1H-pyrrol-2-yl)methylene]-1,3-dihydro-5-fluoro-4-[(3-hydroxy-pyrrolidin-3-yl)ethynyl]-2H-indol-2-one hydrochloride salt (MMMM), (Z)-1,3-Dihydro-5-fluoro-4-[(2S,4R)-(4-hydroxy-pyrrolidin-2-yl)-ethynyl]-3-[(3-methoxy-1H-pyrrol-2-yl)methylene]-2H-indol-2-one (NNNN), (Z)-1,3-Dihydro-5-fluoro-4-[(2S,4R)-(4-hydroxy-pyrrolidin-2-yl)-ethynyl]-3-[(3-methoxy-1H-pyrrol-2-yl)methylene]-2H-indol-2-one hydrochloride salt (OOOO), (Z)-1,3-Dihydro-5-fluoro-4-[(4-hydroxy-piperidin-4-yl)-ethynyl]-3-[(3-methoxy-1H-pyrrol-2-yl)methylene]-2H-indol-2-one hydrochloride salt (PPPP), (Z)-4-[(3R,4R)-3-Amino-4-hydroxy-1-pentynyl]-1,3-dihydro-5-fluoro-3-[(3-methoxy-1H-pyrrol-2-yl)methylene]-2H-indol-2-one (QQQQ), (Z)-1,3-Dihydro-5-fluoro-4-[(2S,4S)-(4-hydroxy-pyrrolidin-2-yl)-ethynyl]-3-[(3-methoxy-1H-pyrrol-2-yl)methylene]-2H-indol-2-one (RRRR), (R)-(Z)-1,3-Dihydro-5-fluoro-4-[4-hydroxy-3-methylamino-1-butynyl]-3-[(3-methoxy-1H-pyrrol-2-yl)methylene]-2H-indol-2-one (SSSS), (Z)-4-[(3S,4S,5R)-4-Amino-3,5-dihydroxy-1-hexynyl]-1,3-dihydro-5-fluoro-3-[(3-methoxy-1H-pyrrol-2-yl)methylene]-2H-indol-2-one (TTTT), (Z)-4-[(3R,4S,5R)-4-Amino-3,5-dihydroxy-1-hexynyl]-1,3-dihydro-5-fluoro-3-[(3-methoxy-1H-pyrrol-2-yl)methylene]-2H-indol-2-one (UUUU), rac-(Z)-1,3-Dihydro-5-fluoro-4-[(3-hydroxy-pyrrolidin-3-yl)ethynyl]-3-[(3-methoxy-1H-pyrrol-2-yl)methylene]-2H-indol-2-one hydrochloride salt (VVVV), (Z)-1,3-Dihydro-4-(3-ethylamino-1-proynyl)-5-fluoro-3-[(3-methoxy-1H-pyrrol-2-yl)methylene]-2H-indol-2-one hydrochloride salt (WWWW), (S)-(Z)-3-[(4-Acetyl-1H-pyrrol-2-yl)methylene]-1,3-dihydro-5-fluoro-4-[(pyrrolidin-2-yl)ethynyl]-2H-indol-2-one (XXXX), (S)-(Z)-3-[(4-Acetyl-1H-pyrrol-2-yl)methylene]-1,3-dihydro-5-fluoro-4-[(pyrrolidin-2-yl)ethynyl]-2H-indol-2-one hydrochloride salt (YYYY), (Z)-3-[(4-Acetyl-1H-pyrrol-2-yl)methylene]-1,3-dihydro-5-fluoro-4-[(2S,4R)-(4-hydroxy-pyrrolidin-2-yl)ethynyl]-2H-indol-2-one (ZZZZ), (Z)-3-[(4-Acetyl-1H-pyrrol-2-yl)methylene]-1,3-dihydro-5-fluoro-4-[(2S,4R)-(4-hydroxy-pyrrolidin-2-yl)ethynyl]-2H-indol-2-one hydrochloride salt (AAAAA), (Z)-3-[(4-Acetyl-1H-pyrrol-2-yl)methylene]-1,3-dihydro-4-[(3-ethylamino)-1-propynyl]-5-fluoro-2H-indol-2-one hydrochloride salt (BBBBB), (Z)-3-[(4-Acetyl-1H-pyrrol-2-yl)methylene]-1,3-dihydro-5-fluoro-4-[(4-hydroxy-piperidin-4-yl)ethynyl]-2H-indol-2-one hydrochloride salt (CCCCC), (S)-(Z)-1,3-Dihydro-5-fluoro-4-[3-methylamino-4-hydroxy-1-butynyl]-3-[(3-methoxy-1H-pyrrol-2-yl)methylene]-2H-indol-2-one (DDDDD), (Z)-5-[[4-(3-Ethylamino-prop-1-ynyl)-5-fluoro-2-oxo-1,2-dihydro-indol-3-ylidene]methyl]-4-methyl-1H-pyrrole-3-carboxylic acid ethyl ester hydrochloride salt (EEEEE), (Z)-1,3-Dihydro-5-fluoro-4-[(3R,4R)-4-hydroxy-3-methylamino-1-pentynyl]-3-[(3-methoxy-1H-pyrrol-2-yl)methylene]-2H-indol-2-one (FFFFF), (Z)-1,3-Dihydro-5-fluoro-4-[(3R,4R)-4-hydroxy-3-methylamino-1-pentynyl]-3-[(3-methoxy-1H-pyrrol-2-yl)methylene]-2H-indol-2-one hydrochloride salt (GGGGG), (Z)-N-[3-[5-Fluoro-3-[(3-methoxy-1H-pyrrol-2-yl)methylene]-2-oxo-2,3-dihydro-1H-indol-4-yl]-prop-2-ynyl]-4-methyl-benzenesulfonamide (HHHHH), (Z)-N-[3-[5-Fluoro-3-[(3-methoxy-1H-pyrrol-2-yl)methylene]-2-oxo-2,3-dihydro-1H-indol-4-yl]-prop-2-ynyl]-methanesulfonamide (IIIII), (S)-(Z)-5-[[5-Fluoro-2-oxo-4-[(pyrrolidin-2-yl)ethynyl]-1,2-dihydro-indol-3-ylidene]methyl]-4-methyl-1H-pyrrole-3-carboxylic acid ethyl ester (JJJJJ), (S)-(Z)-5-[[5-Fluoro-2-oxo-4-[(pyrrolidin-2-yl)ethynyl]-1,2-dihydro-indol-3-ylidene]methyl]-4-methyl-1H-pyrrole-3-carboxylic acid ethyl ester hydrochloride salt (KKKKK), (Z)-1,3-Dihydro-4-[(3R,4S,5R)-3,5-dihydroxy-4-ethylamino-1-hexynyl]-5-fluoro-3-[(3-methoxy-1H-pyrrol-2-yl)methylene]-2H-indol-2-one (LLLLL), (R)-(Z)-1,3-Dihydro-4-[(5-ethylamino-6-methyl)-6H-pyran-2-yl]-5-fluoro-3-[(3-methoxy-1H-pyrrol-2-yl)methylene)]-2H-indol-2-one (MMMMM), (Z)-1,3-Dihydro-4-[(3S,4S,5R)-3,5-dihydroxy-4-ethylamino-1-hexynyl]-5-fluoro-3-[(3-methoxy-1H-pyrrol-2-yl)methylene]-2H-indol-2-one (NNNNN), rac (Z)-1,3-Dihydro-5-fluoro-4-[3-(2-hydroxy-propylamino)-1-propynyl]-3-[(3-methoxy-1H-pyrrol-2-yl)methylene]-2H-indol-2-one hydrochloride salt (OOOOO), rac-(Z)-3-[(4-Acetyl-1H-pyrrol-2-yl)methylene]-1,3-dihydro-5-fluoro-4-[3-(2-hydroxy-propylamino)-1-propynyl]-2H-indol-2-one hydrochloride salt (PPPPP), (Z)-3-[(4-Acetyl-1H-pyrrol-2-yl)methylene]-1,3-dihydro-4-[(3R,4S,5R)-3,5-dihydroxy-4-ethylamino-1-hexynyl]-5-fluoro-2H-indol-2-one (QQQQQ), (R)-(Z)-3-[(4-Acetyl-1H-pyrrol-2-yl)methylene]-1,3-dihydro-4-[(5-ethylamino-6-methyl)-6H-pyran-2-yl]-5-fluoro-2H-indol-2-one (RRRRR), (Z)-3-[(4-Acetyl-1H-pyrrol-2-yl)methylene]-4-[(3R,4S,5R)-4-amino-3,5-dihydroxy-1-hexynyl]-1,3-dihydro-5-fluoro-2H-indol-2-one (SSSSS), and (Z)-3-[(4-Acetyl-1H-pyrrol-2-yl)methylene]-4-[(3S,4S,5R)-4-amino-3,5-dihydroxy-1-hexynyl]-1,3-dihydro-5-fluoro-2H-indol-2-one (TTTTT).

The present invention is also directed to compounds of formula II

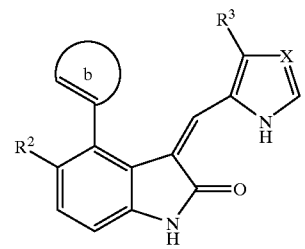

wherein $R^2$, $R^3$ and X have the same meanings as provided above for compounds of formula I and wherein b is selected from the group consisting of cycloalkyl which optionally may be substituted from the group consisting of —$OR^5$, —$NR^6R^7$, lower alkyl, heterocycle, —$COR^4$, —$COOR^4$, —$CONR^6R^7$, —CN, —$NO_2$, —$SO_2R^4$, —$SO_2NR^6R^7$ and halogen, and heterocycle which optionally may be substituted from the group consisting of —$OR^5$, —$NR^6R^7$, lower alkyl, cycloalkyl, —$COR^4$, —$COOR^4$, —$CONR^6R^7$, —CN, —$NO_2$, —$SO_2R^4$, —$SO_2NR^6R^7$ and halogen.

The following intermediates are also examples of additional preferred compounds according to the present invention:

(Z)-4-Bromo-1,3-dihydro-3-[(3-methoxy-1H-pyrrol-2-yl)methylene]-2H-indol-2-one, (Z)-1,3-Dihydro-4-iodo-3-[(3-methoxy-1H-pyrrol-2-yl)methylene]-2H-indol-2-one, (Z)-1,3-Dihydro-5-fluoro-4-iodo-3-[(4-methyl-1H-imidazol-5-yl)methylene]-2H-indol-2-one, (Z)-1,3-Dihydro-4-iodo-3-[(4-methyl-1H-imidazol-5-yl)methylene]-5-nitro-2H-indol-2-one, (Z)-4-Bromo-1,3-dihydro-5-fluoro-3-[(3-methoxy-1H-pyrrol-2-yl)methylene]-2H-indol-2-one, (Z)-1,3-Dihydro-5-fluoro-4-iodo-3-[(3-methoxy-1H-pyrrol-2-yl)methylene]-2H-indol-2-one, (Z)-4-Bromo-1,3-dihydro-3-[(3-methoxy-1H-pyrrol-2-yl)methylene]-5-nitro-2H-indol-2-one, (Z)-1,3-Dihydro-4-iodo-3-[(3-methoxy-1H-pyrrol-2-yl)methylene]-5-nitro-2H-indol-2-one, 1,3-Dihydro-5-fluoro-4-iodo-2H-indol-2-one, 1,3-Dihydro-4-iodo-5-nitro-2H-indol-2-one, and 4-Bromo-1,3-dihydro-5-nitro-2H-indol-2-one.

The compounds disclosed herein and covered by the above formulae may exhibit tautomerism or structural isomerism. It is intended that the invention encompasses any tautomeric or structural isomeric form of these compounds, or mixtures of such forms, and is not limited to any one tautomeric or structural isomeric form utilized within the formulae drawn above.

Synthesis of Compounds According to the Invention

The compounds of the invention may be prepared by processes known in the art. Suitable processes for synthesizing these compounds are provided in the examples. Generally, these compounds may be prepared according to the following synthesis scheme:

General Step 1

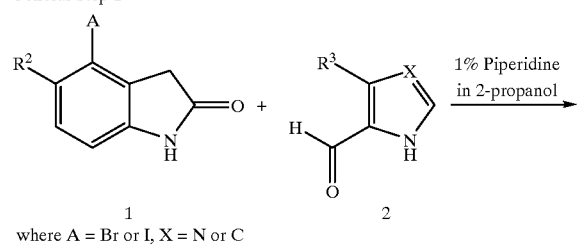

General Step 2

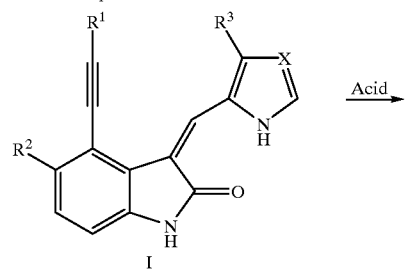

General Step 3

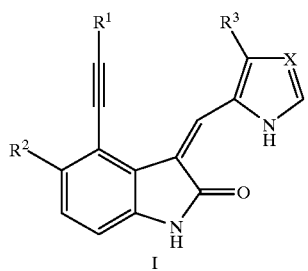

General Step 4

-continued

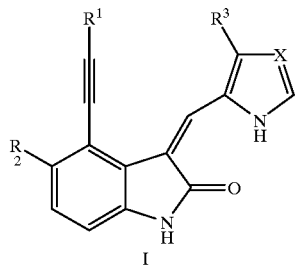

I

General Step 4b

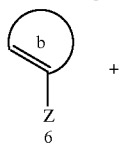

+

Z
6

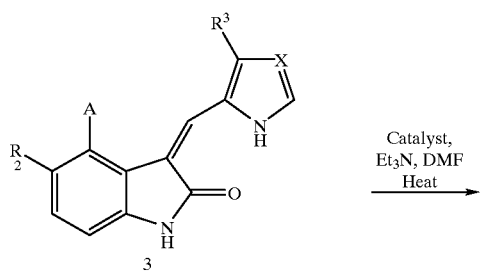

3 where A = Br or I, X = N or C, Z = H, B(OR$^9$)$_2$, or SnBu$_3$

Catalyst,
Et$_3$N, DMF
Heat

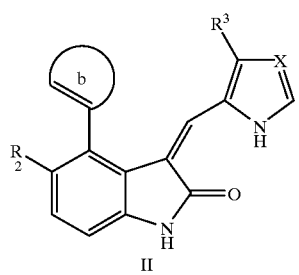

II

Compounds 1, 2, 4, 5 and 6 are either available from commercial sources or are synthesized by methods known in the art.

Compositions/Formulations

In an alternative embodiment, the present invention is directed to pharmaceutical compositions comprising at least one compound of formula I or formula II or a prodrug thereof, or a pharmaceutically acceptable salt of a compound of formula I or formula II or a prodrug of such compound.

These pharmaceutical compositions can be administered orally, for example, in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I or formula II, prodrugs of such compounds, or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I or II.

Dosages

As mentioned above, the compounds of the present invention are useful in the treatment or control of cell proliferative disorders, in particular oncological disorders. These compounds and formulations containing said compounds are particularly useful in the treatment or control of solid tumors, such as, for example, breast and colon tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and will be adjusted to the individual requirements in each particular case. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The compounds of the present invention may be synthesized according to known techniques, such as for example the general scheme provided above. The following examples illustrate preferred methods for synthesizing the compounds and formulations of the present invention.

Example 1

General Synthesis Steps and Starting Materials
Method A: Preparation of 1-alkyl-2-propyn-1-ols via Grignard Addition to Aldehydes

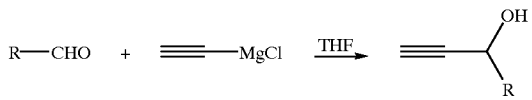

A solution of the appropriate aldehyde (4.0 mmol) in 30 mL dry tetrahydrofuran, under argon, was cooled to 0° C. with an ice bath. Ethynylmagnesium chloride (5 mmol, 0.5 M solution in THF) was added dropwise, and the solution was stirred at 0° C. or room temperature for 1 to 3 h. The reaction was quenched by the addition of a saturated ammonium chloride solution in water (15 mL), and the tetrahydrofuran was evaporated in vacuo. The residue was then extracted with ethyl acetate (3×30 mL), and the combined organic extracts were dried over magnesium sulfate, and concentrated in vacuo to yield the desired propargyl alcohol which was used in the coupling reaction without further purification.

Method B: Preparation of 1-alkyl-2-propyn-1-ols via Grignard Addition to Aldehydes

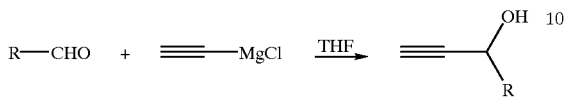

A solution of the appropriate aldehyde (4.0 mmol) in 30 mL dry tetrahydrofuran, under argon, was cooled to 0° C. with an ice bath. Ethynylmagnesium chloride (10 mmol, 0.5 M solution in THF) was added dropwise, and the solution was stirred at 0° C. or room temperature for 1 to 3 h. The reaction was quenched by the addition of a saturated ammonium chloride solution in water (15 mL), and the tetrahydrofuran was evaporated in vacuo. The residue was then extracted with ethyl acetate (3×30 mL), and the combined organic extracts were dried over magnesium sulfate, and concentrated in vacuo to yield the desired propargyl alcohol which was used in the coupling reaction without further purification.

Method C: Preparation of 4-alkynyloxindoles via Palladium (0)-mediated Coupling

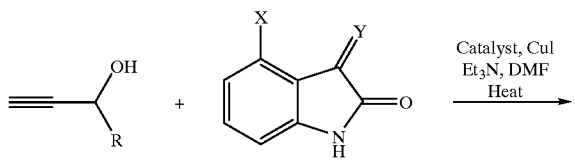

(where X = I)

A solution of the appropriate 4-iodooxindole (4 mmol), and the appropriate alkyne (4.4 mmol) in 3 mL dimethylformamide and 3 mL triethylamine was degassed by bubbling argon through the solution for 15 minutes. At this time copper (I) iodide (16 mg, 0.1 mmol) and palladium catalyst (0.04 mmol) were added, and the reaction was heated, under argon, at between 60 to 90° C. for 6 to 96 hours. After cooling, water (20 mL) was added and the precipitate was filtered off and dried. The product was purified via either flash column chromatography (SiO₂, 230–400 mesh with ethyl acetate/hexanes as solvent) or with reverse phase HPLC (using ether acetonitrile/water or acetonitrile/water/trifluoroacetic acid as solvent).

Method D: Preparation of 4-alkynyloxindoles via Palladium (0)-mediated Coupling

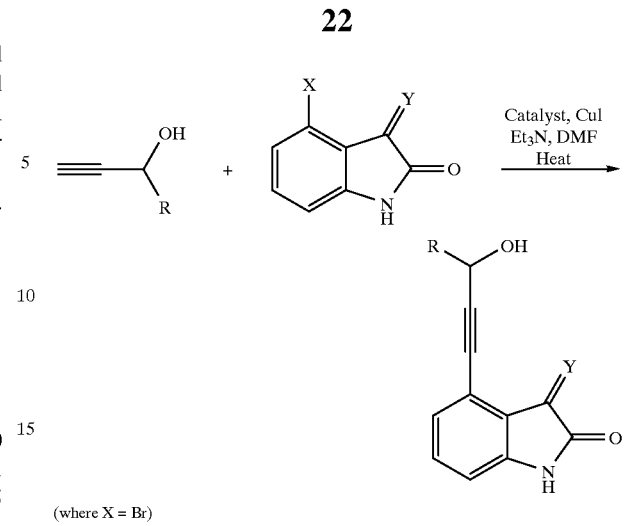

(where X = Br)

A solution of the appropriate 4-bromooxindole (4 mmol), and the appropriate alkyne (4.4 mmol) in 3 mL dimethylformamide and 3 mL triethylamine was degassed by bubbling argon through the solution for 15 minutes. At this time copper (I) iodide (16 mg, 0.1 mmol) and palladium catalyst (0.04 mmol) were added, and the reaction was heated, under argon, at between 60 to 90° C. for 6 to 96 hours. After cooling, water (20 mL) was added and the precipitate was filtered off and dried. The product was purified via either flash column chromatography (SiO₂, 230–400 mesh with ethyl acetate/hexanes as solvent) or with reverse phase HPLC (using ether acetonitrile/water or acetonitrile/water/trifluoroacetic acid as solvent).

Method E: Preparation of Methyl Esters from Carboxylic Acids

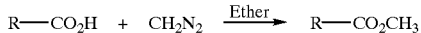

To a solution of the appropriate carboxylic acid (15.3 mmol) in diethyl ether (30 mL) was added a solution of diazomethane (20 mmol, 0.47 M in ether). The reaction was stirred at room temperature for 1 hour at which time a few drops of acetic acid were added. The solution was washed with saturated sodium bicarbonate (3×25 mL) and the solvent was evaporated to yield the desired methyl ester which was used without further purification.

Method F: Preparation of Carboxylic Acids from the Methyl Ester

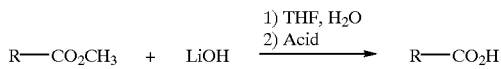

The appropriate methyl ester (0.14 mmol) was dissolved in a mixture of 2 mL tetrahydrofuran and 2 mL water. Lithium hydroxide (2.8 mmol, 20 equiv.) was added, and the reaction was stirred at room temperature for 1 to 24 hours. The tetrahydrofuran was evaporated and 10 mL water was added. The aqueous layer was extracted with ethyl acetate (2×10 mL) and the aqueous layer was then acidified to pH=2 with 1 N hydrochloric acid. The aqueous layer was extracted with ethyl acetate (4×20 mL), and the combined organic extracts were washed with a saturated solution of sodium chloride and were then dried over magnesium sulfate. The ethyl acetate was then evaporated and the product was recrystallized from ethanol.

Method G: Preparation of Carboxamides from Carboxylic Acids

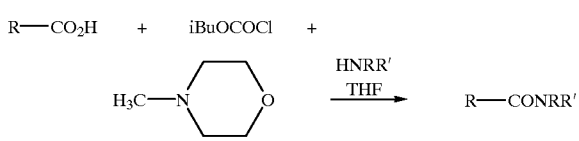

Carboxylic acid (5.1 mmol) was dissolved in 20 mL dry THF under argon, at which time N-methylmorpholine (7.6 mmol, 0.84 mL) was added followed by iso-butyl chloroformate (7.6 mmol, 0.99 mL). The reaction was stirred at room temperature for 30 minutes, and ammonia gas was then bubbled through the reaction mixture for 5 minutes or the appropriate amine was added. The reaction was then stirred at room temperature for 20 minutes to 24 hours, and was then quenched by the addition of water (10 mL). The tetrahydrofuran was then evaporated and the aqueous layer was extracted with ethyl acetate (3×30 mL) to yield the carboxamide as a white crystalline solid which was coupled without further purification.

Method I: Preparation of (Z)-1,3-dihydro-4-(4-hydroxy-1-butynyl)-3-[(3-methoxy-1H-pyrrol-2-yl)methylene]-2H-indol-2-one and (Z)-1,3-dihydro-4-(5-hydroxy-1-pentynyl)-3-[(3-methoxy-1H-pyrrol-2-yl)methylene]-2H-indol-2-one

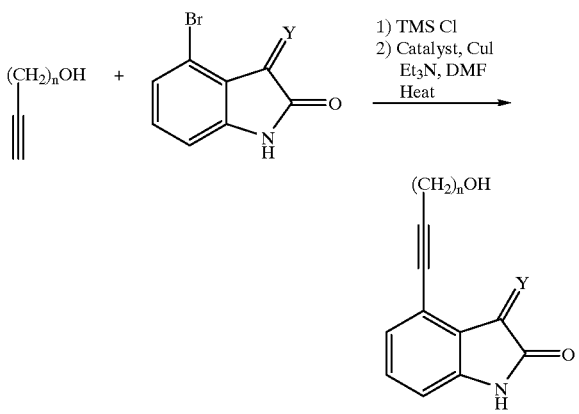

n = 2 or 3

To a solution of the appropriate alkynol (0.57 mmol) in N,N'-dimethylformamide (20 mL) and triethylamine (10 mL), under argon, was added chlorotrimethylsilane (1.0 mmol). The reaction was stirred at room temperature for 1 hour, after which time the bromooxindole (0.38 mmol) was added, and the reaction mixture was degassed by bubbling argon through the solution for 15 minutes. Copper (I) iodide (0.038 mmol) and dichlorobis(triphenylphosphine)palladium(II) (0.019 mmol) were added, and the reaction was heated at 70° C. for 12 hours. Hydrochloric acid (1N, 5 mL) was then added and the reaction was stirred for 15 minutes. An additional 15 mL of water was added and the precipitate was filtered off and dried. The product was purified via flash column chromatography (SiO$_2$, 230–400 mesh) with ethyl acetate/hexanes to yield a yellow powder which was recrystallized from ethyl acetate/hexanes.

Method K: Hydrolysis of Trimethylsilyl Alkyne to Alkyne

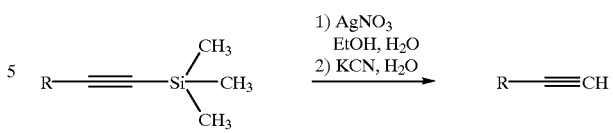

To a solution of the appropriate trimethylsilyl alkyne (4 mmol) in EtOH (80 mL), with addition of THF until complete dissolution if necessary, was added dropwise a solution of AgNO$_3$ (1.46 g, 8.59 mmol) in EtOH (5 mL) and water (15 mL). The mixture was stirred at room temperature for 1 h, then treated with a solution of KCN (2.71 g 41.6 mmol) in water (10 mL). After stirring for an additional 20 min, the reaction mixture was diluted with water (100 mL) and extracted with EtOAc (3×100 mL). Combined EtOAc layers was dried (MgSO$_4$) and concentrated to dryness under reduced pressure to give the desired product.

Method L:

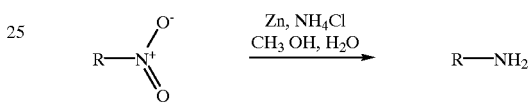

To a solution of nitro compound in 10% water in methanol was added Zn dust and NH$_4$Cl. The mixture was heated at reflux for 6 h then filtered through Celite®. Filtrate was concentrated in vacuo. The product was purified via either flash column chromatography (SiO$_2$, 230–400 mesh with ethyl acetate/hexanes as solvent) or with reverse phase HPLC (using ether acetonitrile/water or acetonitrile/water/trifluoroacetic acid as solvent).

Method M:

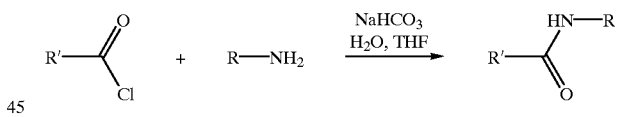

To a mixture of amino compound in THF and saturated aqueous NaHCO$_3$ was added a THF solution of the acid chloride dropwise. The mixture was stirred for 1 to 10 days at room temperature then diluted with ethyl acetate. The phases were separated and the organic solution was washed with water then dried (MgSO$_4$). The product was purified via either flash column chromatography (SiO$_2$, 230–400 mesh with ethyl acetate/hexanes as solvent) or with reverse phase HPLC (using ether acetonitrile/water or acetonitrile/water/trifluoroacetic acid as solvent).

Method N: Preparation of 3-arylmethylene-substituted Oxindoles via Coupling with Aldehyde

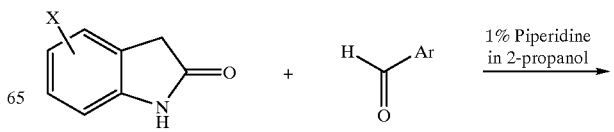

-continued

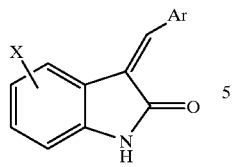

A solution or suspension of the appropriate oxindole (1 mmol), and excess aldehyde (1 to 2 mmol) in 2 mL of 1% piperidine in 2-propanol was heated at between 60 to 90° C. for 1 to 24 hours. Hot water (2 mL) was added. On cooling, the crystallized or precipitated product was filtered off, washed with aqueous 2-propanol and dried.

Method X: Procedure for Converting Aldehydes to Alkynes

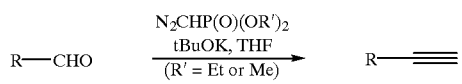

To a slurry of potassium tert-butoxide at −78° C. under argon in 60 mL of THF was added diazomethyl-phosphonic-acid-diethylester or diazomethyl-phosphonic-acid-dimethylester. The aldehyde to be alkynylated was added to this mixture as a solution in a small volume of THF. The resulting solution was stirred for 7 hrs and then poured into a mixture of $Et_2O$ and $H_2O$. The aqueous layer was extracted with $Et_2O$ and the combined organic layer was dried over $Na_2SO_4$ and concentrated. The desired alkyne product was obtained after silica gel column chromatography. (Procedure of J. C. Gilbert, et al., *J. Org. Chem.* 1979, 44, 4997–4998.)

The diazomethyl-phosphonic acid diethyl ester was prepared according to the procedure of M. Regitz, et al., *Liebigs Ann. Chem.* 1971, 748, 207–210.

The diazomethyl-phosphonic acid dimethyl ester was prepared according to the procedure of S. Ohira, *Syn. Comm.* 1989, 19, 561.

Method Y: General Procedure for the N-alkylation of N-Boc Alkynes

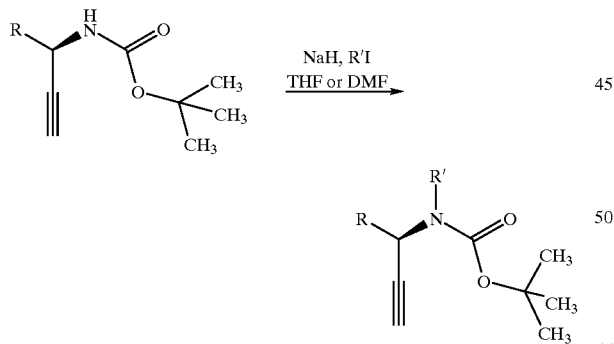

To a solution of N-Boc alkyne in THF or DMF was added NaH at between 0° C. to room temperature and then after vigorous stirring for 2 to 60 min it was added the appropriate alkyl iodide. The mixture was stirred from an hour to overnight and then concentrated. Subsequently, $CH_2Cl_2$ was added and the resulting slurry was filtered. The filtrate was concentrated. Alternatively the reaction mixture was poured into aqueous ammonium chloride solution and extracted with $CH_2Cl_2$. The organic layer was dried over $Na_2SO_4$ and concentrated. The desired product was isolated after silica gel column chromatography.

Starting Materials
Starting Material 1: (Z)-4-Bromo-1,3-dihydro-3-[(3-methoxy-1H-pyrrol-2-yl)methylene]-2H-indol-2-one

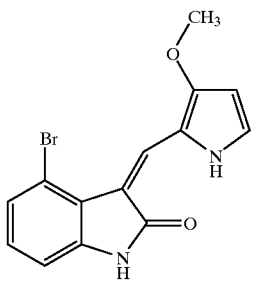

A mixture of 4-bromo-1,3-dihydro-2H-indol-2-one (100 mg, 0.47 mmol) (see Kosuge et al., *Chem. Pharm. Bull.* 33(4):1414–1418 (1985)) and excess 3-methoxy-2-pyrrolecarboxyaldehyde (70.8 mg, 0.57 mmol) (see Bellamy et al., *J. Chem. Research* (S), 18–19 (1979) and *Chem. Research* (M) 0101–0116 (1979)) in 1% piparidine in 2-propanol (1 mL) was heated at 85° C. for 2 h. Hot water (1 mL) was added. On cooling, the crystallized product was filtered off, washed with aqueous 2-propanol and dried. (Yield 0.13 g, 83%).

Starting Material 2: (Z)-1,3-Dihydro-4-iodo-3-[(3-methoxy-1H-pyrrol-2-yl)methylene]-2H-indol-2-one

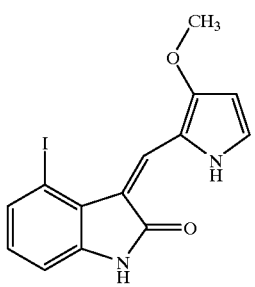

A mixture of 1,3-dihydro-4-iodo-2H-indol-2-one (0.51 g, 1.97 mmol) (prepared according to T. Fukuyama et al., *J. Am. Chem. Soc.* 118:7426–7427 (1996)), and excess 3-methoxy-2-pyrrolecarboxyaldehyde (0.30 g, 2.36 mmol) (prepared according to F. Bellamy et al., supra) in 1% piperidine in 2-propanol (10 mL) was heated at 85° C. for 4 h. Hot water (10 mL) was added. On cooling, the crystallized product was filtered off, washed with aqueous 2-propanol and dried. (Yield 0.46 g, 64%).

Starting Material 3: (Z)-1,3-Dihydro-5-fluoro-4-iodo-3-[(4-methyl-1H-imidazol-5-yl)methylene]-2H-indol-2-one

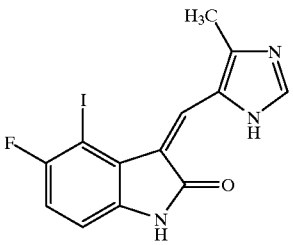

A mixture of 1,3-dihydro-5-fluoro-4-iodo-2H-indol-2-one (0.48 g, 1.7 mmol) (see Example 2A infra), and excess 4-methyl-5-imidazolecarboxaldehyde (0.40 g, 3.6 mmol)

(Aldrich) in 1% piperidine in 2-propanol (10 mL) was heated at 90° C. for 4 h. Hot water (10 mL) was added. On cooling, the crystallized product was filtered off, washed with aqueous 2-propanol and dried. The residue was purified by reverse phase chromatography using trifluoroacetic acid-acetonitrite-water as solvent to give product as trifluoroacetate salt. (Yield 0.64 g, 100%)

Starting Material 4: (Z)-1,3-Dihydro-4-iodo-3-[(4-methyl-1H-imidazol-5-yl)methylene]-5-nitro-2H-indol-2-one

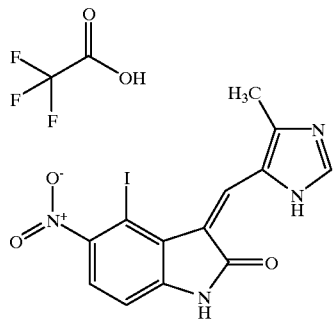

A mixture of 1,3-dihydro-4-iodo-5-nitro-2H-indol-2-one (0.41 g, 1.35 mmol) (see Example 2B infra), and excess 4-methyl-5-imidazolecarboxaldehyde (0.18 g, 1.62 mmol) (Aldrich) in 1% piperidine in 2-propanol (10 mL) was heated at 80° C. for 4 h. Hot water (10 mL) was added. On cooling, the crystallized product was filtered off, washed with aqueous 2-propanol and dried. The residue purifired by reverse phase chromatography using trifluoroacetic acid-acetonitrile-water as solvent to give product as trifluoroacetate salt. (Yield 0.31 g, 58%).

Starting Material 5: (Z)-1,3-Dihydro-5-fluoro-4-iodo-3-[(1H-pyrrol-2-yl)methylene]-2H-indol-2-one

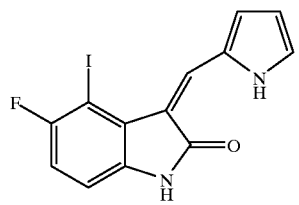

A mixture of 1,3-dihydro-5-fluoro-4-iodo-2H-indol-2-one (1.40 g, 5.05 mmol) (see Example 2A infra), and excess 2-pyrrolecarboxyaldehyde (0.60 g, 6.3 mmol) (Aldrich) in 1% piperidine in 2-propanol (20 mL) was heated at 85° C. for 2.25 h. Hot water (20 mL) was added. On cooling, the crystallized product was filtered off, washed with aqueous 2-propanol and dried. (Yield 1.50 g, 84%).

Starting Material 6: (Z)-1,3-Dihydro-5-fluoro-4-iodo-3-[(3-methoxy-1H-pyrrol-2-yl)methylene]-2H-indol-2-one

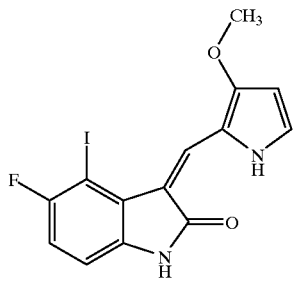

A mixture of 1,3-dihydro-5-fluoro-4-iodo-2H-indol-2-one (0.96 g, 3.47 mmol) (see Example 2A infra), and excess 3-methoxy-2-pyrrolecarboxyaldehyde (0.52 g, 4.16 mmol) (see Bellamy et al., *J. Chem. Research* (S), 18–19 (1979); *J. Chem. Research* (M), 0101–0116 (1979)) in 1% piperidine in 2-propanol (15 mL) was heated at 85° C. for 3 h. Hot water (15 mL) was added. On cooling, the crystallized product was filtered off, washed with aqueous 2-propanol and dried. (Yield 1.24 g, 93%).

Starting Material 7: (Z)-4-Bromo-1,3-dihydro-3-[(3-methoxy-1H-pyrrol-2-yl)methylene]-5-nitro-2H-indol-2-one

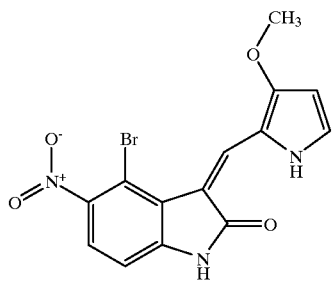

A mixture of 4-bromo-1,3-dihydro-5-nitro-2H-indol-2-one (0.113 g, 0.44 mmol) (see Example 2C infra), and excess 3-methoxy-2-pyrrolecarboxyaldehyde (66.3 mg, 0.53 mmol) (see Bellamy et al., *J. Chem. Research* (S), 18–19 (1979); *J. Chem. Research* (M), 0101–0116 (1979)) in 1% piperidine in 2-propanol (2 mL) was heated at 85° C. for 3 h. Hot water (2 mL) was added. On cooling, the crystallized product was filtered off, washed with aqueous 2-propanol and dried. (Yield 0.136 g, 85%).

Example 2

A. Synthesis of 1,3-Dihydro-5-fluoro-4-iodo-2H-indol-2-one

29
-continued

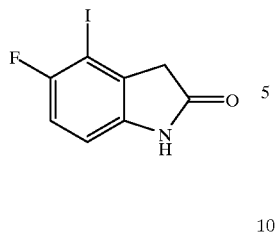

A suspension of 1,3-dihydro-1-hydroxy-4-iodo-2H-indol-2-one, (2.43 g, 9 mmol) (see below) in dry dichloromethane (500 mL) was cooled to −25° C. under an argon atmosphere with magnetic stirring. A solution of (diethylamino)sulfur trifluoride (DAST, 1.35 mL) (Aldrich) in dry dichloromethane (40 mL) was added dropwise at such a rate that the reaction temperature did not rise above −25° C. (about 15 min.). After stirring for an additional 30 min. at −25° C., the reaction was quenched by the addition of saturated aqueous sodium bicarbonate solution (180 mL) and allowed to warm to room temperature. The mixture was then filtered through Celite® (Fisher Scientific) and the layers separated. The aqueous layer was extracted with dichloromethane (2×300 mL). The dichloromethane layers were washed with saturated aqueous sodium chloride solution (200 mL), combined, dried (magnesium sulfate) and concentrated. Residue was purified by flash chromatography on sitics get using ethyl acetate-dichloromethane (1:7, V/V) as solvent to give 1,3-dihydro-5-fluoro-4-iodo-2H-indol-2-one. (Yield 1.08 g, 43%).

The 1,3-dihydro-1-hydroxy-4-iodo-2H-indol-2-one was prepared according to the procedure of A. S. Kende et al., "Synthesis of 1-Hydroxyoxindoles," *Synth. Commun.*, 20(14):2133–2138 (1990).

B. Synthesis of 1,3-Dihydro-4-iodo-5-nitro-2H-indol-2-one

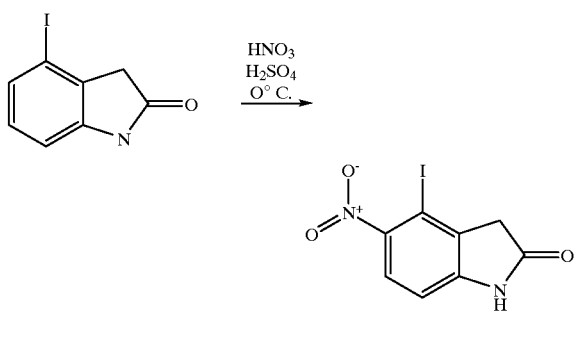

A mixture of concentrated sulfuric acid (0.73 mL) and concentrated nitric acid (0.14 mL) was added slowly to a solution of 1,3-dihydro-4-iodo-2H-indol-2-one (0.5 g, 1.93 mmol) (see T. Fukuyama, supra, and Kende, supra) in concentrated sulfuric acid (6 mL) at −5° C. with stirring. The mixture was stirred for an additional 15 min at −5° C. then poured into ice. After standing for 1 h, solid was collected by filtration and washed with water, and dried in a vacuum oven to give 1,3-dihydro-4-iodo-5-nitro-2H-indol-2-one. (Yield 0.46 g, 78%).

C. Synthesis of 4-Bromo-1,3-dihydro-5-nitro-2H-indol-2-one

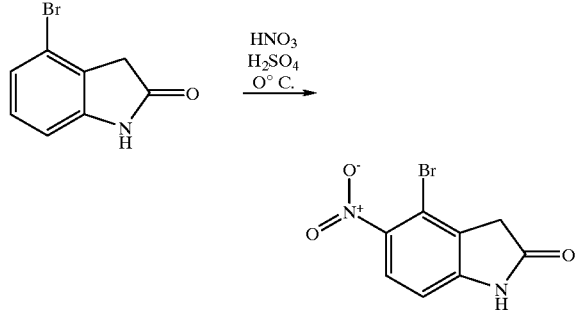

A mixture of concentrated sulfuric acid (3.6 mL) and concentrated nitric acid (0.7 mL) was added slowly to a solution of 4-bromo-1,3-dihydro-2H-indol-2-one (2 g, 9.48 mmol) (see below) in concentrated sulfuric acid (20 mL) at −5° C. with stirring. The mixture was stirred for an additional 1 h at −5° C. then poured in ice. After standing for 1 h, precipitate formed was collected by filtration and washed with water, and dried in a vacuum oven to give 4-bromo-1,3-dihydro-5-nitro-2H-indol-2-one. (Yield 2.33 g, 96%).

The 4-bromo-1,3-dihydro-2H-indol-2-one was prepared according to the procedure of T. Kosuge et al., "Synthesis and Some Reactions of 6-Bromooxindole," *Chem. Pharm. Bull*, 33(4):1414–1418 (1985).

Example 3

(Z)-1,3-Dihydro-4-(6-hydroxy-1-hexynyl)-3-[(3-methoxy-1H-pyrrol-2-yl)methylene]-2H-indol-2-one (A)

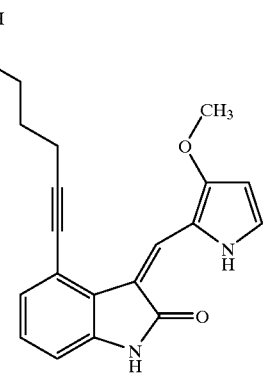

Using general Method D above, 5-hexyn-1-ol (56 mg, 0.57 mmol) (Aldrich) was coupled with (Z)-4-bromo-1,3-dihydro-3-[(3-methoxy-1H-pyrrol-2-yl)methylene]-2H-indol-2-one (110 mg, 0.38 mmol) (Starting Material 1 supra) using (Ph₃P)₂PdCl₂ (13 mg) (Aldrich) and CuI (7 mg) (Aldrich) as catalyst in DMF (3 mL) and Et₃N (3 mL) as solvent at 70° C. for 14 h to yield (Z)-1,3-dihydro-4-(6-hydroxy-1-hexynyl)-3-[(3-methoxy-1H-pyrrol-2-yl)methylene]-2H-indol-2-one.

Example 4

(Z)-1,3-Dihydro-4-(5-hydroxy-1-pentynyl)-3-[(3-methoxy-1H-pyrrol-2-yl)methylene]-2H-indol-2-one (B)

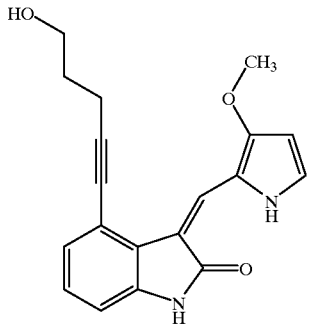

Using Method I above, 4-pentyn-1-ol (40 mg, 0.57 mmol) (Aldrich) was dissolved, under argon, in 3 mL DMF and 2 mL triethylamine, and to this solution was added chlorotrimethylsilane (0.13 mL, 1 mmol) (Aldrich). The reaction was stirred at room temperature for 1 h, at which time (Z)-4-bromo-1,3-dihydro-3-[(3-methoxy-1H-pyrrol-2-yl)methylene]-2H-indol-2-one (110 mg, 0.38 mmol) (Starting Material 1 supra) was added and the solution was degassed for 15 min by bubbling argon through the solution. $(Ph_3P)_2PdCl_2$ (15 mg) (Aldrich) and CuI (7 mg) (Aldrich) were added and the reaction was heated at 70° C. for 14 h. The reaction mixture was then poured into 25 mL 1N HCl and the yellow precipitate was filtered off. The product was purified via flash column chromatography to obtain (Z)-1,3-dihydro-4-(5-hydroxy-1-pentynyl)-3-[(3-methoxy-1H-pyrrol-2-yl)methylene]-2H-indol-2-one as a yellow powder. (Yield 55 mg, 45%).

Example 5

(Z)-1,3-Dihydro-4-(4-hydroxy-1-butynyl)-3-[(3-methoxy-1H-pyrrol-2-yl)methylene]-2H-indol-2-one (C)

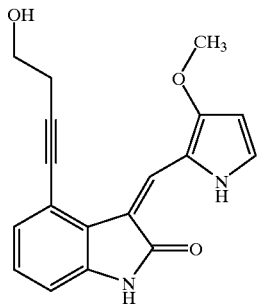

Using Method I above, 3-butyn-1-ol (40 mg, 0.57 mmol) (Aldrich) was dissolved, under argon, in 3 mL DMF and 2 mL triethylamine, and to this solution was added chlorotrimethylsilane (0.13 mL, 1 mmol). The reaction was stirred at room temperature for 1 h, at which time (Z)-4-bromo-1,3-dihydro-3-[(3-methoxy-1H-pyrrol-2-yl)methylene]-2H-indol-2-one (110 mg, 0.38 mmol) (Starting Material 1 supra) was added and the solution was degassed for 15 min by bubbling argon through the solution. $(Ph_3P)_2PdCl_2$ (13 mg) and CuI (7 mg) were added and the reaction was heated at 70° C. for 14 h. The reaction mixture was then poured into 25 mL 1 N HCl and the yellow precipitate was filtered off. The product was purified via flash column chromatography to obtain (Z)-1,3-dihydro-4-(4-hydroxy-1-butynyl)-3-[(3-methoxy-1H-pyrrol-2-yl)methylene]-2H-indol-2-one as a yellow powder. (Yield 35 mg, 30%).

Example 6 rac-(Z)-1,3-Dihydro-4-(3-hydroxy-3-methyl-1-pentynyl)-3-[(3-methoxy-1H-pyrrol-2-yl)methylene]-2H-indol-2-one (D)

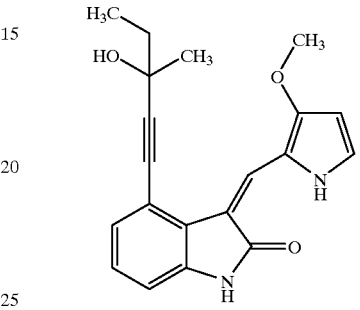

Using Method D above, 3-methyl-1-pentyn-3-ol (75 mg, 0.75 mmol) (Aldrich) was coupled with (Z)-4-bromo-1,3-dihydro-3-[(3-methoxy-1H-pyrrol-2-yl)methylene]-2H-indol-2-one (Starting Material 1 supra) (200 mg, 0.63 mmol) using $(Ph_3P)_2PdCl_2$ (25 mg) and CuI (12 mg) as catalyst in DMF (3 mL) and $Et_3N$ (3 mL) as solvent at 70° C. for 17 h to yield rac-(Z)-1,3-dihydro-4-(3-hydroxy-3-methyl-1-pentynyl)-3-[(3-methoxy-1H-pyrrol-2-yl)methylene]-2H-indol-2-one. (Yield 66 mg, 31%).

Example 7

(Z)-6-[2,3-Dihydro-3-[(3-methoxy-1H-pyrrol-2-yl)methylene]-2-oxo-1H-indol-4-yl]-5-hexynoic acid methyl ester (E)

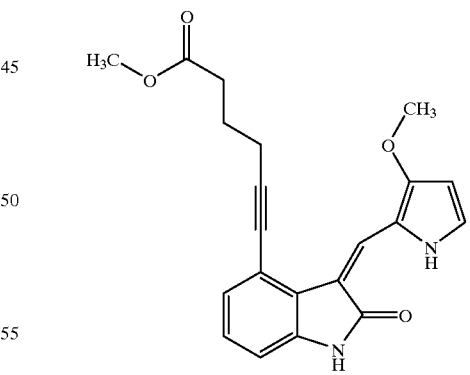

Using Method D above, methyl 5-hexynoate (109 mg, 0.87 mmol) (see below) was coupled with (Z)-4-bromo-1,3-dihydro-3-[(3-methoxy-1H-pyrrol-2-yl)methylene]-2H-indol-2-one (179 mg, 0.62 mmol) (Starting Material 1 supra) using $(Ph_3P)_2PdCl_2$ (30 mg) and CuI (15 mg) as catalyst in DMF (4 mL) and $Et_3N$ (4 mL) as solvent at 70° C. for 15 h to yield (Z)-6-[2,3-dihydro-3-[(3-methoxy-1H-pyrrol-2-yl)methylene]-2-oxo-1H-indol-4-yl]-5-hexynoic acid methyl ester. (Yield 78 mg, 35%).

Example 8

(Z)-5-[2,3-Dihydro-3-[(3-methoxy-1H-pyrrol-2-yl)
methylene]-2-oxo-1H-indol-4-yl]-4-pentynoic acid
methyl ester (F)

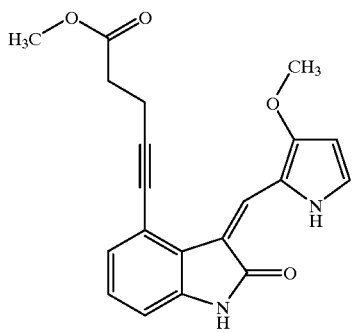

Using Method D above, methyl 4-pentynoate (163 mg, 1.45 mmol) (see below) was coupled with (Z)-4-bromo-1, 3-dihydro-3-[(3-methoxy-1H-pyrrol-2-yl)methylene]-2H-indol-2-one (300 mg, 1.03 mmol) (Starting Material 1 supra) using (Ph$_3$P)$_2$PdCl$_2$ (30 mg) and CuI (15 mg) as catalyst in DMF (5 mL) and Et$_3$N (5 mL) as solvent at 70° C. for 14 h to yield (Z)-5-[2,3-dihydro-3-[(3-methoxy-1H-pyrrol-2-yl) methylene]-2-oxo-1H-indol-4-yl]-4-pentynoic acid methyl ester. (Yield 120 mg, 33%).

The starting material methyl 4-pentynoate was prepared by the reaction of 4-pentynoic acid with diazomethane according to Method E above.

Example 9

(Z)-6-[2,3-Dihydro-3-[(3-methoxy-1H-pyrrol-2-yl)
methylene]-2-oxo-1H-indol-4-yl]-5-hexynoic acid
(G)

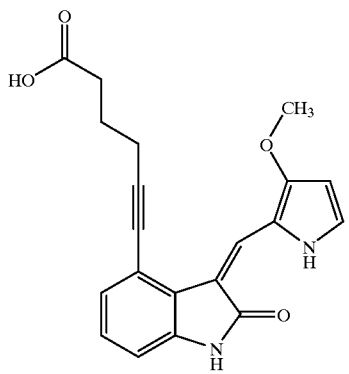

Using Method F above, (Z)-6-[2,3-dihydro-3-[(3-methoxy-1H-pyrrol-2-yl)methylene]-2-oxo-1H-indol-4-yl]-5-hexynoic acid methyl ester (40 mg, 0.11 mmol) (from Example 7 above) was hydrolyzed with LiOH•H$_2$O (92 mg, 2.19 mmol) in THF (3 mL) and water (3 mL) for 22 h yielding (Z)-6-[2,3-dihydro-3-[(3-methoxy-1H-pyrrol-2-yl) methylene]-2-oxo-1H-indol-4-yl]-5-hexynoic acid. (Yield 31 mg, 81%).

The starting material methyl 5-hexynoate was prepared by the reaction of 5-hexynoic acid with diazomethane according to Method E above.

Example 10

(Z)-5-[2,3-Dihydro-3-[(3-methoxy-1H-pyrrol-2-yl)
methylene]-2-oxo-1H-indol-4-yl]-4-pentynoic acid
(H)

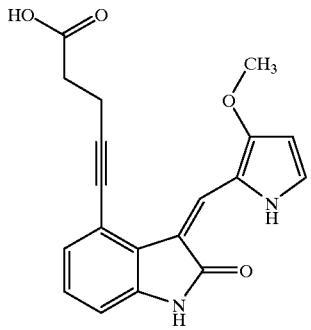

Using Method F above, (Z)-5-[2,3-dihydro-3-[(3-methoxy-1H-pyrrol-2-yl)methylene]-2-oxo-1H-indol-4-yl]-4-pentynoic acid methyl ester (50 mg, 0.14 mmol) (from Example 8 above) was hydrolyzed with LiOH•H$_2$O (118 mg, 2.8 mmol) in THF (3 mL) and water (3 mL) for 22 h. (Yield 40 mg, 85%).

Example 11

(Z)-5-[2,3-Dihydro-3-[(3-methoxy-1H-pyrrol-2-yl)
methylene]-2-oxo-1H-indol-4-yl]-4-pentynoic acid
Sodium salt (I)

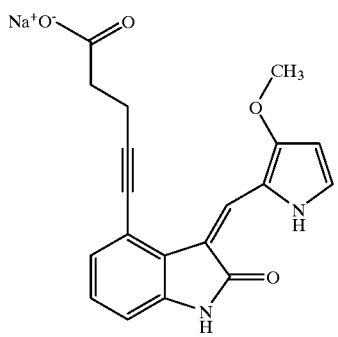

(Z)-5-[2,3-Dihydro-3-[(3-methoxy-1H-pyrrol-2-yl) methylene]-2-oxo-1H-indol-4-yl]-4-pentynoic acid (100 mg, 3 mmol) (from Example 10 above) was dissolved in tetrahydrofuran (1 mL), and 1N sodium hydroxide (3 mL) was added. The resulting product, (Z)-5-[2,3-dihydro-3-[(3-methoxy-1H-pyrrol-2-yl)methylene]-2-oxo-1H-indol-4-yl]-4-pentynoic acid sodium salt, was purified via reverse-phase HPLC (acetonitrile-water over 15 minutes).

Example 12

(Z)-5-[2,3-Dihydro-3-[(3-methoxy-1H-pyrrol-2-yl)methylene]-2-oxo-1H-indol-4-yl]-4-pentynamide (J)

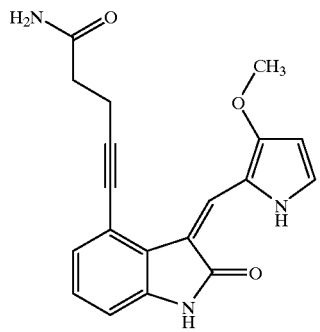

Using Method C above, 4-pentynamide (49 mg, 0.5 mmol) (prepared from 4-pentyonic acid according to Method G above) was coupled with (Z)-1,3-dihydro-4-iodo-3-[(3-methoxy-1H-pyrrol-2-yl)methylene]-2H-indol-2-one (Starting Material 2 supra) (120 mg, 0.32 mmol) using (Ph$_3$P)$_2$PdCl$_2$ (12 mg) and CuI (6 mg) as catalyst in DMF (1 mL) and Et$_3$N (1 mL) as solvent at 70° C. for 22 h to yield (Z)-5-[2,3-dihydro-3-[(3-methoxy-1H-pyrrol-2-yl)methylene]-2-oxo-1H-indol-4-yl]-4-pentynamide. (Yield 45 mg, 42%).

Example 13

(Z)-6-[2,3-Dihydro-3-[(3-methoxy-1H-pyrrol-2-yl)methylene]-2-oxo-1H-indol-4-yl]-5-hexynamide (K)

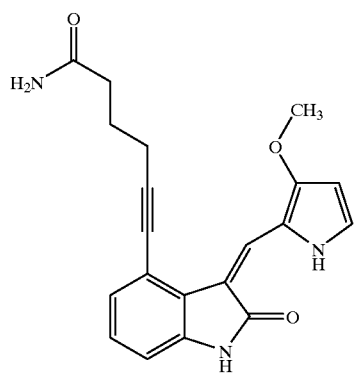

Using Method C above, 5-hexynamide (46 mg, 0.4 mmol) (prepared from 5-hexynoic acid by Method G above) was coupled with (Z)-1,3-dihydro-4-iodo-3-[(3-methoxy-1H-pyrrol-2-yl)methylene]-2H-indol-2-one (Starting Material 2 supra) (113 mg, 0.31 mmol) using (Ph$_3$P)$_2$PdCl$_2$ (12 mg) and CuI (6 mg) as catalyst in DMF (1 mL) and Et$_3$N (1 mL) as solvent at 70° C. for 22 h yielding (Z)-6-[2,3-dihydro-3-[(3-methoxy-1H-pyrrol-2-yl)methylene]-2-oxo-1H-indol-4-yl]-5-hexynamide. (Yield 52 mg, 48%).

Example 14

(Z)-1,3-Dihydro-4-(3-hydroxy-3-methyl-1-butynyl)-3-[(3-methoxy-1H-pyrrol-2-yl)methylene]-2H-indol-2-one (L)

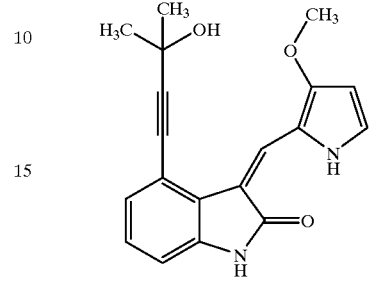

Using Method D above, 3-methyl-1-butyn-3-ol (150 mg, 1.78 mmol) (Aldrich) was coupled with (Z)-4-bromo-1,3-dihydro-3-[(3-methoxy-1H-pyrrol-2-yl)methylene]-2H-indol-2-one (101 mg, 0.32 mmol) (Starting Material 1 supra) using (Ph$_3$P)$_2$PdCl$_2$ (30 mg) and CuI (16 mg) as catalyst in DMF (3 mL) and Et$_3$N (3 mL) as solvent at 70° C. for 18 h to yield (Z)-1,3-dihydro-4-(3-hydroxy-3-methyl-1-butynyl)-3-[(3-methoxy-1H-pyrrol-2-yl)methylene]-2H-indol-2-one. (Yield 43 mg, 38%).

Example 15

(Z)-1,3-Dihydro-4-[(1-hydroxycyclohexyl)ethynyl]-3-[(3-methoxy-1H-pyrrol-2-yl)methylene]-2H-indol-2-one (M)

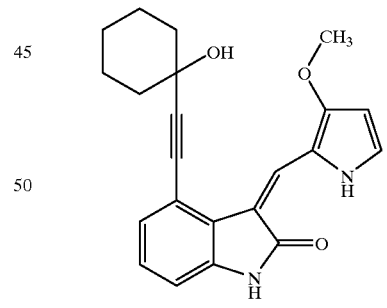

Using Method C above, 1-ethynyl-1-cyclohexanol (60 mg, 0.48 mmol) (Aldrich) was coupled with (Z)-1,3-dihydro-4-iodo-3-[(3-methoxy-1H-pyrrol-2-yl)methylene]-2H-indol-2-one (146 mg, 0.4 mmol) (Starting Material 2 supra) using (Ph$_3$P)$_2$PdCl$_2$ (20 mg) and CuI (10 mg) as catalyst in DMF (2 mL) and Et$_3$N (2 mL) as solvent at 70° C. for 15 h to yield (Z)-1,3-dihydro-4-[(1-hydroxycyclohexyl)ethynyl]-3-[(3-methoxy-1H-pyrrol-2-yl)methylene]-2H-indol-2-one. (Yield 94 mg, 65%).

Example 16 rac-(Z)-1,3-Dihydro-4-(3-hydroxy-3-methyl-1-hexynyl)-3-[(3-methoxy-1H-pyrrol-2-yl)methylene]-2H-indol-2-one (N)

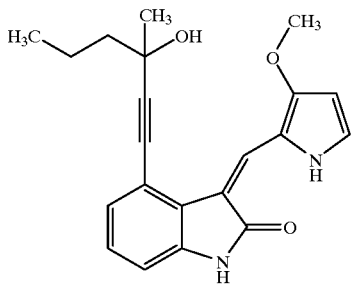

Using Method D above, 3-methyl-1-hexyn-3-ol (98 mg, 0.87 mmol) (Aldrich) was coupled with (Z)-4-bromo-1,3-dihydro-3-[(3-methoxy-1H-pyrrol-2-yl)methylene]-2H-indol-2-one (Starting Material I supra) (127 mg, 0.4 mmol) using $(Ph_3P)_2PdCl_2$ (46 mg) and CuI (22 mg) as catalyst in DMF (3 mL) and $Et_3N$ (3 mL) as solvent at 70° C. for 22 h yielding rac-(Z)-1,3-dihydro-4-(3-hydroxy-3-methyl-1-hexynyl)-3-[(3-methoxy-1H-pyrrol-2-yl)methylene]-2H-indol-2-one. (Yield 92 mg, 66%).

Example 17 rac-(Z)-1,3-Dihydro-4-(3,5-dimethyl-3-hydroxy-1-hexynyl)-3-[(3-methoxy-1H-pyrrol-2-yl)methylene]-2H-indol-2-one (O)

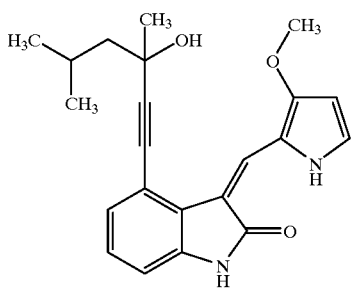

Using Method C above, 3,5-dimethyl-1-hexyn-3-ol (61 mg, 0.48 mmol) (Aldrich) was coupled with (Z)-1,3-dihydro-4-iodo-3-[(3-methoxy-1H-pyrrol-2-yl)methylene]-2H-indol-2-one (Starting Material 2 supra) (146 mg, 0.4 mmol) using $(Ph_3P)_2PdCl_2$ (20 mg) and CuI (10 mg) as catalyst in DMF (2 mL) and $Et_3N$ (2 mL) as solvent at 70° C. for 15 h to yield rac-(Z)-1,3-dihydro-4-(3,5-dimethyl-3-hydroxy-1-hexynyl)-3-[(3-methoxy-1H-pyrrol-2-yl)methylene]-2H-indol-2-one. (Yield 87 mg, 60%).

Example 18

(R)-(Z)-1,3-Dihydro-4(3-hydroxy-1-octynyl)-3-[(3-methoxy-1H-pyrrol-2-yl)methylene]-2H-indol-2-one (P)

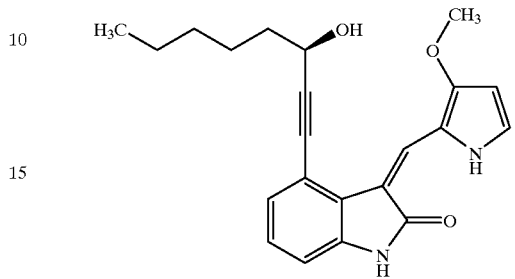

Using Method C above, (R)-(+)-1-octyn-3-ol (61 mg, 0.48 mmol) (Aldrich) was coupled with (Z)-1,3-dihydro-4-iodo-3-[(3-methoxy-1H-pyrrol-2-yl)methylene]-2H-indol-2-one (146 mg, 0.4 mmol) (Starting Material 2 supra) using $(Ph_3P)_2PdCl_2$ (20 mg) and CuI (10 mg) as catalyst in DMF (2 mL) and $Et_3N$ (2 mL) as solvent at 70° C. for 15 h to yield (R)-(Z)-1,3-dihydro-4-(3-hydroxy-1-octynyl)-3-[(3-methoxy-1H-pyrrol-2-yl)methylene]-2H-indol-2-one. (Yield 91 mg, 62%).

Example 19 rac-(Z)-1,3-Dihydro-4-(3-hydroxy-1-octynyl)-3-[(3-methoxy-1H-pyrrol-2-yl)methylene]-2H-indol-2-one (Q)

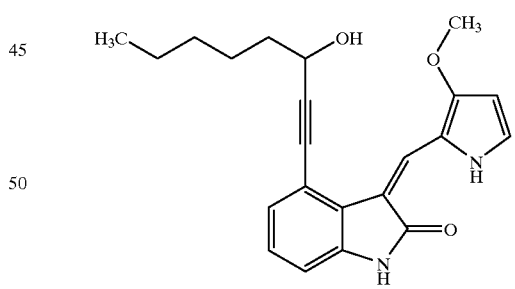

Using Method C above, rac-1-octyn-3-ol (61 mg, 0.48 mmol) (Aldrich) was coupled with (Z)-1,3-dihydro-4-iodo-3-[(3-methoxy-1H-pyrrol-2-yl)methylene]-2H-indol-2-one (146 mg, 0.4 mmol) (Starting Material 2 supra) using $(Ph_3P)_2PdCl_2$ (20 mg) and CuI (10 mg) as catalyst in DMF (2 mL) and $Et_3N$ (2 mL) as solvent at 70° C. for 15 h to yield rac-(Z)-1,3-dihydro-4-(3-hydroxy-1-octynyl)-3-[(3-methoxy-1H-pyrrol-2-yl)methylene]-2H-indol-2-one. (Yield 88 mg, 60%).

Example 20 rac-(Z)-1,3-Dihydro-4-(3-hydroxy-1-pentynyl)-3-[(3-methoxy-1H-pyrrol-2-yl)methylene]-2H-indol-2-one (R)

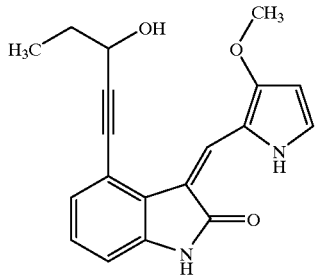

Using Method C above, 1-pentyn-3-ol (40 mg, 0.48 mmol) (Aldrich) was coupled with (Z)-1,3-dihydro-4-iodo-3-[(3-methoxy-1H-pyrrol-2-yl)methylene]-2H-indol-2-one (146 mg, 0.4 mmol) (Starting Material 2 supra) using $(Ph_3P)_2PdCl_2$ (20 mg) and CuI (10 mg) as catalyst in DMF (2 mL) and $Et_3N$ (2 mL) as solvent at 70° C. for 15 h to yield rac-(Z)-1,3-dihydro-4-(3-hydroxy-1-pentynyl)-3-[(3methoxy-1H-pyrrol-2-yl)methylene]-2H-indol-2-one. (Yield 78 mg, 60%).

Example 21

3-(2-Hydroxyethoxy)-1-propyne

Sodium metal (2.3 g, 0.1 mol) was added to 60 mL ethylene glycol over a period of 4 h. Propargyl bromide (80% solution in toluene, 11.1 mL, 0.1 mol) (Aldrich) was then added dropwise over a period of 2.5 h while maintaining the reaction temperature at 30–40° C. When the addition was complete, the reaction mixture was heated to 70–80° C. for 1.5 h. The reaction mixture was then cooled, and added to 50 mL water and 40 mL diethyl ether. The phases were separated, and the aqueous layer was extracted with diethyl ether (4×15 mL). The combined organic extracts were dried over magnesium sulfate and concentrated in vacuo to yield 3-(2-hydroxyethoxy)-1-propyne.

Example 22

(Z)-1,3-Dihydro-4-[3-(2-hydroxyethoxy)-1-propynyl]-3-[(3-methoxy-1H-pyrrol-2-yl)methylene]-2H-indol-2-one (S)

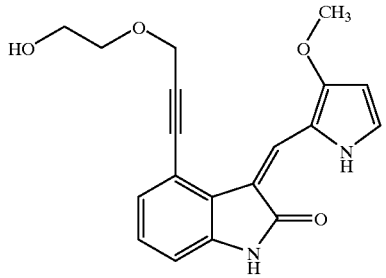

Using Method C above, 3-(2-hydroxyethoxy)-1-propyne (53 mg, 0.53 mmol) (from Example 21 above) was coupled with (Z)-1,3-dihydro-4-iodo-3-[(3-methoxy-1H-pyrrol-2-yl)methylene]-2H-indol-2-one (150 mg, 0.41 mmol) (Starting Material 2 supra) using $(Ph_3P)_2PdCl_2$ (20 mg) and CuI (10 mg) as catalyst in DMF (2 mL) and $Et_3N$ (2 mL) as solvent at 70° C. for 18 h to yield (Z)-1,3-dihydro-4-[3-(2-hydroxyethoxy)-1-propynyl]-3-[(3-methoxy-1H-pyrrol-2-yl)methylene]-2H-indol-2-one. (Yield 68 mg, 49%).

Example 23 rac-3-[(2,2-Dimethyl-1,3-dioxolan-4-yl)methoxy]-1-propyne

Sodium hydride (1.32 g, 55 mmol) was added to a solution of 2,2-dimethyl-1,3-dioxotane-4-methanol (Aldrich) in THF (60 mL), and the resulting mixture was heated at reflux for 90 min then cooled to 0° C. Tetrabutylammonium iodide (370 mg), and propargyl bromide (80% in toluene, 6.22 mL, 50 mmol) (Aldrich) were added successively. After stirring for 150 min. at room temperature, 20 mL water was added and the THF was evaporated in vacuo. The aqueous layer was then extracted with diethyl ether (4×50 mL), and the combined organic layers were dried over magnesium sulfate and concentrated in vacuo to yield rac-3-[(2,2-dimethyl-1,3-dioxotan-4-yl)methoxy]-1-propyne.

Example 24 rac-(Z)-4-[3-[(2,2-dimethyl-1,3-dioxolan-4-yl)methoxy]-1-propynyl]-1,3-dihydro-3-[(3-methoxy-1H-pyrrol-2-yl)methylene]-2H-indol-2-one (T)

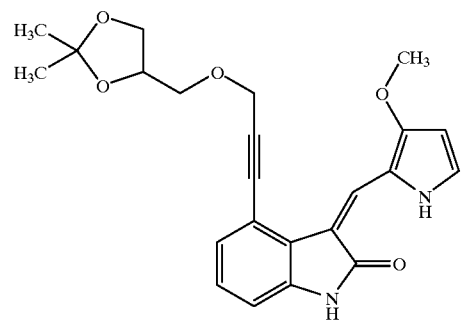

Using Method C above, 3-[(2,2-dimethyl-1,3-dioxolan-4-yl)methoxy]-1-propyne (90 mg, 0.53 mmol) (from Example 23 above) was coupled with (Z)-1,3-dihydro-4-iodo-3-[(3-methoxy-1H-pyrrol-2-yl)methylene]-2H-indol-2-one (Starting Material 2 supra) (150 mg, 0.41 mmol) using $(Ph_3P)_2PdCl_2$ (20 mg) and CuI (10 mg) as catalyst in DMF (2 mL) and $Et_3N$ (2 mL) as solvent at 70° C. for 18 h to rac-(Z)-4-[3-[(2,2-dimethyl-1,3-dioxolan-4-yl)methoxy]-1-propynyl]-1,3-dihydro-3-[(3-methoxy-1H-pyrrol-2-yl)methylene]-2H-indol-2-one. (Yield 97 mg, 58%).

Example 25

(S)-(Z)-1,3-Dihydro-4-(3-hydroxy-1-octynyl)-3-[(3-methoxy-1H-pyrrol-2-yl)methylene]-2H-indol-2-one (U)

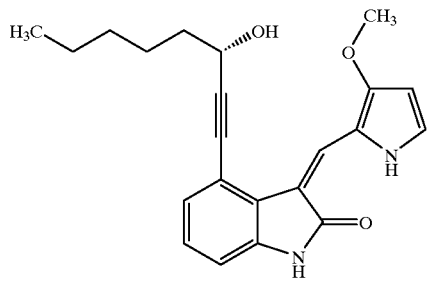

Using Method C above, (S)-(−)-1-octyn-3-ol (61 mg, 0.53 mmol) (Aldrich) was coupled with (Z)-1,3-dihydro-4-iodo-3-[(3-methoxy-1H-pyrrol-2-yl)methylene]-2H-indol-2-one (150 mg, 0.41 mmol) (Starting Material 2 supra) using (Ph$_3$P)$_2$PdCl$_2$ (20 mg) and CuI (10 mg) as catalyst in DMF (2 mL) and Et$_3$N (2 mL) as solvent at 70° C. for 18 h to yield (S)-(Z)-1,3-dihydro-4-(3-hydroxy-1-octynyl)-3-[(3-methoxy-1H-pyrrol-2-yl)methylene]-2H-indol-2-one. (Yield 101 mg, 68%).

Example 26

(Z)-[3-[2,3-Dihydro-3-[(3-methoxy-1H-pyrrol-2-yl)methylene]-2-oxo-1H-indol-4-yl]-2-propynyl] propanedioic acid dimethyl ester (V)

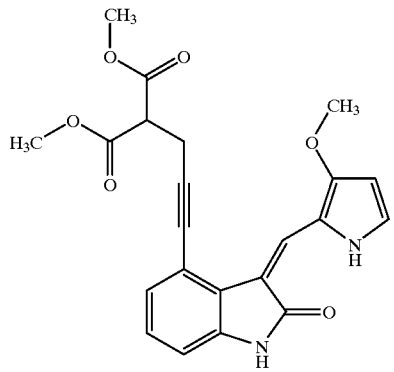

Using Method C above, dimethyl propargyl malonate (83 mg, 0.49 mmol) (Fluka) was coupled with (Z)-1,3-dihydro-4-iodo-3-[(3-methoxy-1H-pyrrol-2-yl)methylene]-2H-indol-2-one (150 mg, 0.41 mmol) (Starting Material 2 supra) using (Ph$_3$P)$_2$PdCl$_2$ (20 mg) and CuI (10 mg) as catalyst in DMF (2 mL) and Et$_3$N (2 mL) as solvent at 70° C. for 18 h yielding (Z)-[3-[2,3-dihydro-3-[(3-methoxy-1H-pyrrol-2-yl)methylene]-2-oxo-1H-indol-4-yl]-2-propynyl] propanedioic acid dimethyl ester. (Yield 82 mg, 49%).

Example 27

(Z)-[3-[2,3-Dihydro-3-[(3-methoxy-1H-pyrrol-2-yl)methylene]-2-oxo-1H-indol-4-yl]-2-propynyl] propanedioic acid (W)

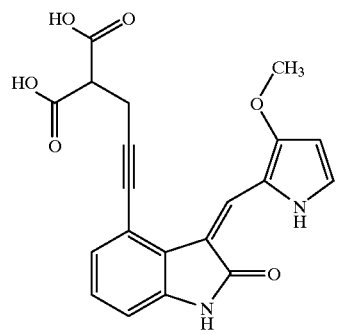

Using Method F above, (Z)-[3-[2,3-dihydro-3-[(3-methoxy-1H-pyrrol-2-yl)methylene]-2-oxo-1H-indol-4-yl]-2-propynyl]propanedioic acid dimethyl ester (68 mg, 0.16 mmol) (from Example 26 above) was hydrolyzed with LiOH•H$_2$O (140 mg, 3.32 mmol) in THF (1 mL) and water (1 mL) at room temperature for 20 h to yield (Z)-[3-[2,3-dihydro-3-[(3-methoxy-1H-pyrrol-2-yl)methylene]-2-oxo-1H-indol-4-yl]-2-propynyl]propanedioic acid. (Yield 49 mg, 82%).

Example 28

(Z)-1,3-Dihydro-4-(3-methoxy-1-propynyl)-3-[(3-methoxy-1H-pyrrol-2-yl)methylene]-2H-indol-2-one (X)

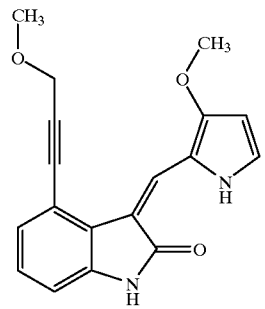

Using Method C above, methyl propargyl ether (34 mg, 0.49 mmol) (Aldrich) was coupled with (Z)-1,3-dihydro-4-iodo-3-[(3-methoxy-1H-pyrrol-2-yl)methylene]- 2H-indol-2-one (150 mg, 0.41 mmol) (Starting Material 2 supra) using (Ph$_3$P)$_2$PdCl$_2$ (20 mg) and CuI (10 mg) as catalyst in DMF (2 mL) and Et$_3$N (2 mL) as solvent at 70° C. for 18 h to yield (Z)-1,3-dihydro-4-(3-methoxy-1-propynyl)-3-[(3-methoxy-1H-pyrrol-2-yl)methylene]-2H-indol-2-one. (Yield 69 mg, 55%).

Example 29

(Z)-1,3-Dihydro-4-(3-hydroxy-1-propynyl)-3-[(3-methoxy-1H-pyrrol-2-yl)methylene]-2H-indol-2-one (Y)

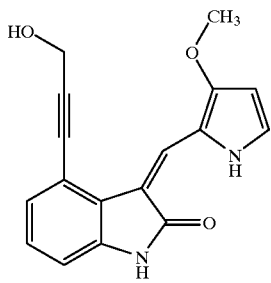

Using Method D above, propargyl alcohol (43.9 mg, 0.78 mmol) (Aldrich) was coupled with (Z)-4-bromo-1,3-dihydro-3-[(3-methoxy-1H-pyrrol-2-yl)methylene]-2H-indol-2-one (100 mg, 0.31 mmol) (Starting Material 1 supra) using DPPFPdCl$_2$ (12.8 mg) and CuI (3 mg) as catalyst in DMF (3 mL) and Et$_3$N (3 mL) as solvent at 85° C. for 18 h to yield (Z)-1,3-dihydro-4-(3-hydroxy-1-propynyl)-3-[(3-methoxy-1H-pyrrol-2-yl)methylene]-2H-indol-2-one. (Yield 42 mg, 46%).

Example 30

(Z)-1,3-Dihydro-4-(3-hydroxy-1-propynyl)-3-[(3-methoxy-1H-pyrrol-2-yl)methylene]-5-nitro-2H-indol-2-one (Z)

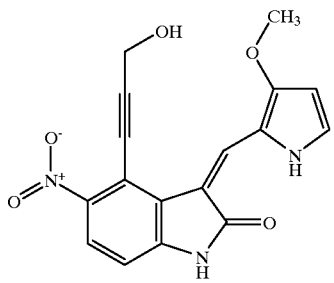

Using Method C above, propargyl alcohol (0.11 g, 1.95 mmol) (Aldrich) was coupled with (Z)-1,3-dihydro-4-iodo-3-[(3-methoxy-1H-pyrrol-2-yl)methylene]-5-nitro-2H-indol-2-one (0.32 g, 0.78 mmol) (Starting Material 2 above) using (Ph$_3$P)$_2$PdCl$_2$ (27.4 mg) and CuI (7.4 mg) as catalyst in DMF (3 mL) and Et$_3$N (3 mL) as solvent at 85° C. for 18 h to yield (Z)-1,3-dihydro-4-(3-hydroxy-1-propynyl)-3-[(3-methoxy-1H-pyrrol-2-yl)methylene]-5-nitro-2H-indol-2-one. (Yield 0.12 g, 46%).

Example 31

(Z)-1,3-Dihydro-4-[(1-hydroxycyclopentyl)ethynyl]-3-[(3-methoxy-1H-pyrrol-2-yl)methylene]-2H-indol-2-one (AA)

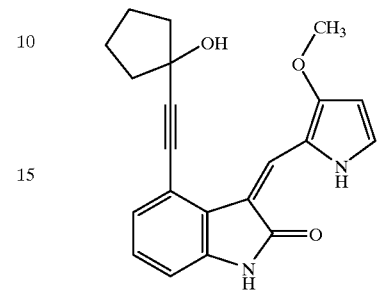

Using Method D above, 1-ethynyl-cyclopentanol (86.3 mg, 0.78 mmol) (Aldrich) was coupled with (Z)-4-bromo-1,3-dihydro-3-[(3-methoxy-1H-pyrrol-2-yl)methylene]-2H-indol-2-one (0.1 g, 0.31 mmol) (Starting Material 1 above) using DPPFPdCl$_2$ (12.6 mg) and CuI (3 mg) as catalyst in DMF (3 mL) and Et$_3$N (3 mL) as solvent at 85° C. for 2 days to yield (Z)-1,3-dihydro-4-[(1-hydroxycyclopentyl)ethynyl]-3-[(3-methoxy-1H-pyrrol-2-yl)methylene]-2H-indol-2-one. (Yield 43 mg, 40%).

Example 32

(Z)-5-Amino-1,3-dihydro-4-(3-hydroxy-1-propynyl)-3-[(3-methoxy-1H-pyrrol-2-yl)methylene]-2H-indol-2-one (BB)

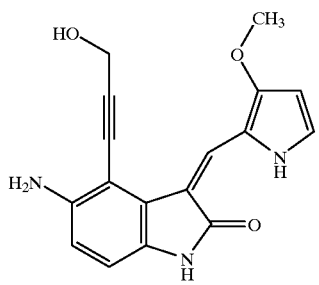

Using Method L above, (Z)-1,3-dihydro-4-(3-hydroxy-1-propynyl)-3-[(3-methoxy-1H-pyrrol-2-yl)methylene]-5-nitro-2H-indol-2-one (63 mg, 0.19 mmol) (from Example 30 above) was reduced with zinc (0.11 g, 1.67 mmol) and ammonium chloride (22.4 mg, 0.42 mmol) in 10% water in methanol (10 mL) with heating at reflux for 2 h to give (Z)-5-amino-1,3-dihydro-4-(3-hydroxy-1-propynyl)-3-[(3-methoxy-1H-pyrrol-2-yl)methylene]-2H-indol-2-one. (Yield 18 mg, 40%).

Example 33

(Z)-N-[2,3-Dihydro-3-[(3-methoxy-1H-pyrrol-2-yl)methylene]-2-oxo-4-(3-hydroxy-1-propynyl)-1H-indol-5-yl]-2-thiopheneacetamide (CC)

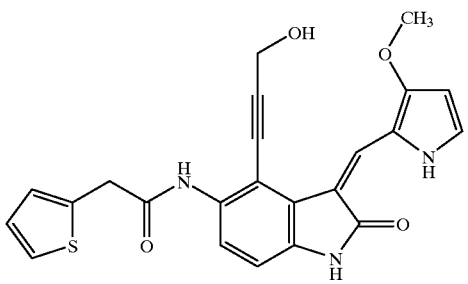

Using Method M above, (Z)-5-amino-1,3-dihydro-4-(3-hydroxy-1-propynyl)-3-[(3-methoxy-1H-pyrrol-2-yl)methylene]-2H-indol-2-one (20 mg, 0.065 mmol) (from Example 32 above) was acylated with 2-thiopheneacetyl chloride (21 mg, 0.13 mmol) (Aldrich) in THF (2 mL) at RT for 2 h to give (Z)-N-[2,3-dihydro-3-[(3-methoxy-1H-pyrrol-2-yl)methylene]-2-oxo-4-(3-hydroxy-1-propynyl)-1H-indol-5-yl]-2-thiopheneacetamide. (Yield 18.2 mg, 65%).

Example 34

(Z)-N-[2,3-Dihydro-4-(3-hydroxy-1-propynyl)-3-[(3-methoxy-1H-pyrrol-2-yl)methylene]-2-oxo-1H-indol-5-yl]-4-pyridinecarboxamide (DD)

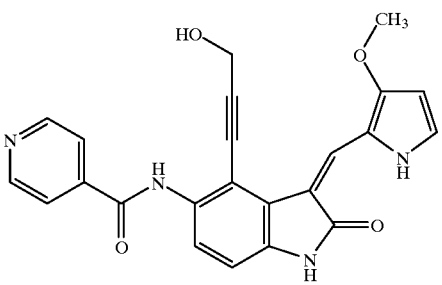

Using Method M above, (Z)-5-amino-1,3-dihydro-4-(3-hydroxy-1-propynyl)-3-[(3-methoxy-1H-pyrrol-2-yl)methylene]-2H-indol-2-one (20 mg, 0.065 mmol) (from Example 32 above) was acylated with isonicotinyl chloride (23 mg, 0.13 mmol) (Aldrich) in THF (2 mL) at room temperature for 10 days to give (Z)-N-[2,3-dihydro-4-(3-hydroxy-1-propynyl)-3-[(3-methoxy-1H-pyrrol-2-yl)methylene]-2-oxo-1H-indol-5-yl]-4-pyridinecarboxamide. (Yield 10 mg, 37%).

Example 35

(Z)-5-[2,3-Dihydro-3-[(3-methoxy-1H-pyrrol-2-yl)methylene]-5-nitro-2-oxo-1H-indol-4-yl]-4-pentynoic add methyl ester (EE)

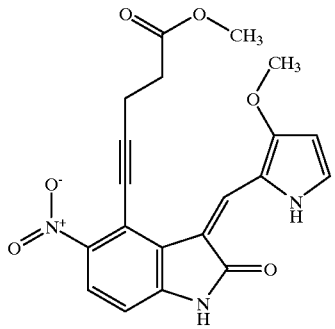

Using Method D above, methyl 4-pentynoate (0.18 g, 1.65 mmol) was coupled with (Z)-4-bromo-1,3-dihydro-3-[(3-methoxy-1H-pyrrol-2-yl)methylene]-5-nitro-2H-indol-2-one (Starting Material 1 supra) (0.3 g, 0.82 mmol) using $(Ph_3P)_2PdCl_2$ (28.8 mg) and CuI (7.8 mg) as catalyst in DMF (8 mL) and $Et_3N$ (8 mL) as solvent at 85° C. for 18 h to yield (Z)-5-[2,3-dihydro-3-[(3-methoxy-1H-pyrrol-2-yl)methylene]-5-nitro-2-oxo-1H-indol-4-yl]-4-pentynoic acid methyl ester. (Yield 0.23 g, 72%).

Example 36

(Z)-5-[5-Amino-2,3-dihydro-3-[(3-methoxy-1H-pyrrol-2-yl)methylene]-2-oxo-1H-indol-4-yl]-4-pentynoic acid methyl ester (FF)

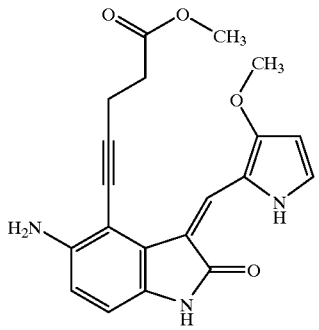

Using Method L above, (Z)-5-[2,3-dihydro-3-[(3-methoxy-1H-pyrrol-2-yl)methylene]-5-nitro-2-oxo-1H-indol-4-yl]-4-pentynoic acid methyl ester (0.22 g, 0.57 mmol) (from Example 35 above) was reduced with zinc (0.33 g, 5.1 mmol) and ammonium chloride (67.1 mg, 1.25 mmol) in 10% water in methanol (20 mL) with heating at reflux for 4 h to give (Z)-5-[5-amino-2,3-dihydro-3-[(3-methoxy-1H-pyrrol-2-yl)methylene]-2-oxo-1H-indol-4-yl]-4-pentynoic acid methyl ester (Yield 0.1 g, 48%).

Example 37

(Z)-5-[2,3-Dihydro-3-[(3-methoxy-1H-pyrrol-2-yl)methylene]-2-oxo-5-[(2-thienylacetyl)amino]-1H-indol-4-yl]-4-pentyonic acid methyl ester (GG)

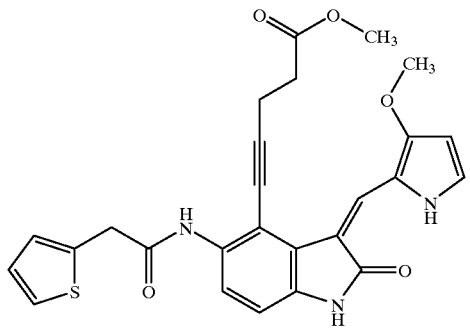

Using Method M above, (Z)-5-[5-amino-2,3-dihydro-3-[(3-methoxy-1H-pyrrol-2-yl)methylene]-2-oxo-1H-indol-4-yl]-4-pentynoic acid methyl ester (82.7 mg, 0.23 mmol) (from Example 36 above) was acylated with 2-thiopheneacetyl chloride (72.7 mg, 0.45 mmol) (Aldrich) in THF (8 mL) at room temperature for 18 h to give (Z)-5-[2,3-dihydro-3-[(3-methoxy-1H-pyrrol-2-yl)methylene]-2-oxo-5-[(2-thienylacetyl)amino]-1H-indol-4-yl]-4-pentyonic acid methyl ester. (Yield 90 mg, 65%).

Example 38

(Z)-5-[2,3-Dihydro-3-[(3-methoxy-1H-pyrrol-2-yl)methylene]-2-oxo-5-[(2-thienylacetyl)amino]-1H-indol-4-yl]-4-pentynoic acid (HH)

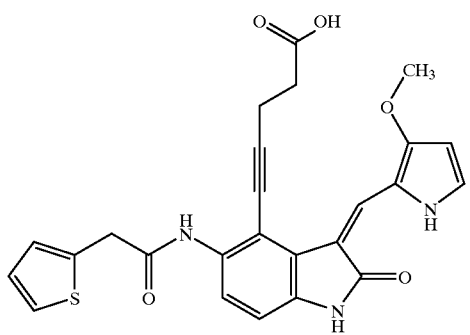

Using Method F above, (Z)-5-[2,3-dihydro-3-[(3-methoxy-1H-pyrrol-2-yl)methylene]-2-oxo-5-[(2-thienylacetyl)amino]-1H-indol-4-yl]-4-pentyonic acid methyl ester (from Example 37) (70 mg, 0.14 mmol) was hydrolyzed with LiOH·H$_2$O (21 mg, 0.50 mmol) in THF-water mixture (5 mL, V/V 2:1) at RT for 3 days to give (Z)-5-[2,3-dihydro-3-[(3-methoxy-1H-pyrrol-2-yl)methylene]-2-oxo-5-[(2-thienylacetyl)amino]-1H-indol-4-yl]-4-pentynoic acid. (Yield 56 mg, 82%).

Example 39

(Z)-4-(3-Amino-1-propynyl)-1,3-dihydro-3-[(3-methoxy-1H-pyrrol-2-yl)methylene]-2H-indol-2-one trifluoroacetate salt (II)

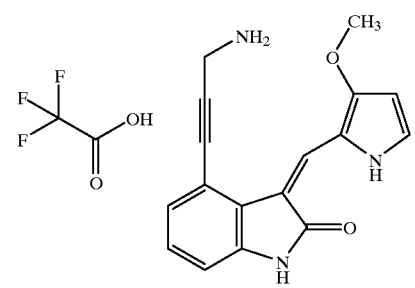

Using Method D above, propargylamine (34.5 mg, 0.63 mmol) (Aldrich) was coupled with (Z)-4-bromo-1,3-dihydro-3-[(3-methoxy-1H-pyrrol-2-yl)methylene]-2H-indol-2-one (0.1 g, 0.31 mmol) (Starting Material 1 supra) using (Ph$_3$P)$_2$PdCl$_2$ (11 mg) and CuI (3 mg) as catalyst in DMF (2 mL) and Et$_3$N (3 mL) as solvent at 80° C. for 20 h to give (Z)-4-(3-amino-1-propynyl)-1,3-dihydro-3-[(3-methoxy-1H-pyrrol-2-yl)methylene]-2H-indol-2-one trifluoroacetate salt after reverse phase chromatography purification. (Yield 14 mg, 15%).

Example 40

(Z)-1,3-Dihydro-3-[(3-methoxy-1H-pyrrol-2-yl)methylene]-4-[3-(N-methylamino)-1-propynyl]-2H-indol-2-one trifluoroacetate salt (JJ)

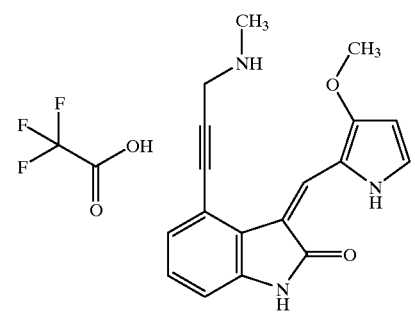

Using Method D above, N-methyl propargylamine (43.5 mg, 0.63 mmol) (Aldrich) was coupled with (Z)-4-bromo-1,3-dihydro-3-[(3-methoxy-1H-pyrrol-2-yl)methylene]-2H-indol-2-one (Starting Material 1 supra) (0.1 g, 0.31 mmol) using (Ph$_3$P)$_4$Pd (18 mg) and CuI (3 mg) as catalyst in DMF (3 mL) and Et$_3$N (3 mL) as solvent at 80° C. for 3 days to give (Z)-1,3-dihydro-3-[(3-methoxy-1H-pyrrol-2-yl)methylene]-4-[3-(N-methylamino)-1-propynyl]-2H-indol-2-one trifluoroacetate salt after reverse phase chromatography purification. (Yield 15 mg, 15%).

Example 41

(Z)-1,3-Dihydro-3-[(3-methoxy-1H-pyrrol-2-yl)methylene]-4-[3-(N-phenylmethylamino)-1-propynyl]-2H-indol-2-one (KK)

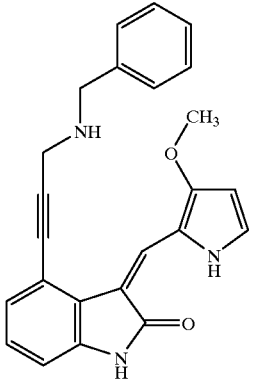

Using Method C above, N-benzyl-3-propynylamine (45 mg, 0.3 mmol) (prepared in accordance to B. Henke et al., *J. Org. Chem.* 57:7056–7066 (1992)) was coupled with (Z)-1,3-dihydro-4-iodo-3-[(3-methoxy-1H-pyrrol-2-yl)methylene]-2H-indol-2-one (0.11 g, 0.3 mmol) (Starting Material 2 supra) using $(Ph_3P)_2PdCl_2$ (11 mg) and CuI (3 mg) as catalyst in DMF (3 mL) and $Et_3N$ (3 mL) as solvent at 80° C. for 6 h to give (Z)-1,3-dihydro-3-[(3-methoxy-1H-pyrrol-2-yl)methylene]-4-[3-(N-phenylmethylamino)-1-propynyl]-2H-indol-2-one. (Yield 78 mg, 68%).

Example 42

(Z)-[3-[2,3-Dihydro-3-[(3-methoxy-1H-pyrrol-2-yl)methylene]-2-oxo-1H-indol-4-yl]-2-propynyl]carbamic acid methyl ester (LL)

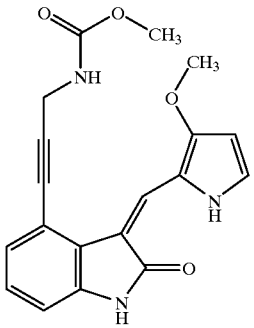

Using Method C above, 2-propynyl carbamic acid methyl ester (71.3 mg, 0.63 mmol) (see below) was coupled with (Z)-1,3-dihydro-4-iodo-3-[(3-methoxy-1H-pyrrol-2-yl)methylene]-2H-indol-2-one (110 mg, 0.3 mmol) (Starting Material 2 supra) using $(Ph_3P)_2PdCl_2$ (11 mg) and CuI (3 mg) as catalyst in DMF (3 mL) and $Et_3N$ (3 mL) as solvent at 80° C. for 6 h to give (Z)-[3-[2,3-dihydro-3-[(3-methoxy-1H-pyrrol-2-yl)methylene]-2-oxo-1H-indol-4-yl]-2-propynyl]carbamic acid methyl ester. (Yield 25 mg, 23%).

The 2-propynyl carbamic acid methyl ester was prepared by the reaction of propargylamine with methyl chloroformate in dichloromethane and saturated aqueous sodium bicarbonate solution.

Example 43

(Z)-Carbamic acid 3-[2,3-dihydro-3-[(3-methoxy-1H-pyrrol-2-yl)methylene]-2-oxo-1H-indol-4-yl]-2-propynyl ester (MM)

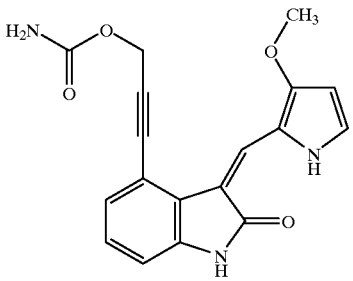

Using Method C above, propargyl carbamate (62.4 mg, 0.63 mmol) (see below) was coupled with (Z)-1,3-dihydro-4-iodo-3-[(3-methoxy-1H-pyrrol-2-yl)methylene]-2H-indol-2-one (110 g, 0.3 mmol) (Starting Material 2 supra) using $(Ph_3P)_2PdCl_2$ (11 mg) and CuI (3 mg) as catalyst in DMF (3 mL) and $Et_3N$ (3 mL) as solvent at 80° C. for 6 h to give (Z)-carbamic acid 3-[2,3-dihydro-3-[(3-methoxy-1H-pyrrol-2-yl)methylene]-2-oxo-1H-indol-4-yl]-2-propynyl ester. (Yield 43 mg, 43%).

The starting material propargyl carbanate was prepared by the reaction of propargyl alcohol with sodium cyanate in trifluoroacetic acid and diethyl ether at room temperature for 18 h.

Example 44

(Z)-N-Methylcarbamic acid 3-[2,3-dihydro-3-[(3-methoxy-1H-pyrrol-2-yl)methylene]-2-oxo-1H-indol-4-yl]-2-propynyl ester (NN)

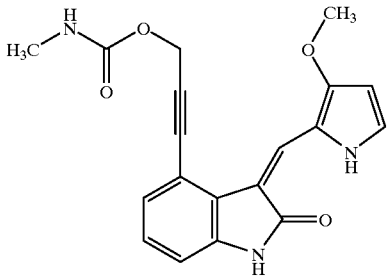

Using Method C above, N-methyl propargyl carbamate (71.3 mg, 0.63 mmol) (see below) was coupled with (Z)-1,3-dihydro-4-iodo-3-[(3-methoxy-1H-pyrrol-2-yl)methylene]-2H-indol-2-one (110 mg, 0.3 mmol) (Starting Material 2 supra) using $(Ph_3P)_2PdCl_2$ (11 mg) and CuI (3 mg) as catalyst in DMF (3 mL) and $Et_3N$ (3 mL) as solvent at 80° C. for 6 h to give (Z)-N-methylcarbamic acid 3-[2,3-dihydro-3-[(3-methoxy-1H-pyrrol-2-yl)methylene]-2-oxo-1H-indol-4-yl]-2-propynyl ester. (Yield 32 mg, 29%).

The N-methyl propargyl carbamate was prepared by the reaction of propargyl alcohol with methyl isocyanate in trifluoroacetic acid and diethyl ether at room temperature for 18 h.

Example 45 rac-(Z)-1,3-Dihydro-5-fluoro-4-(3-hydroxy-1-pentynyl)-3-[(4-methyl-1H-imidazol-5-yl)methylene]-2H-indol-2-one (OO)

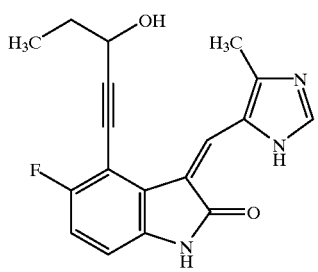

Using Method C above, 1-pentyn-3-ol (28.5 mg, 0.34 mmol) (Aldrich) was coupled with (Z)-1,3-dihydro-5-fluoro-4-iodo-3-[(4-methyl-1H-imidazol-5-yl)methylene]-2H-indol-2-one (50 mg, 0.135 mmol) (Starting Material 3 supra) using $(Ph_3P)_2PdCl_2$ (9.5 mg) and CuI (2.6 mg) as catalyst in DMF (3 mL) and $Et_3N$ (3 mL) as solvent at 80° C. for 6 h to give rac-(Z)-1,3-dihydro-5-fluoro-4-(3-hydroxy-1-pentynyl)-3-[(4-methyl-1H-imidazol-5-yl)methylene]-2H-indol-2-one. (Yield 17 mg, 39%).

Example 46 rac-(Z)-1,3-Dihydro-4-(3-hydroxy-1-pentynyl)-3-[(4-methyl-1H-imidazol-5-yl)methylene]-5-nitro-2H-indol-2-one (PP)

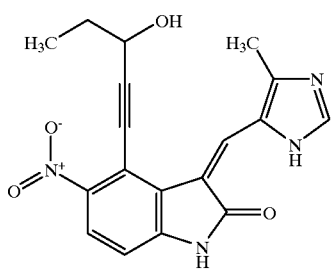

Using Method C above, 1-pentyn-3-ol (52.6 mg, 0.63 mmol) (Aldrich) was coupled with (Z)-1,3-dihydro-4-iodo-3-[(4-methyl-1H-imidazol-5-yl)methylene]-5-nitro-2H-indol-2-one (100 mg, 0.25 mmol) (Starting Material 4 supra) using $(Ph_3P)_2PdCl_2$ (17.5 mg) and CuI (4.8 mg) as catalyst in DMF (3 mL) and $Et_3N$ (3 mL) as solvent at 80° C. for 6 h to give rac-(Z)-1,3-dihydro-4-(3-hydroxy-1-pentynyl)-3-[(4-methyl-1H-imidazol-5-yl)methylene]-5-nitro-2H-indol-2-one. (Yield 12 mg, 14%).

Example 47

(Z)-1,3-Dihydro-5-fluoro-4-(3-hydroxy-1-propynyl)-3-[(4-methyl-1H-imdazol-5-yl)methylene]-2H-indol-2-one, trifluoroacetate salt (QQ)

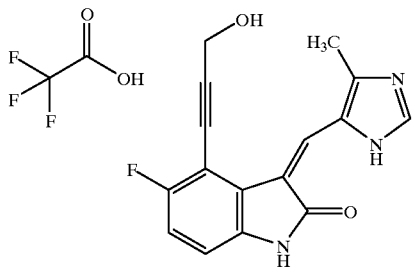

Using Method C above, propargyl alcohol (38 mg, 0.68 mmol) was coupled with (Z)-1,3-dihydro-5-fluoro-4-iodo-3-[(4-methyl-1H-imidazol-5-yl)methylene]-2H-indol-2-one (100 mg, 0.27 mmol) (Starting Material 3 supra) using $(Ph_3P)_2PdCl_2$ (19 mg) and CuI (5.2 mg) as catalyst in DMF (3 mL) and $Et_3N$ (3 mL) as solvent at 80° C. for 1 day to give (Z)-1,3-dihydro-5-fluoro-4-(3-hydroxy-1-propynyl)-3-[(4-methyl-1H-imidazol-5-yl)methylene]-2H-indol-2-one trifluoroacetate salt after reverse phase chromatography purification. (Yield 37 mg, 46%).

Example 48

(Z)-1,3-Dihydro-5-fluoro-4-[3-(N-methylamino)-1-propynyl]-3-[(4-methyl-1H-imidazol-5-yl)methylene]-2H-indol-2-one (RR)

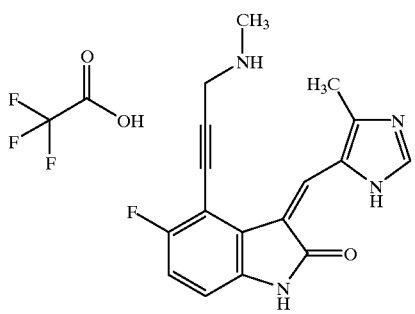

Using Method C above, N-methyl propargylamine (23.3 mg, 0.34 mmol) (Aldrich) was coupled with (Z)-1,3-dihydro-5-fluoro-4-iodo-3-[(4-methyl-1H-imidazol-5-yl)methylene]-2H-indol-2-one (50 mg, 0.135 mmol) (Starting Material 3 supra) using $(Ph_3P)_4Pd$ (15.6 mg) and CuI (3 mg) as catalyst in DMF (3 mL) and $Et_3N$ (3 mL) as solvent at 80° C. for 8 h to give (Z)-1,3-dihydro-5-fluoro-4-[3-(N-methylamino)-1-propynyl]-3-[(4-methyl-1H-imidazol-5-yl)methylene]-2H-indol-2-one. (Yield 17 mg, 41%).

Example 49

(Z)-1,3-Dihydro-4-ethynyl-3-[(3-methoxy-1H-pyrrol-2-yl)methylene]-2H-indol-2-one (SS)

Step 1: (Z)-1,3-Dihydro-3-[(3-methoxy-1H-pyrrol-2-yl)methylene]-4-(2-trimethylsilyl-ethynyl)-2H-indol-2-one

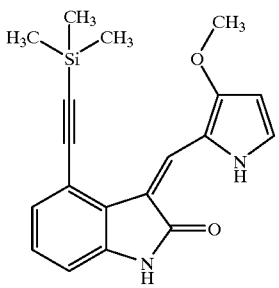

Using Method D above, trimethylsilyl acetylene (0.94 g, 9.63 mmol) (Aldrich) was coupled with (Z)-4-bromo-1,3-dihydro-3-[(3-methoxy-1H-pyrrol-2-yl)methylene]-2H-indol-2-one (2.05 g, 6.42 mmol) (Starting Material 1 supra) using $(Ph_3P)_2PdCl_2$ (0.23 g) and CuI (61 mg) as catalyst in DMF (15 mL) and $Et_3N$ (15 mL) as solvent at 80° C. for 2 days to give (Z)-1,3-dihydro-3-[(3-methoxy-1H-pyrrol-2-yl)methylene]-4-(2-trimethylsityl-ethynyl)-2H-indol-2-one. (Yield 1.3 g, 60%).

Step 2: (7)-1,3-Dihydro-4-ethynyl-2-[(1-methoxy-1-pyrrol-2-yl)methylene]-2H-indol-2-one (SS)

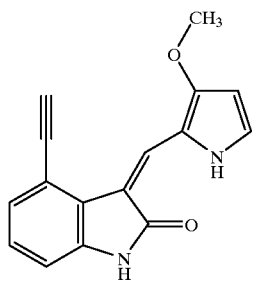

Using Method K above, a solution of (Z)-1,3-dihydro-3-[(3-methoxy-1H-pyrrol-2-yl)methylene]-4-(2-trimethylsityl-ethynyl)-2H-indol-2-one (1.3 g, 3.86 mmol) (from Step 1 above) in EtOH (80 mL) was treated with $AgNO_3$ (1.46 g, 8.59 mmol) in ethanol (5 mL) and water (15 mL) at room temperature for 1 h followed by KCN (2.71 g, 41.6 mmol) in water (10 mL) to give (Z)-1,3-dihydro-4-ethynyl-3-[(3-methoxy-1H-pyrrol-2-yl)methylene]-2H-indol-2-one. (Yield 1.02 g, 100%).

Example 50 rac-(Z)-1,3-Dihydro-5-fluoro-4-(4-hydroxy-1-pentynyl)-3-[(4-methyl-1H-imidazol-5-yl)methylene]-2H-indol-2-one, trifluoroacetate salt (TT)

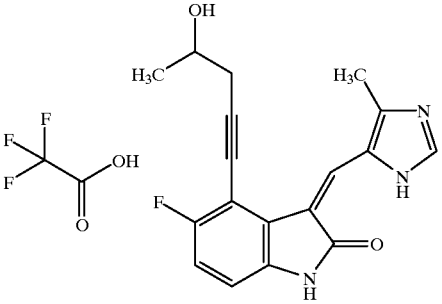

Using Method C above, 1-pentyn-4-ol (28.5 mg, 0.34 mmol) (Aldrich) was coupled with (Z)-1,3-dihydro-5-fluoro-4-iodo-3-[(4-methyl-1H-imidazol-5-yl)methylene]-2H-indol-2-one (Starting Material 3 supra) (50 mg, 0.135 mmol) using $(Ph_3P)_2PdCl_2$ (9.5 mg) and CuI (3 mg) as catalyst in DMF (3 mL) and $Et_3N$ (3 mL) as solvent at 80° C. for 8 h to give rac-(Z)-1,3-dihydro-5-fluoro-4-(4-hydroxy-1-pentynyl)-3-[(4-methyl-1H-imidazol-5-yl)methylene]-2H-indol-2-one trifluoroacetate salt after reverse phase chromatography purification. (Yield 26 mg, 59%).

Example 51

(Z)-1,3-Dihydro-4-[3-(N,N-dimethylamino)-1-propynyl]-5-fluoro-3-[(4-methyl-1H-imidazol-5-yl)methylene]-2H-indol-2-one (UU)

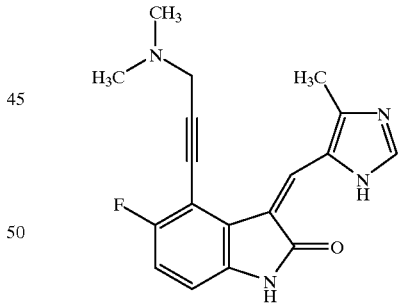

Using Method C above, N,N-dimethyl propargylamine (42.2 mg, 0.51 mmol) (Aldrich) was coupled with (Z)-1,3-dihydro-5-fluoro-4-iodo-3-[(4-methyl-1H-imidazol-5-yl)methylene]-2H-indol-2-one (75 mg, 0.203 mmol) (Starting Material 3 supra) using $(Ph_3P)_4Pd$ (23.5 mg) and CuI (4 mg) as catalyst in DMF (3 mL) and $Et_3N$ (3 mL) as solvent at 80° C. for 6 h to give (Z)-1,3-dihydro-4-[3-(N,N-dimethylamino)-1-propynyl]-5-fluoro-3-[(4-methyl-1H-imidazol-5-yl)methylene]-2H-indol-2-one. (Yield 40 mg, 61%).

Example 52

(Z)-4-[3-Amino-3-methyl-1-butynyl]-1,3-dihydro-5-fluoro-3-[(4-methyl-1H-imidazol-5-yl)methylene]-2H-indol-2-one (W)

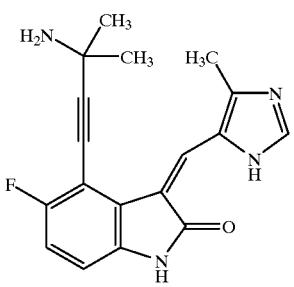

Using Method C above, 3-amino-3-methyl-1-butyne (42.2 mg, 0.51 mmol) (Aldrich) was coupled with (Z)-1,3-dihydro-5-fluoro-4-iodo-3-[(4-methyl-1H-imidazol-5-yl)methylene]-2H-indol-2-one (Starting Material 3 supra) (75 mg, 5 0.203 mmol) using (Ph$_3$P)$_4$Pd (23.5 mg) and CuI (4 mg) as catalyst in DMF (3 mL) and Et$_3$N (3 mL) as solvent at 80° C. for 18 h to give (Z)-4-[3-amino-3-methyl-1-butynyl]-1,3-dihydro-3-[(4-methyl-1H-imidazol-5-yl)methylene]-2H-indol-2-one. (Yield 44 mg, 67%).

Example 53

(Z)-Carbamic acid 3-[2,3-dihydro-3-[(4-methyl-1H-imidazol-5-[5-yl)methylene]-5-fluoro-2-oxo-1H-indol-4-yl]-2-propynyl ester (WW)

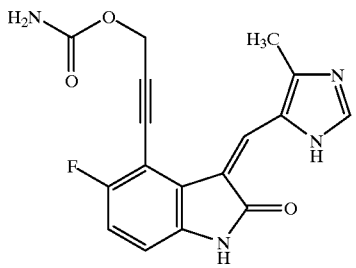

Using Method C above, propargyl carbamate (50.3 mg, 0.51 mmol) (see Example 43 supra) was coupled with (Z)-1,3-dihydro-5-fluoro-4-iodo-3-[(4-methyl-1H-imidazol-5-yl)methylene]-2H-indol-2-one (Starting Material 3 supra) (75 mg, 0.203 mmol) using (Ph$_3$P)$_4$Pd (23.5 mg) and CuI (4 mg) as catalyst in DMF (3 mL) and Et$_3$N (3 mL) as solvent at 80° C. for 1 day to give (Z)-carbamic acid 3-[2,3-dihydro-3-[(4-methyl-1H-imidazol-5-yl)methylene]-5-fluoro-2-oxo-1H-indol-4-yl]-2-propynyl ester. (Yield 10 mg, 15%).

Example 54

(Z)-1,3-Dihydro-5-fluoro-3-[(4-methyl-1H-imidazol-5-yl)methylene]-4-[3-(4-morpholinyl)-1-propynyl]-2H-indol-2-one (XX)

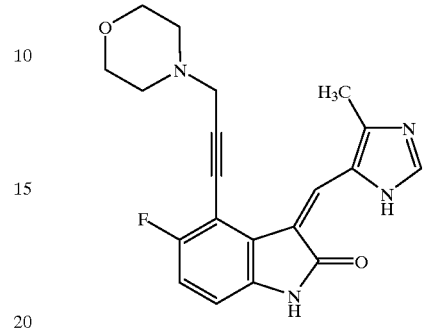

Using Method C above, 3-(4-morpholinyl)-1-propyne (63.6 mg, 0.51 mmol) (prepared according to H. Kano et al., *J. Med. Chem.* 10:411–418 (1967)) was coupled with (Z)-1,3-dihydro-5-fluoro-4-iodo-3-[(4-methyl-1H-imidazol-5-yl)methylene]-2H-indol-2-one (75 mg, 0.203 mmol) (Starting Material 3 supra) using (Ph$_3$P)$_4$Pd (23.5 mg) and CuI (4 mg) as catalyst in DMF (3 mL) and Et$_3$N (3 mL) as solvent at 80° C. for 18 h to give (Z)-1,3-dihydro-5-fluoro-3-[(4-methyl-1H-imidazol-5-yl)methylene]-4-[3-(4-morpholinyl)-1-propynyl]-2H-indol-2-one. (Yield 40 mg, 54%).

Example 55

(Z)-[3-[2,3-Dihydro-5-fluoro-3-[(4-methyl-1H-imidazol-5-yl)methylene]-2-oxo-1H-indol-4-yl]-2-propynyl]carbamic acid methyl ester (YY)

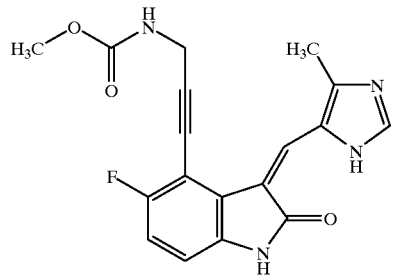

Using Method C above, 2-propynyl carbamic acid methyl ester (57.5 mg, 0.51 mmol) (see Example 42 supra) was coupled with (Z)-1,3-dihydro-5-fluoro-4-iodo-3-[(4-methyl-1H-imidazol-5-yl)methylene]-2H-indol-2-one (Starting Material 3 supra) (75 mg, 0.203 mmol) using (Ph$_3$P)$_4$Pd (23.5 mg) (Aldrich) and CuI (4 mg) as catalyst in DMF (3 mL) and Et$_3$N (3 mL) as solvent at 80° C. for 18 h to give (Z)-[3-[2,3-dihydro-5-fluoro-3-[(4-methyl-1H-imidazol-5-yl)methylene]-2-oxo-1H-indol-4-yl]-2-propynyl]carbamic acid methyl ester. (Yield 15 mg, 21%).

Example 56

(Z)-[3-[5-fluoro-2,3-dihydro-3-[(4-methyl-1H-imidazol-5-yl)methylene]-2-oxo-1H-indol-4-yl]-2-propynyl]urea (ZZ)

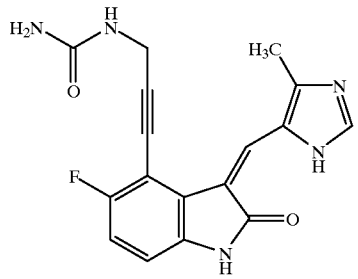

Using Method C above, 2-propynylurea (50 mg, 0.51 mmol) (see below) was coupled with (Z)-1,3-dihydro-5-fluoro-4-iodo-3-[(4-methyl-1H-imidazol-5-yl)methylene]-2H-indol-2-one (Starting Material 3 supra) (75 mg, 0.203 mmol) using (Ph$_3$P)$_4$Pd (23.5 mg) and CuI (4 mg) as catalyst in DMF (3 mL) and Et$_3$N (3 mL) as solvent at 80° C. for 18 h to give (Z)-[3-[5-fluoro-2,3-dihydro-3-[(4-methyl-1H-imidazol-5-yl)methylene]-2-oxo-1H-indol-4-yl]-2-propynyl]urea. (Yield 11 mg, 16%).

The starting material 2-propynylurea was prepared by the reaction of propargylamine (Aldrich) with sodium cyanate in concentrated hydrochloric acid-water mixture (3:2) at room temperature for 30 min.

Example 57 rac-(Z)-2-(Acetylamino)-5-[5-fluoro-2,3,dihydro-3-[(4-methyl-1H-imidazol-5-yl)methylene]-2-oxo-1H-indol-4-yl]-4-pentynoic acid ethyl ester (AAA)

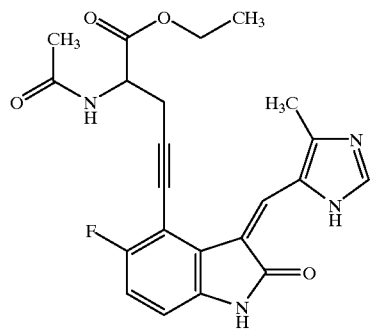

Using Method C above, 2-(acetylamino)-4-pentynoic acid ethyl ester (92.6 mg, 0.51 mmol) (Bachem) was coupled with (Z)-1,3-dihydro-5-fluoro-4-iodo-3-[(4-methyl-1H-imidazol-5-yl)methylene]-2H-indol-2-one (Starting Material 3 supra) (75 mg, 0.203 mmol) using (Ph$_3$P)$_4$Pd (23.5 mg) and CuI (4 mg) as catalyst in DMF (3 mL) and Et$_3$N (3 mL) as solvent at 80° C. for 5 h to give rac-(Z)-2-(acetylamino)-5-[5-fluoro-2,3,dihydro-3-[(4-methyl-1H-imidazol-5-yl)methylene]-2-oxo-1H-indol-4-yl]-4-pentynoic acid ethyl ester. (Yield 70 mg, 81%).

Example 58

(Z)-4-[3-(N,N-Diethylamino)-1-propynyl]-1,3-dihydro-5-fluoro-3-[(4-methyl-1H-imidazol-5-yl)methylene]-2H-indol-2-one (BBB)

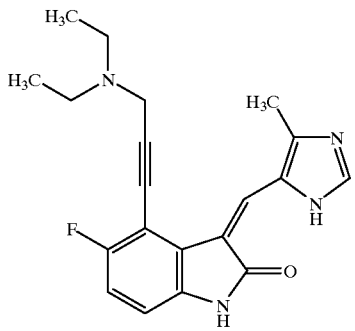

Using Method C above, N,N-diethyl propargylamine (38 mg, 0.34 mmol) (Aldrich) was coupled with (Z)-1,3-dihydro-5-fluoro-4-iodo-3-[(4-methyl-1H-imidazol-5-yl)methylene]-2H-indol-2-one (Starting Material 3 supra) (50 mg, 0.135 mmol) using (Ph$_3$P)$_4$Pd (16 mg) and CuI (3 mg) as catalyst in DMF (3 mL) and Et$_3$N (3 mL) as solvent at 80° C. for 18 h to give (Z)-4-(3-(N,N-diethylamino)-1-propynyl]-1,3-dihydro-5-fluoro-3-[(4-methyl-1H-imidazol-5-yl)methylene]-2H-indol-2-one. (Yield 20 mg, 42%).

Example 59

(Z)-4-[3-Amino-3-ethyl-1-pentynyl]-1,3-dihydro-5-fluoro-3-[(4-methyl-1H-imidazol-5-yl)methylene]-2H-indol-2-one (CCC)

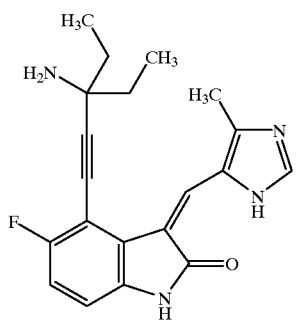

Using Method C above, 3-amino-3-ethyl-1-pentyne (37.6 mg, 0.34 mmol) (Aldrich) was coupled with (Z)-1,3-dihydro-5-fluoro-4-iodo-3-[(4-methyl-1H-imidazol-5-yl)methylene]-2H-indol-2-one (Starting Material 3 supra) (50 mg, 0.135 mmol) using (Ph$_3$P)$_4$Pd (16 mg) and CuI (3 mg) as catalyst in DMF (3 mL) and Et$_3$N (3 mL) as solvent at 80° C. for 6 h to give (Z)-4-[3-amino-3-ethyl-1-pentynyl]-1,3-dihydro-5-fluoro-3-[(4-methyl-1H-imidazol-5-yl)methylene]-2H-indol-2-one. (Yield 45 mg, 95%).

Example 60

(Z)-[3-[2,3-Dihydro-5-fluoro-3-[(4-methyl-1H-imidazol-5-yl)methylene]-2-oxo-1H-indol-4-yl]-1,1-dimethyl-2-propynyl]carbamic acid methyl ester (DDD)

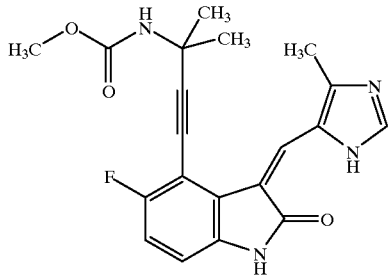

Using Method C above, (1,1-dimethyl-2-propynyl)-carbamic acid methyl ester (47.7 mg, 0.34 mmol) (see below) was coupled with (Z)-1,3-dihydro-5-fluoro-4-iodo-3-[(4-methyl-1H-imidazol-5-yl)methylene]-2H-indol-2-one (Starting Material 3 supra) (50 mg, 0.135 mmol) using (Ph$_3$P)$_4$Pd (16 mg) and CuI (3 mg) as catalyst in DMF (3 mL) and Et$_3$N (3 mL) as solvent at 80° C. for 5 h to give (Z)-[3-[2,3-dihydro-5-fluoro-3-[(4-methyl-1H-imidazol-5-yl)methylene]-2-oxo-1H-indol-4-yl]-1,1-dimethyl-2-propynyl]carbamic acid methyl ester. (Yield 40 mg, 77%).

The starting (1,1-dimethyl-2-propynyl)-carbamic acid methyl ester was prepared by the reaction of 3-amino-3-methyl-1-butyne (Aldrich) with methyl chloroformate (Aldrich) in dichloromethane and saturated aqueous sodium bicarbonate solution.

Example 61

N-[3-[2,3-Dihydro-5-fluoro-3-[(5-methyl-3H-imidazol-4-yl)-methylene]-2-oxo-1H-indol-4-yl]-prop-2-ynyl]-acetamide (EEE)

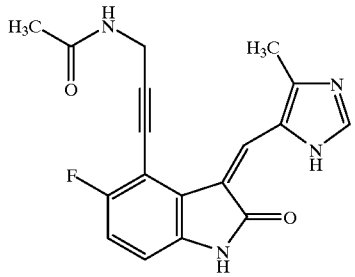

Using Method C above, N-propargylacetamide (32.8 mg, 0.34 mmol) (prepared by the reaction of propargylamine (Aldrich) with acetyl chloride and triethylamine in dichloromethane at 0° C. for 3 h) was coupled with (Z)-1,3-dihydro-5-fluoro-4-iodo-3-[(4-methyl-1H-imidazol-5-yl)methylene]-2H-indol-2-one (Starting Material 3 supra) (50 mg, 0.135 mmol) using (Ph$_3$P)$_4$Pd (16 mg) and CuI (3 mg) as catalyst in DMF (3 mL) and Et$_3$N (3 mL) as solvent at 80° C. for 5 h to give N-[3-[2,3-dihydro-5-fluoro-3-[(5-methyl-3H-imidazol-4-yl)methylene]-2-oxo-1H-indol-4-yl]-prop-2-ynyl]-acetamide. (Yield 35 mg, 77%).

Example 62

(Z)-1,3-Dihydro-5-fluoro-3-[(4-methyl-1H-imidazol-5-yl)methylene]-4-[3-(1-piperidinyl)-1-propynyl]-2H-indol-2-one (FFF)

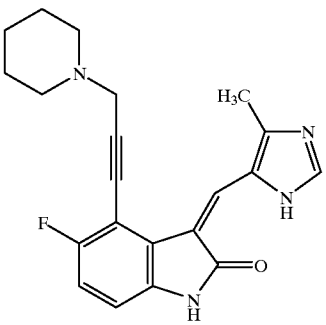

Using Method C above, 1-(2-propynyl)-piperidine (41.3 mg, 0.34 mmol) (prepared according to Kano et al. supra) was coupled with (Z)-1,3-dihydro-5-fluoro- 4-iodo-3-[(4-methyl-1H-imidazol-5-yl)methylene]-2H-indol-2-one (Starting Material 3 supra) (50 mg, 0.135 mmol) using (Ph$_3$P)$_4$Pd (16 mg) and CuI (3 mg) as catalyst in DMF (3 mL) and Et$_3$N (3 mL) as solvent at 80° C. for 5 h to give (Z)-1,3-dihydro-5-fluoro-3-[(4-methyl-1H-imidazol-5-yl)methylene]-4-[3-(1-pipendinyl)-1-propynyl]-2H-indol-2-one. (Yield 15 mg, 31%).

Example 63

(Z)-4-Iodo-3-[(1H-pyrrol-2-yl)methylene]-1,3-dihydro-indol-2-one

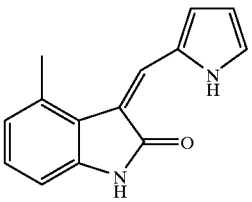

A mixture of 1,3-dihydro-4-iodo-2H-indol-2-one (404.1 mg, 1.56 mmol) (prepared according to T. Fukuyama et al., supra) and pyrrole-2-carboxaldehyde (163.2 mg, 1.72 mmol) (Aldrich) in 2-propanol (6.2 mL) was treated with 2 drops of piperidne (Aldrich). The reaction mixture was heated at reflux for 24 h and then allowed to cool to 23° C., at which time, the reaction mixture was filtered. The solid was washed several times with cold distilled water and then allowed to air dry to provide pure (Z)-1,3-dihydro-4-iodo-3-[(1H-pyrrol-2-yl)methylene]-indol-2-one. (Yield 341.8 mg, 65%) as a yellow solid, which was used without further purification.

Example 64

3-[2,3-Dihydro-(Z)-3-[(1H-pyrrol-2-yl)methylene]-2-oxo-1H-indol-4-yl]-(E)-2-propenoic acid methyl ester (GGG)

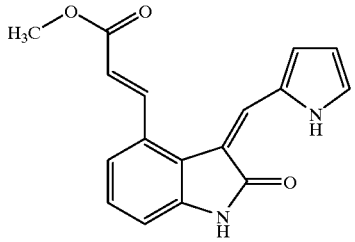

To a stirred solution of (Z)-1,3-dihydro-4-iodo-3-[(1H-pyrrol-2-yl)methylene]-indol-2-one (from Example 63) (500 mg, 1.49 mmol) in DMF (8 mL) and TEA (3 mL) was added methyl acrylate (0.26 mL, 2.98 mmol) (Aldrich), tri-o-tolylphosphine (361 mg, 1.19 mmol) (Aldrich) and Pd(OAc)$_2$ (67 mg, 0.30 mmol) (Aldrich). The reaction mixture was stirred at 85° C. overnight in a pressure tube. The solvent was removed in vacuo, and the residue was purified by silica gel chromatography (Hex:EtOAc=5:1) to provide 3-[2,3-dihydro-(Z)-3-[(1H-pyrrol-2-yl)methylene]-2-oxo-1H-indol-4-yl]-(E)-2-propenoic acid methyl ester as a yellow solid. (Yield 363 mg, 83%).

Example 65

3-[2,3-Dihydro-(Z)-3-[(3-methoxy-1H-pyrrol-2-yl)methylene]-2-oxo-1H-indol-4-yl]-(E)-2-propenoic acid methyl ester (HHH)

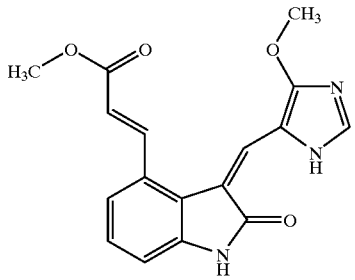

To a stirred solution of (Z)-1,3-dihydro-4-iodo-3-[(3-methoxy-1H-pyrrol-2-yl)methylene]-2H-indol-2-one (545 mg, 1.49 mmol) (Starting Material 2 supra) in DMF (8 mL) and TEA (3 mL) was added methyl acrylate (0.26 mL, 2.98 mmol) (Aldrich), tri-o-tolylphosphine (361 mg, 1.19 mmol) (Aldrich) and Pd(OAc)$_2$ (67 mg, 0.30 mmol) (Aldrich). The reaction mixture was stirred at 85° C. overnight in a pressure tube. The solvent was removed in vacuo, and the residue was purified by silica gel chromatography (Hex:EtOAc=5:1) to provide 3-[2,3-dihydro-(Z)-3-[(3-methoxy-1H-pyrrol-2-yl)methylene]-2-oxo-1H-indol-4-yl]-(E)-2-propenoic acid methyl ester as a yellow solid. (Yield 371 mg, 77%).

Example 66

3-Hydroxy-1-propenyl-boronic acid

To a stirred solution of propargyl alcohol (0.584 mL, 10 mmol) (Aldrich) in THF (3 mL) was added dropwise catecholborane (20 mL, 1.0 M solution in THF, 20 mmol) (Aldrich) at room temperature. After gas evolution had ceased, the mixture was heated under reflux for 5 h and allowed to cool to room temperature. To the cooled reaction mixture was added water (10 mL). The mixture was then stirred for 2 h at 20° C. The solvent was evaporated, and the aqueous layer was washed with ether (3×15 mL). The water was lyophillized, and the resulting 3-hydroxy-1-propenyl-boronic acid was used without further purification.

Example 67

1,3-Dihydro-4-(3-hydroxy-propenyl)-3-[(3-methoxy-1H-pyrrol-2-yl)methylene]-indol-2-one (III)

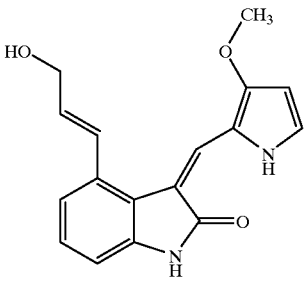

To a stirred solution of (Z)-1,3-dihydro-4-iodo-3-[(3-methoxy-1H-pyrrol-2-yl)methylene]-2H-indol-2-one (50 mg, 0.14 mmol) (Starting Material 2 supra) in dimethoxyethane (5 mL) was added 3-hydroxy-1-propenyl-boronic acid (from Example 66 above) (42 mg, 0.418 mmol), tetrakis(triphenylphosphine)palladium(0) (39 mg, 0.034 mmol) (Aldrich) and 2M Na$_2$CO$_3$ solution in H$_2$O (0.34 mL). The reaction mixture was stirred at 85° C. overnight in a pressure tube. The solvent was removed in vacuo, and the residue was purified by silica gel chromatography (Hex:EtOAc=5:1) to provide 1,3-dihydro-4-(3-hydroxy-propenyl)-3-[(3-methoxy-1H-pyrrol-2-yl)methylene]-indol-2-one as a yellow solid. (Yield 22 mg, 53%).

Example 68

4-Hydroxy-1-butenyl-boronic acid

To a stirred solution of 3-butyn-1-ol (0.748 mL, 10 mmol) (Aldrich) in THF (3 mL) was added dropwise catecholborane (20 mL, 1.0 M solution in THF, 20 mmol) (Aldrich) at room temperature. After gas evolution had ceased, the mixture was heated under reflux for 5 h and allowed to cool to room temperature. To the cooled reaction mixture was added water (10 mL). The mixture was then stirred for 2 h at 20° C. The solvent was evaporated, and the aqueous layer was washed with ether (3×15 mL). The water was lyophillized, and the resulting 4-hydroxy-1-butenyl-boronic acid was used without further purification.

Example 69

1,3-Dihydro-4-(4-hydroxy-but-1-enyl)-3-[(3-methoxy-1H-pyrrol-2-yl)methylene]-indol-2-one (JJJ)

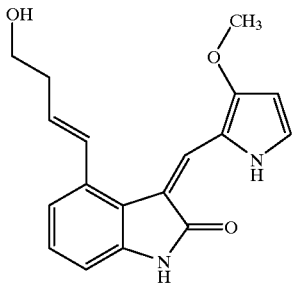

To a stirred solution of (Z)-1,3-dihydro-4-iodo-3-[(3-methoxy-1H-pyrrol-2-yl)methylene]-2H-indol-2-one (50 mg, 0.14 mmol) (Starting Material 2) in dimethoxyethane (5 mL) was added 4-hydroxy-1-butenyl-boronic acid (48 mg, 0.418 mmol) (from Example 68 above), tetrakis (triphenylphosphine)palladium(0) (39 mg, 0.034 mmol) (Aldrich) and 2M $Na_2CO_3$ solution in $H_2O$ (0.34 mL). The reaction mixture was stirred at 85° C. overnight in a pressure tube. The solvent was removed in vacuo, and the residue was purified by silica gel chromatography (Hex:EtOAc=5:1) to provide 1,3-dihydro-4-(4-hydroxy-but-1-enyl)-3-[(3-methoxy-1H-pyrrol-2-yl)methylene]-indol-2-one as a yellow solid. (Yield 21 mg, 50%).

Example 70

(R)-(Z)-1,3-Dihydro-5-fluoro-4-(4-hydroxy-1-pentynyl)-3-[(4-methyl-1H-imidazol-5-yl)methylene]-2H-indol-2-one (KKK)

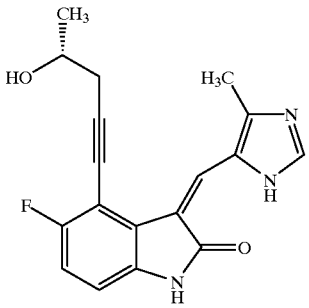

Using Method C above, (R)-pent-4-yn-2-ol (68 mg, 0.82 mmol) (see Example 78 below) was coupled with (Z)-1,3-dihydro-5-fluoro-4-iodo-3-[(4-methyl-1H-imidazol-5-yl)methylene]-2H-indol-2-one (100 mg, 0.27 mmol) (Starting Material 3 supra) using $(Ph_3P)_4Pd$ (31 mg, 0.03 mmol) and CuI (6 mg) in a mixture of DMF (5 mL) and $Et_3N$ (5 mL) as solvent at 80° C. for 4 hrs. Upon completion, the reaction mixture was concentrated and the residue was chromatographed on a silica gel column with neat $CH_3CN$ then THF and finally MeOH as elution solvent. The resulting (R)-(Z)-1,3-Dihydro-5-fluoro-4-(4-hydroxy-1-pentynyl)-3-[(4-methyl-1H-imidazol-5-yl)methylene]-2H-indol-2-one was triturated with $Et_2O$ and then recrystalized from superheated EtOH. (Yield 18 mg, 20%).

Example 71

(S)-(Z)-1,3-Dihydro-5-fluoro-4-(4-hydroxy-1-pentynyl)-3-[(4-methyl-1H-imidazol-5-yl)methylene]-2H-indol-2-one (LLL)

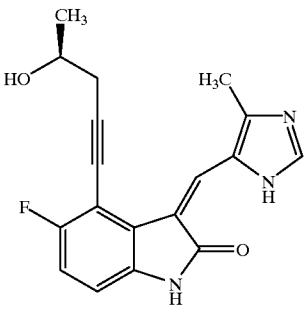

Using Method C above, (S)-pent-4-yn-2-ol (68 mg, 0.82 mmol) (see Example 81 below) was coupled with (Z)-1,3-dihydro-5-fluoro-4-iodo-3-[(4-methyl-1H-imidazol-5-yl)methylene]-2H-indol-2-one (100 mg, 0.27 mmol) (Starting Material 3 supra) using $(Ph_3P)_4Pd$ (31 mg, 0.03 mmol) and CuI (6 mg) in a mixture of DMF (5 mL) and $Et_3N$ (5 mL) as solvent at 80° C. for 4 hrs. Upon completion, the reaction mixture was concentrated and the residue was chromatographed on a silica gel column with neat $CH_3CN$ then THF and finally MeOH as elution solvent. The resulting (S)-(Z)-1,3-Dihydro-5-fluoro-4-(4-hydroxy-1-pentynyl)-3-[(4-methyl-1H-imidazol-5-yl)methylene]-2H-indol-2-one was triturated with $Et_2O$ and then recrystalized from superheated EtOH. (Yield 57 mg, 65%).

Example 72 rac-(Z)-1,3-Dihydro-5-fluoro-4-(3-hydroxy-1-pentynyl)-3-[(3-methoxy-1H-pyrrol-2-yl)methylene]-2H-indol-2-one (MMM)

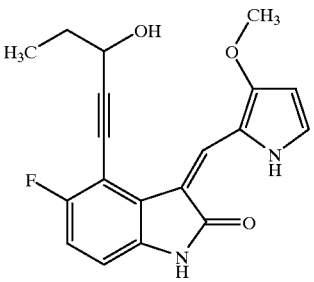

Using Method C above, 1-pentyn-3-ol (54.5 mg, 0.65 mmol) (Aldrich) was coupled with (Z)-1,3-dihydro-5-fluoro-4-iodo-3-[(3-methoxy-1H-pyrrol-2-yl)methylene]-2H-indol-2-one (100 mg, 0.26 mmol) (Starting Material 6, supra) using $(Ph_3P)_4Pd$ (30 mg) and CuI (5 mg) as catalyst in DMF (5 mL) and $Et_3N$ (5 mL) as solvent at 85° C. for 18 h to yield rac-(Z)-1,3-Dihydro-5-fluoro-4-(3-hydroxy-1-pentynyl)-3-[(3-methoxy-1H-pyrrol-2-yl)methylene]-2H-indol-2-one. (Yield 56 mg, 64%).

Example 73 rac-(Z)-1,3-Dihydro-5-fluoro-4-(3-hydroxy-1-pentynyl)-3-[(1H-pyrrol-2-yl)methylene]-2H-indol-2-one (NNN)

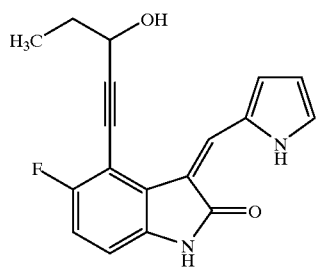

Using Method C above, 1-pentyn-3-ol (58.9 mg, 0.7 mmol) (Aldrich) was coupled with (Z)-1,3-dihydro-5-fluoro-4-iodo-3-[(1H-pyrrol-2-yl)methylene]-2H-indol-2-one (100 mg, 0.28 mmol) (Starting Material 5, supra) using (Ph₃P)₄Pd (32 mg) and CuI (5.3 mg) as catalyst in DMF (5 mL) and Et₃N (5 mL) as solvent at 85° C. for 10 h to yield rac-(Z)-1,3-Dihydro-5-fluoro-4-(3-hydroxy-1-pentynyl)-3-[(1H-pyrrol-2-yl)methylene]-2H-indol-2-one. (Yield 64 mg, 70%).

Example 74

(Z)-1,3-Dihydro-5-fluoro-4-[3-(N-methylamino)-1-propynyl]-3-[(1H-pyrrol-2-yl)methylene]-2H-indol-2-one (OOO)

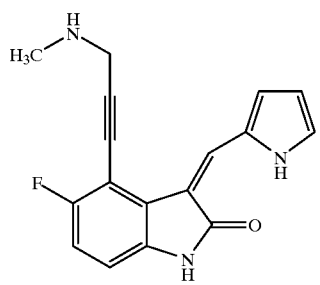

Using Method C above, N-methylpropargylamine (48.4 mg, 0.7 mmol) was coupled with (Z)-1,3-dihydro-5-fluoro-4-iodo-3-[(1H-pyrrol-2-yl)methylene]-2H-indol-2-one (100 mg, 0.28 mmol) (Starting Material 5, supra) using (Ph₃P)₄Pd (32 mg) and CuI (5.3 mg) as catalyst in DMF (5 mL) and Et₃N (5 mL) as solvent at 85° C. for 18 h to yield (Z)-1,3-Dihydro-5-fluoro-4-[3-(N-methylamino)-1-propynyl]-3-[(1H-pyrrol-2-yl)methylene]-2H-indol-2-one. (Yield 10 mg, 12%).

Example 75

(Z)-1,3-Dihydro-5-fluoro-4-[3-(N-methylamino)-1-propynyl]-3-[(3-methoxy-1H-pyrrol-2-yl)methylene]-2H-indol-2-one (PPP)

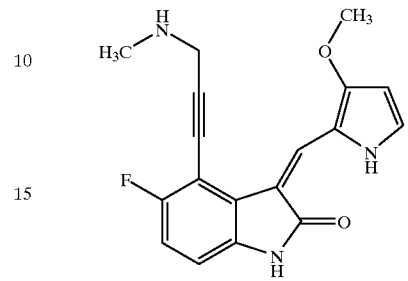

Using Method C above, N-methylpropargylamine (44.9 mg, 0.65 mmol) was coupled with (Z)-1,3-dihydro-5-fluoro-4-iodo-3-[(3-methoxy-1H-pyrrol-2-yl)methylene]-2H-indol-2-one (100 mg, 0.26 mmol) (Starting Material 6, supra) using (Ph₃P)₄Pd (32 mg) and CuI (5.3 mg) as catalyst in DMF (5 mL) and Et₃N (5 mL) as solvent at 85° C. for 18 h to yield (Z)-1,3-Dihydro-5-fluoro-4-[3-(N-methylamino)-1-propynyl]-3-[(3-methoxy-1H-pyrrol-2-yl)methylene]-2H-indol-2-one. (Yield 10 mg, 12%).

Example 76

(Z)-1,3-Dihydro-5-fluoro-4-[3-(N-methylamino)-1-propynyl]-3-[(3-methoxy-1H-pyrrol-2-yl)methylene]-2H-indol-2-one hydrochloride salt (QQQ)

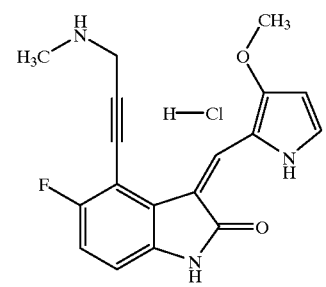

Using Method C above, N-methylpropargylamine (45 mg, 0.66 mmol) was coupled with (Z)-1,3-dihydro-5-fluoro-4-iodo-3-[(3-methoxy-1H-pyrrol-2-yl)methylene]-2H-indol-2-one (100 mg, 0.26 mmol) (Starting Material 6, supra) using (Ph₃P)₄Pd (30.1 mg) and CuI (6.0 mg) as catalyst in DMF (5 mL) and Et₃N (5 mL) as solvent at 80° C. for 5 h to yield (Z)-1,3-Dihydro-5-fluoro-4-[3-(N-methylamino)-1-propynyl]-3-[(3-methoxy-1H-pyrrol-2-yl)methylene]-2H-indol-2-one hydrochloride salt. (Yield 30 mg, 32%). To this free base in methanol (2 mL) was added 4N HCl in dioxane (0.02 mL) (Aldrich). Mixture was evaporated to dryness to give the hydrochloride salt.

Example 77

(R)-(Z) 1,3-Dihydro-5-fluoro-4-(3-hydroxy-1-butynyl)-3-[(4-methyl-1H-imidazol-5-yl)methylene]-2H-indol-2-one (RRR)

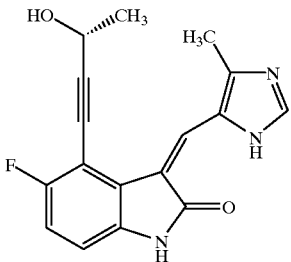

Using Method C above, (R)-But-3-yn-2-ol (189 mg, 2.71 mmol) (Aldrich) was coupled with (Z)-1,3-dihydro-5-fluoro-4-iodo-3-[(4-methyl-1H-imidazol-5-yl)methylene]-2H-indol-2-one (100 mg, 0.27 mmol) (Starting Material 3 supra) using (Ph$_3$P)$_4$Pd (30 mg, 0.03 mmol) and CuI (2 mg) in a mixture of DMF (5 mL) and Et$_3$N (5 mL) as solvent at 80° C. for 4 hrs. Upon completion, the reaction mixture was diluted with EtOAc and extracted with H$_2$O. The organic layer was dried over Na$_2$SO$_4$ and concentrated. (R)-(Z)-1,3-Dihydro-5-fluoro-4-(3-hydroxy-1-butynyl)-3-[(4-methyl-1H-imidazol-5-yl)methylene]-2H-indol-2-one was obtained after silica gel column chromatography with a 0–10% MeOH in CH$_2$Cl$_2$ gradient and trituration with Et$_2$O. (Yield 40 mg, 47%).

Example 78

(R)-(Z)-1,3-Dihydro-5-fluoro-4-(4-hydroxy-1-pentynyl)-3-[(3-methoxy-1H-pyrrol-2-yl)methylene]-2H-indol-2-one (SSS)

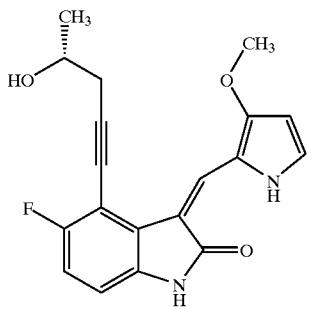

Using Method C above, (R)-pent-4-yn-2-ol (44 mg, 0.52 mmol) (see below) was coupled with (Z)-1,3-dihydro-5-fluoro-4-iodo-3-[(3-methoxy-1H-pyrrol-2-yl)methylene]-2H-indol-2-one (50 mg, 0.13 mmol) (Starting Material 6) using (Ph$_3$P)$_4$Pd (15 mg, 0.01 mol) and CuI (2 mg) in a mixture of DMF (5 mL) and Et$_3$N (5 mL) as solvent at 80° C. for 7 hrs. Upon completion, the reaction mixture was diluted with EtOAc and extracted with H$_2$O. The organic layer was dried over Na$_2$SO$_4$ and concentrated. (R)-(Z)-1,3-Dihydro-5-fluoro-4-(4-hydroxy-1-pentynyl)-3-[(3-methoxy-1H-pyrrod-2-yl)methylene]-2H-indol-2-one was obtained after silica gel column chromatography with a 0–70% EtOAc in hexanes gradient and trituration with Et$_2$O. (Yield 20 mg, 45%).

The optically active (R)-pent-4-yn-2-ol was prepared according to the procedure of C. Dimitriadis, *Tetrahedron Asymmetry*, 1997, 8, 2153.

Example 79

(Z)-5-[2,3-Dihydro-5-fluoro-3-[(3-methoxy-1H-pyrrol-2-yl)methylene]-2-oxo-1H-indol-4-yl]-4-pentynoic acid methyl ester (TTT)

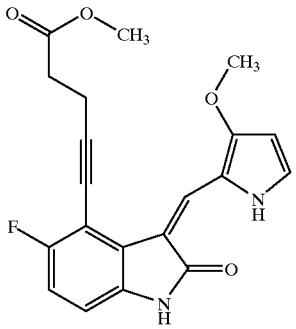

Using Method C above, 4-pentynoic acid methyl ester (75.7 mg, 0.68 mmol) (see Example 8, supra) was coupled with (Z)-1,3-dihydro-5-fluoro-4-iodo-3-[(3-methoxy-1H-pyrrol-2-yl)methylene)]-2H-indol-2-one (100 mg, 0.26 mmol) (Starting Material 6, supra) using (Ph$_3$P)$_4$Pd (31.2 mg) and CuI (5.0 mg) as catalyst in DMF (4 mL) and Et$_3$N (4 mL) as solvent at 80° C. for 7 h to yield (Z)-5-[2,3-Dihydro-5-fluoro-3-[(3-methoxy-1H-pyrrol-2-yl)methylene]-2-oxo-1H-indol-4-yl]-4-pentynoic acid methyl ester. (Yield 86 mg, 90%).

Example 80

(Z)-1,3-Dihydro-5-fluoro-4-[(1-hydroxycyclopentyl)ethynyl]-3-[(3-methoxy-1H-pyrrol-2-yl)methyiene]-2H-indol-2-one (UUU)

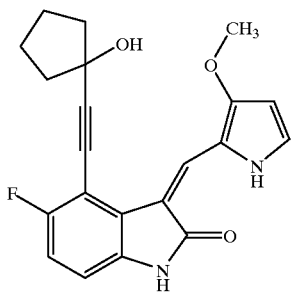

Using Method C above, 1-ethynyl-1-cyclopentanol (35.8 mg, 0.33 mmol) (Aldrich) was coupled with (Z)-1,3-dihydro-5-fluoro-4-iodo-3-[(3-methoxy-1H-pyrrol-2-yl)methylene]-2H-indol-2-one (50 mg, 0.13 mmol) (Starting Material 6) using (Ph$_3$P)$_4$Pd (15 mg) and CuI (2.5 mg) as catalyst in DMF (4 mL) and Et$_3$N (4 mL) as solvent at 80° C. for 5 h to yield (Z)-1,3-Dihydro-5-fluoro-4-[(1-hydroxycyclopentyl)ethynyl]-3-[(3-methoxy-1H-pyrrol-2-yl)methylene]-2H-indol-2-one. (Yield 32 mg, 67%).

Example 81

(S)-(Z)-1,3-Dihydro-5-fluoro-4-(4-hydroxy-1-pentynyl)-3-[(3-methoxy-1H-pyrrol-2-yl)methylene]-2H-indol-2-one (VVV)

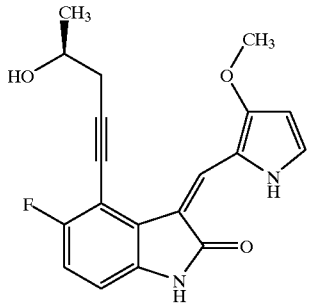

Using Method C above, (S)-pent-4-yn-2-ol (44 mg, 0.52 mmol) (see below) was coupled with (Z)-1,3-dihydro-5-fluoro-4-iodo-3-[(3-methoxy-1H-pyrrol-2-yl)methylene]-2H-indol-2-one (50 mg, 0.13 mmol) (Starting Material 6) using (Ph$_3$P)$_4$Pd (15 mg, 0.01 mmol) and CuI (2 mg) in a mixture of DMF (5 mL) and Et$_3$N (5 mL) as a solvent at 80° C. for 7 hrs. Upon completion, the reaction mixture was diluted with EtOAc and extracted with H$_2$O. The organic layer was dried over Na$_2$SO$_4$ and concentrated. (S)-(Z)-1,3-Dihydro-5-fluoro-4-(4-hydroxy-1-pentynyl)-3-[(3-methoxy-1H-pyrrol-2-yl)methylene]-2H-indol-2-one was obtained after silica gel column chromatography with a 0–70% EtOAc in hexanes gradient and trituration with Et$_2$O. (Yield 30 mg, 65%).

The optically active (S)-pent-4-yn-2-ol was prepared according to the procedure of C. Dimitriadis, *Tetrahedron Asymmetry*, 1997, 8, 2153.

Example 82

(R)-(Z)-1,3-Dihydro-5-fluoro-4-(3-hydroxy-1-butynyl)-3-[(3-methoxy-1H-pyrrol-2-yl)methylene]-2H-indol-2-one (WWW)

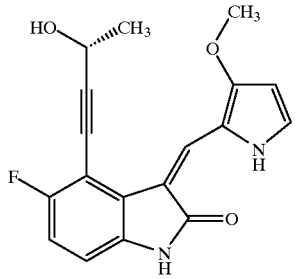

Using Method C above, (R)-but-3-yn-2-ol (37 mg, 0.53 mmol) (Aldrich) was coupled with (Z)-1,3-dihydro-5-fluoro-4-iodo-3-[(3-methoxy-1H-pyrrol-2-yl)methylene]-2H-indol-2-one (50 mg, 0.13 mmol) (Starting Material 6) using (Ph$_3$P)$_4$Pd (15 mg, 0.01 mmol) and CuI (2 mg) in a mixture of DMF (3 mL) and Et$_3$N (3 mL) as solvent at 80° C. for 6 hrs. Upon completion, the reaction mixture was diluted with EtOAc and extracted with H$_2$O. The organic layer was dried over Na$_2$SO$_4$ and concentrated. (R)-(Z)-1,3-Dihydro-5-fluoro-4-(3-hydroxy-1-butynyl)-3-[(3-methoxy-1H-pyrrol-2-yl)methylene]-2H-indol-2-one was obtained after a silica gel column with a 0–70% EtOAc in hexanes gradient and trituration with petroleum ether. (Yield 21 mg, 48%).

Example 83

(S)-(Z)-1,3-Dihydro-5-fluoro-4-(3-hydroxy-1-butynyl)-3-[(3-methoxy-1H-pyrrol-2-yl)methylene]-2H-indol-2-one (XXX)

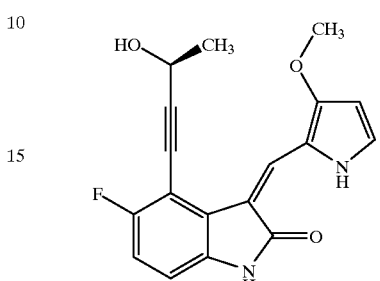

Using Method C above, (S)-but-3-yn-2-ol (36 mg, 0.53 mmol) (Aldrich) was coupled with (Z)-1,3-dihydro-5-fluoro-4-iodo-3-[(3-methoxy-1H-pyrrol-2-yl)methylene]-2H-indol-2-one (50 mg, 0.13 mmol) (Starting Material 6) using (Ph$_3$P)$_4$Pd (15 mg, 0.01 mmol) and CuI (2 mg) in a mixture of DMF (3 mL) and Et$_3$N (3 mL) as solvent at 80° C. for 5 hrs. Upon completion, the reaction mixture was diluted with EtOAc and extracted with H$_2$O. The organic layer was dried over Na$_2$SO$_4$ and concentrated. (S)-(Z)-1,3-Dihydro-5-fluoro-4-(3-hydroxy-1-butynyl)-3-[(3-methoxy-1H-pyrrol-2-yl)methylene]-2H-indol-2-one was obtained after silica gel column chromatography with a 0–70% EtOAc in hexanes gradient and trituration with petroleum ether. (Yield 32 mg, 75%).

Example 84

(S)-(Z)-1,3-Dihydro-5-fluoro-4-(3-hydroxy-1-butynyl)-3-[(4-methyl-1H-imidazol-5-yl)methylene]-2H-indol-2-one (YYY)

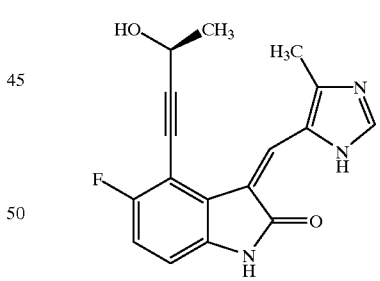

Using Method C above, (S)-but-3-yn-2-ol (38 mg, 0.54 mmol) (Aldrich) was coupled with (Z)-1,3-dihydro-5-fluoro-4-iodo-3-[(4-methyl-1H-imidazol-5-yl)methylene]-2H-indol-2-one (50 mg, 0.14 mmol) (Starting Material 3 supra) using (Ph$_3$P)$_4$Pd (16 mg, 0.01 mmol) and CuI (2 mg) in a mixture of DMF (3 mL) and Et$_3$N (3 mL) as solvent at 80° C. for 5 hrs. Upon completion, the reaction mixture was diluted with EtOAc and extracted with H$_2$O. The organic layer was dried over Na$_2$SO$_4$ and concentrated. (S)-(Z)-1,3-Dihydro-5-fluoro-4-(3-hydroxy-1-butynyl)-3-[(4-methyl-1H-imidazol-5-yl)methylene]-2H-indol-2-one was obtained after silica gel column with a 0–10% MeOH in CH$_2$Cl$_2$ gradient and trituration with Et$_2$O. (Yield 21 mg, 50%).

Example 85A

4-Ethynyl-tetrahydro-pyran-4-ol

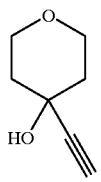

A solution of ethynylmagnesium chloride in THF (0.5 M, 120 mL, 60 mmol) was added with cooling in an ice-water bath to a solution of tetrahydro-4H-pyran-4-one (4.96 g, 50 mmol) (Aldrich) in diethyl ether (300 mL) dropwise over 15 min. The mixture was stirred with cooling for 3 h. Aqueous ammonium chloride solution (100 mL, 15% W/V) was then added and mixture extracted with ether (2×200 mL). The ether layers were washed with saturated aqueous sodium chloride solution (200 mL), then combined, dried (MgSO$_4$), filtered and concentrated to give 4-Ethynyl-tetrahydro-pyran-4-ol as a colorless oil that solidified on standing. (Yield 6.01 g, 96.2%).

Example 85B (Z)-1,3-Dihydro-5-fluoro-4-[(4-hydroxy-tetrahydro-pyran-4-yl)ethynyl]-3-[(3-methoxy-1H-pyrrol-2-yl)methylene]-2H-indol-2-one (ZZZ)

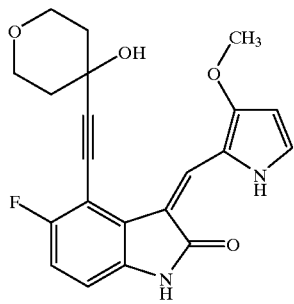

Using Method C above, 4-ethynyl-tetrahydro-pyran-4-ol (41.1 mg, 0.33 mmol) (Example 85A) was coupled with (Z)-1,3-dihydro-5-fluoro-4-iodo-3-[(3-methoxy-1H-pyrrol-2-yl)methylene]-2H-indol-2-one (50 mg, 0.13 mmol) (Starting Material 6) using (Ph$_3$P)$_4$Pd (15 mg) and CuI (2.5 mg) as catalyst in DMF (4 mL) and Et$_3$N (4 mL) as solvent at 85° C. for 7 h to yield (Z)-1,3-Dihydro-5-fluoro-4-[(4-hydroxy-tetrahydro-pyran-4-yl)ethynyl]-3-[(3-methoxy-1H-pyrrol-2-yl)methylene]-2H-indol-2-one. (Yield 36 mg, 75%).

Example 86

(Z)-1,3-Dihydro-4-[(4-hydroxy-tetrahydro-pyran-4-yl)ethynyl]-3-[(3-methoxy-1H-pyrrol-2-yl)methylene]-5-nitro-2H-indol-2-one (AAAA)

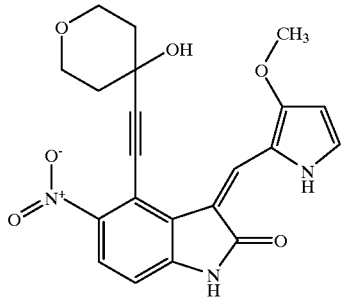

Using Method C above, 4-ethynyl-tetrahydro-pyran-4-ol (43.3 mg, 0.34 mmol) (Example 85A) was coupled with (Z)-1,3-dihydro-4-bromo-3-[(3-methoxy-1H-pyrrol-2-yl)methylene]-5-nitro-2H-indol-2-one (50 mg, 0.14 mmol) (Starting Material 7) using (Ph$_3$P)$_4$Pd (16 mg) and CuI (3.0 mg) as catalyst in DMF (4 mL) and Et$_3$N (4 mL) as solvent at 85° C. for 18 h to give (Z)-1,3-Dihydro-4-[(4-hydroxy-tetrahydro-pyran-4-yl)ethynyl]-3-[(3-methoxy-1H-pyrrol-2-3-yl)methylene]-5-nitro-2H-indol-2-one. (Yield 30 mg, 53%).

Example 87A (S)-N-Boc-2-Formyl-pyrrolidine

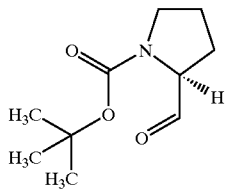

(S)-N-Boc-2-Formyl-pyrrolidine was prepared by Swern oxidation of (S)-N-Boc prolinol (Fluka) according to the conditions described by M. G. B. Drew et al., *J. Chem. Soc. Perkin* 1, 1998, 1627, for the oxidation of CBZ-prolinol.

Example 87B (S)-N-Boc-2-Ethynyl-pyrrolidine

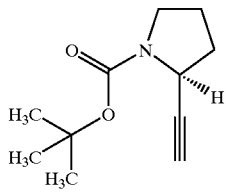

(S)-N-Boc-2-Ethynyl-pyrrolidine was prepared according to Method X above by the treatment of (S)-N-Boc-2-formyl-pyrrolidine (470 mg, 2.36 mmol) (Example 87A above) with potassium tert-butoxide (340 mg, 3.07 mmol) and diazomethyl-phosphonic-acid-diethylester (550 mg, 3.07 mmol) (also prepared according to Method X). The product was obtained after silica gel column chromatography with 10% $Et_2O$ in hexanes. (Yield 200 mg, 43%).

Example 87C (S)-(Z)-1,3-Dihydro-5-fluoro-3-[(3-methoxy-1H-pyrrol-2-yl)methylene]-4-[(pyrrolidin-2-yl)ethynyl]-2H-indol-2-one (BBBB)

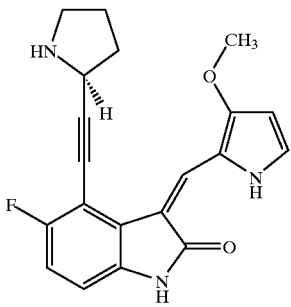

Using Method C above, (S)-N-Boc-2-ethynyl-pyrrolidine (100 mg, 0.52 mmol) (Example 87B) was coupled with (Z)-1,3-dihydro-5-fluoro-4-iodo-3-[(3-methoxy-1H-pyrrol-2-yl)methylene]-2H-indol-2-one (50 mg, 0.13 mmol) (Starting Material 6) using $(Ph_3P)_4Pd$ (15 mg, 0.01 mmol) and a catalytic amount of CuI in a mixture of DMF (4 mL) and $Et_3N$ (4 mL) as solvent at 80° C. for 4 hrs. Upon completion, the reaction mixture was diluted with EtOAc and extracted with $H_2O$. The organic layer was dried over $Na_2SO_4$, concentrated and the residue was chromatographed on a silica gel column with a 40–70% EtOAc in hexanes gradient. The intermediate that was obtained from this operation was directly dissolved at 0° C., in 5 mL of a solution of 50% trifluoroacetic acid in $CH_2Cl_2$ that contained 0.2 mL of $H_2O$ and stirred for 2.5 hrs. Upon completion, the reaction mixture was diluted with EtOAc and extracted with ammonium hydroxide. The organic layer was dried over $Na_2SO_4$ and concentrated. (S)-(Z)-1,3-Dihydro-5-fluoro-3-[(3-methoxy-1H-pyrrol-2-yl)methylene]-4-[(pyrrolidin-2-yl)ethynyl]-2H-indol-2-one was obtained after reverse phase column chromatography with 0–90% MeOH in $H_2O$ gradient, a silica gel column chromatography with neat THF and a precipitatiion out of THF with excess of hexanes. (Yield 8 mg, 18%).

Example 88

(S)-(Z)-1,3-Dihydro-5-fluoro-3-[(3-methoxy-1H-pyrrol-2-yl)methylene]-4-[(pyrrolidin-2-yl)ethynyl]-2H-indol-2-one hydrochloride salt (CCCC)

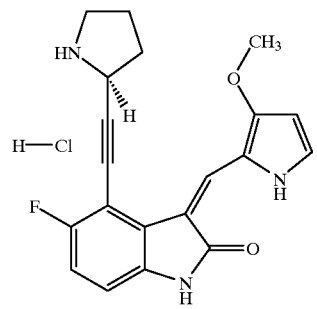

A solution of (S)-(Z)-1,3-dihydro-5-fluoro-3-[(3-methoxy-1H-pyrrol-2-yl)methylene]-4-[(pyrrolidin-2-yl)ethynyl]-2H-indol-2-one (20 mg, 0.06 mmol) (Compound BBBB) in dioxane (2 mL) was treated with aqueous HCl under vigorous stirring. The hydrochloride salt was obtained upon lyophilization. (Yield 20 mg, 86%).

Example 89A (R)-N-Boc-2-Formyl-pyrrolidine

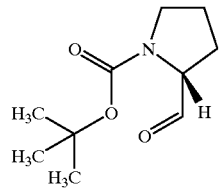

(R)-N-Boc-2-Formyl-pyrrolidine was prepared by Swern oxidation of (R)-N-Boc prolinol (Fluka) using the procedure for the oxidation of CBZ-prolinol described by of M. G. B. Drew et al. supra.

Example 89B (R)-N-Boc-2-Ethynyl-pyrrolidine

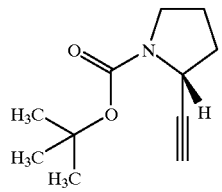

(R)-N-Boc-2-Ethynyl-pyrrolidine was prepared according to Method X above by the treatment of (R)-N-Boc-2-formyl-pyrrolidine (700 mg, 3.51 mmol) (Example 89A) with potassium tert-butoxide (510 mg, 4.56 mmol) and diazomethyl-phosphonic-acid-diethylester (820 mg, 4.56 mmol) (also prepared according to Method X). (R)-N-Boc- 2-Ethynyl-pyrrolidine was obtained after silica gel cotoumn chromatography with 10% Et₂O in hexanes. (Yield 150 mg, 25%).

Example 89C (R)-(Z)-1,3-Dihydro-5-fluoro-3-[(3-methoxy-1H-pyrrol-2-yl)methylene]-4-[(pyrrolidin-2-yl)ethynyl]-2H-indol-2-one (DDDD)

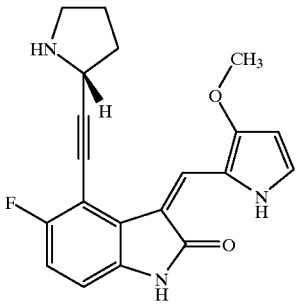

Using Method C above, (R)-N-Boc-2-ethynyl-pyrrolidine (100 mg, 0.52 mmol) (Example 89B) was coupled with (Z)-1,3-dihydro-5-fluoro-4-iodo-3-[(3-methoxy-1H-pyrrol-2-yl)methylene]-2H-indol-2-one (50 mg, 0.13 mmol) (Starting Material 6) using (Ph₃P)₄Pd (15 mg, 0.01 mmol) and a catalytic amount of CuI (2 mg) in a mixture of DMF (4 mL) and Et₃N (4 mL) as solvent at 80° C. for 6 hrs. Upon completion, the reaction mixture was diluted with EtOAc and extracted with H₂O. The organic layer was dried over Na₂SO₄, concentrated and the residue was chromatographed on a silica gel column with a 40–70% EtOAc in hexanes gradient. The intermediate that was obtained from this operation was directly dissolved at 0° C., in 5 mL of a solution of 50% trifluoroacetic acid in CH₂Cl₂ that contained 0.3 mL of H₂O and stirred for 2 hrs. Upon completion, the reaction mixture was diluted with EtOAc and extracted with ammonium hydroxide. The organic layer was dried over Na₂SO₄ and concentrated. (R)-(Z)-1,3-Dihydro-5-fluoro-3-[(3-methoxy-1H-pyrrol-2-yl)methylene]-4-[(pyrrolidin-2-yl)ethynyl]-2H-indol-2-one was obtained after reverse phase column chromatography with 0–90% MeOH in H₂O gradient, a silica gel column chromatography with neat THF and a precipitation out of THF with excess of hexanes. (Yield 14 mg, 31%).

Example 90A

4-Acetyl-2-formylpyrrole

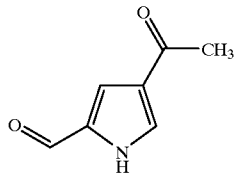

4-Acetyl-2-formylpyrrole was prepared according to the procedure of D. O. Cheng et al., Synthesis of Substituted Porphyrins. *Tetrhedron Letters*, 1977, 1469–1472.

Example 90B (Z)-3-[(4-Acetyl-1H-pyrrol-2-yl)methylene]-1,3-dihydro-5-fluoro-4-iodo-2H-indol-2-one

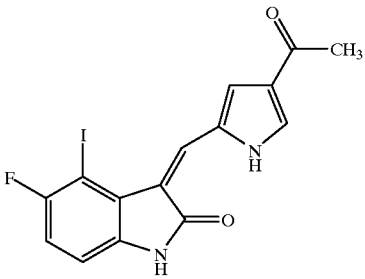

1,3-Dihydro-5-fluoro-4-iodo-2H-indol-2-one (0.77 g, 2.8 mmol) (see Example 2A, supra) and 4-acetyl-2-formylpyrrole (0.42 g, 3.06 mmol) (Example 90A above) were suspended in 1% piperidine in 2-propanol (12 mL) and THF (5 mL) and heated at 85° C. for 2 h. Yellow precipitate was formed. After cooling to room temperature, product was collected by filtration and washed with aqueous 2-propanol and dried in vacuum oven to yield (Z)-3-[(4-Acetyl-1H-pyrrol-2-yl)methylene]-1,3-dihydro-5-fluoro-4-iodo-2H-indol-2-one. (Yield 0.89 g, 80.8%).

Example 90C (Z)-3-[(4-Acetyl-1H-pyrrol-2-yl)methylene]-1,3-dihydro-5-fluoro-4-[(4-hydroxy-tetrahydro-pyran-4-yl)ethynyl]-2H-indol-2-one (EEEE)

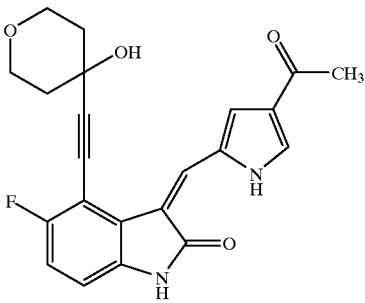

Using Method C above, 4-Ethynyl-tetrahydro-pyran-4-ol (0.16 g, 1.26 mmol) (Example 85A) was coupled with (Z)-3-[(4-acetyl-1H-pyrrol-2-yl)methylene]-1,3-dihydro-5-fluoro-4-iodo-2H-indol-2-one (0.2 g, 0.50 mmol) (Example 90B above) using (Ph₃P)₄Pd (58.4 mg) and CuI (9.6 mg) as catalyst in DMF (15 mL) and Et₃N (15 mL) as solvent at 85° C. for 18 h. (Yield 102 mg, 52%).

Example 91A (R)-N-Boc-2,2-dimethyl-4-ethynyl-oxazolidine

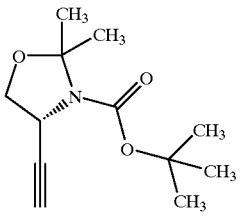

(R)-N-Boc-2,2-dimethyl-4-ethynyl-oxazolidine was prepared according to Method X above by the treatment of tert-butyl-(S)-4-formyl-2,2-dimethyl-3-oxazolidine-carboxylate (1.00 g, 4.36 mmol) (Aldrich) with potassium tert-butoxide (730 mg, 6.54 mmol) and diazomethyl-phosphonic-acid-diethylester (1.20 g, 6.54 mmol) (see Method X, supra). The reaction was allowed to slowly warm up to room temperature and stirred for a total of 12 hrs. The product was obtained after silica gel column chromatography with 20% $Et_2O$ in hexanes. (Yield 600 mg, 61%).

Example 91B (R)-(Z)-4-(3-Amino-4-hydroxy-1-butynyl)-1,3-dihydro-5-fluoro-3-[(3-methoxy-1H-pyrrol-2-yl)methylene]-2H-indol-2-one (FFFF)

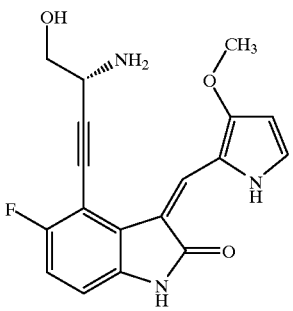

Using Method C above, (R)-N-Boc-2,2-dimethyl-4-ethynyl-oxazolidine (141 mg, 0.62 mmol) (Example 91A above) was coupled with (Z)-1,3-dihydro-5-fluoro-4-iodo-3-[(3-methoxy-1H-pyrrol-2-yl)methylene]-2H-indol-2-one (80 mg, 0.21 mmol) (Starting Material 6) using $(Ph_3P)_4Pd$ (24 mg, 0.02 mmol) and a catalytic amount of CuI in a mixture of DMF (4 mL) and $Et_3N$ (4 mL) as solvent at 80° C. for 8.5 hrs. Upon completion, the reaction mixture was diluted with EtOAc and extracted with $H_2O$. The organic layer was dried over $Na_2SO_4$, concentrated and the residue was chromatographed on a silica gel column with a 0–50% THF in hexanes gradient. The intermediate that resulted from this operation was directly dissolved in 6 mL of a 50% trifluoroacetic acid in $CH_2Cl_2$ solution that contained 0.6 mL of $H_2O$ at 0° C. and stirred for 2 hrs. Upon completion, the reaction mixture was diluted with EtOAc and extracted with ammonium hydroxide. The organic layer was dried over $Na_2SO_4$ and concentrated. (R)-(Z)-4-(3-Amino-4-hydroxy-1-butynyl)-1,3-dihydro-5-fluoro-3-[(3-methoxy-1H-pyrrol-2-yl)methylene]-2H-indol-2-one was obtained after silica gel column chromatography with 0–20% MeOH in $CH_2Cl_2$ gradient and precipitation out of THF with excess pentane. (Yield 10 mg, 14%).

Example 92A (R)-3-Hydroxy-1-prop-2-ynyl-pyrrolidine

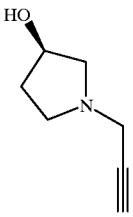

To a solution of (R)-3-hydroxy-pyrrolidine (2.00 g, 22.95 mmol) (Aldrich) and $Et_3N$ (9.00 g, 88.93 mmol) in 45 mL of $CH_2Cl_2$ at 0° C. it was added propargyl bromide (3.00 g, 25.21 mmol) in a dropwise manner. Upon completion of the addition, the reaction mixture was filtered and the filtrate was washed with brine, dried over $Na_2SO_4$ and concentrated. (R)-3-Hydroxy-1-prop-2-ynyl-pyrrolidine was obtained after Krugerhor distitation (Yield 700 mg, 24%).

Example 92B (R)-(Z)-1,3-Dihydro-5-fluoro-4-[3-(3-hydroxy-pyrrolidin-1-yl)-1-propynyl]-3-[(3-methoxy-1H-pyrrol-2-yl)methylene]-2H-indol-2-one (GGGG)

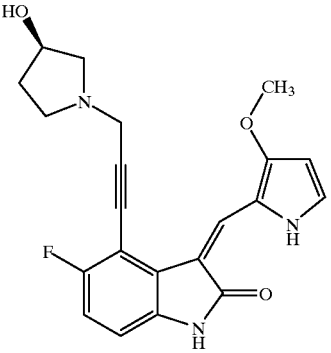

Using Method C above, (R)-3-Hydroxy-1-prop-2-ynyl-pyrrolidine (60 mg, 0.48 mmol) (Example 92A) was coupled with (Z)-1,3-dihydro-5-fluoro-4-iodo-3-[(3-methoxy-1H-pyrrol-2-yl)methylene]-2H-indol-2-one (60 mg, 0.16 mmol) (Starting Material 6) using $(Ph_3P)_4Pd$ (18 mg, 0.02 mmol) and a catalytic amount of CuI in a mixture of DMF (4 mL) and $Et_3N$ (4 mL) as solvent at 80° C. for 6 hrs. Upon completion, the reaction mixture was diluted with EtOAc and extracted with $H_2O$. The organic layer was dried over $Na_2SO_4$ and concentrated. (R)-(Z)-1,3-Dihydro-5-fluoro-4-[3-(3-hydroxy-pyrrolidin-1-yl)-1-propynyl]-3-[(3-methoxy-1H-pyrrol-2-yl)methylene]-2H-indol-2-one was obtained after silica gel column chromatography with a 0–20% MeOH in $CH_2Cl_2$ gradient and precipitation out of THF with excess of pentane. (Yield 45 mg, 76%).

Example 93A (S)-N-Boc-2,2-dimethyl-4-ethynyl-oxazolidine

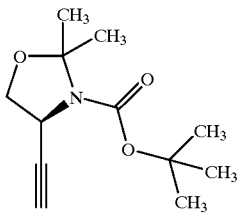

(S)-N-Boc-2,2-dimethyl-4-ethynyl-oxazolidine was prepared according to Method X above by the treatment of tert-butyl-(R)-4-formyl-2,2-dimethyl-3-oxazolidine-carboxylate (1.00 g, 4.36 mmol) (Aldrich) with potassium tert-butoxide (730 mg, 6.54 mmol) and diazomethyl-phosphonic-acid-diethylester (1.20 g, 6.54 mmol) (Method X above). The reaction was allowed slowly to warm up to room temperature and stirred for a total of 12 hrs. (S)-N-Boc-2,2-dimethyl-4-ethynyl-oxazolidine was obtained after silica gel column chromatography with 20% Et$_2$O in hexanes. (Yield 420 mg, 43%).

Example 93B (S)-(Z)-4-(3-Amino-4-hydroxy-1-butynyl)-1,3-dihydro-5-fluoro-3-[(3-methoxy-1H-pyrrol-2-yl)methylene]-2H-indol-2-one (HHHH)

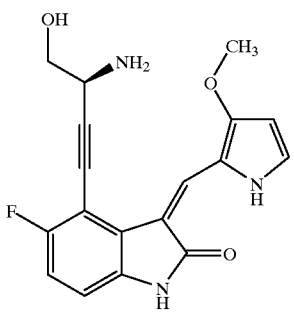

Using Method C above, (S)-N-Boc-2,2-dimethyl-4-ethynyl-oxazolidine (140 mg, 0.62 mmol) (Example 93A above) was coupled with (Z)-1,3-dihydro-5-fluoro-4-iodo-3-[(3-methoxy-1H-pyrrol-2-yl)methylene]-2H-indol-2-one (80 mg, 0.21 mmol) (Starting Material 6) using (Ph$_3$P)$_4$Pd (24 mg, 0.02 mmol) and a catalytic amount of CuI in a mixture of DMF (5 mL) and Et$_3$N (5 mL) as solvent at 80° C. for 6 hrs. Upon completion, the reaction mixture was diluted with EtOAc and extracted with H$_2$O. The organic layer was dried over Na$_2$SO$_4$, concentrated and the residue was chromatographed on a silica gel column with a 0–50% THF in hexanes gradient. The intermediate that was obtained from this operation was directly dissolved in 5 mL of a 50% trifluoroacetic acid in CH$_2$Cl$_2$ solution that contained 0.5 mL of H$_2$O at 0° C. and stirred for 2 hrs. Upon completion, the reaction mixture was diluted with EtOAc and extracted with ammonium hydroxide. The organic layer was dried over Na$_2$SO$_4$ and concentrated. (S)-(Z)-4-(3-Amino-4-hydroxy-1-butynyl)-1,3-dihydro-5-fluoro-3-[(3-methoxy-1H-pyrrol-2-yl)methylene]-2H-indol-2-one was obtained after silica gel column chromatography with 0–20% MeOH in CH$_2$Cl$_2$ gradient and precipitation out of THF with excess of pentane. (Yield 22 mg, 31%).

Example 94

(Z)-3-[(4-Acetyl-1H-pyrrol-2-yl)methylene]-1,3-dihydro-5-fluoro-4-[3-(N-methylamino)-1-propynyl]-2H-indol-2-one (IIII)

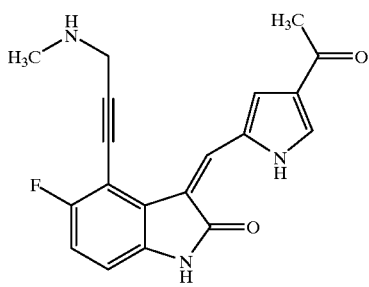

Using Method C above, N-methylpropargylamine (43.6 mg, 0.66 mmol) was coupled with (Z)-3-[(4-acetyl-1H-pyrrol-2-yl)methylene]-1,3-dihydro-5-fluoro-4-iodo-2H-indol-2-one (100 mg, 0.25 mmol) (Example 90B) using (Ph$_3$P)$_4$Pd (30.1 mg) and CuI (6.0 mg) as catalyst in DMF (6 mL) and Et$_3$N (6 mL) as solvent at 89° C. for 5 h to yield (Z)-3-[(4-Acetyl-1H-pyrrol-2-yl)methylene]-1,3-dihydro-5-fluoro-4-[3-(N-methylamino)-1-propynyl]-2H-indol-2-one. (Yield 10 mg, 12%).

Example 95A

N-Boc-N-methylpropargylamine

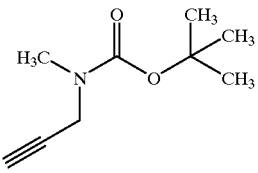

Di-tert-butyl dicarbonate (2.27 g, 10.4 mmol) in dichloromethane (10 mL) was added dropwise to a solution of N-methylpropargylamine (0.72 g, 10.4 mmol) in dichloromethane (25 mL) at room temperature with magnetic stirring. After 1 h, reaction mixture was diluted with dichloromethane and washed with aqueous 1N hydrochloric acid (30 mL) and saturated aqueous sodium bicarbonate solution (30 mL). Aqueous layers were washed with dichloromethane (50 mL). The dichloromethane solutions were combined, dried, (MgSO$_4$), filtered and concentrated. The residue was purified by flash chromatography (Biotage 40S, EtOAc-hexanes V/V 1:9 as solvent) to give N-Boc-N-methylpropargylamine. (Yield 1.54 g, 87.4%).

Example 95B (Z)-3-[(4-Acetyl-1H-pyrrol-2-yl)methylene]-1,3-dihydro-5-fluoro-4-[3-(N-methylamlno)-1-propynyl]-2H-indol-2-one hydrochloride salt (JJJJ)

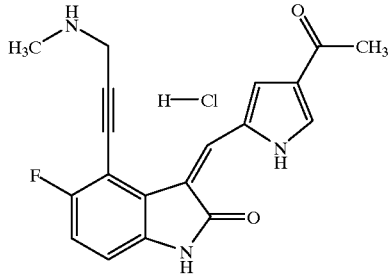

Using Method C above, N-Boc-N-methylpropargylamine (0.12 g, 0.70 mmol) (Example 95A above) was coupled with (Z)-3-[(4-acetyl-1H-pyrrol-2-yl)methylene]-1,3-dihydro-5-fluoro-4-iodo-2H-indol-2-one (0.1 g, 0.25 mmol) (Example 90B) using $(Ph_3P)_4Pd$ (40 mg) and CuI (8.0 mg) as catalyst in DMF (6 mL) and $Et_3N$ (6 mL) as solvent at 85° C. for 5 h. To the resulting compound in $CH_2Cl_2$ (5 mL) was added a 1:1 mixture of trifluoroacetic acid/$CH_2Cl_2$ (5 mL) and 3 drops of water at 0° C. and the mixture was stirred at 0° C. for 2 h. The mixture was then quenched with conc. $NH_4OH$ (5 mL) and diluted with EtOAc. The organic layer was washed with brine and dried with $MgSO_4$. The product was purified via flash column chromatography (10% MeOH in $CH_2Cl_2$). To the free base in methanol (2 mL) was added 4N HCl in dioxane (0.02 mL). Evaporation of solvent to dryness gave the hydrochloride salt. (Yield 30 mg, 32%).

Example 96A (S)-3-Hydroxy-1-prop-2-ynyl-pyrrolidine

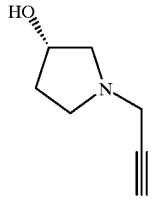

To a solution of (R)-3-hydroxy-1-prop-2-ynyl-pyrrolidine (200 mg, 1.59 mmol) (see Example 92A), benzoic acid (230 mg, 1.91 mmol) (Aldrich) and triphenyl phosphine (628 mg, 2.39 mmol) (Aldrich) in 25 mL of THF, was added diisopropyl azodicarboxylate (485 mg, 2.39 mmol) (Aldrich) at 0° C. The mixture was stirred for 1.25 hr and then partitioned between EtOAc and aqueous saturated $Na_2CO_3$. The organic layer was dried over $Na_2SO_4$, concentrated, and the residue was passed through a silica gel column with a 0–50% EtOAc in hexanes gradient. The resulting intermediate benzoate ester promptly was dissolved in 15 mL of MeOH, and $K_2CO_3$ (439 mg, 3.18 mmol) was added. After stirring for 36 hr, the reaction mixture was filtered and concentrated. (S)-3-Hydroxy-1-prop-2-ynyl-pyrrolidine was obtained after silica gel column chromatography with neat THF and triturating with pentane. (Yield 102 mg, 51%).

Example 96B (S)-(Z)-1,3-Dihydro-5-fluoro-4-[3-(3-hydroxy-pyrrolidin-1-yl)-1-propynyl]-3-[(3-methoxy-1H-pyrrol-2-yl)methylene]-2H-indol-2-one (KKKK)

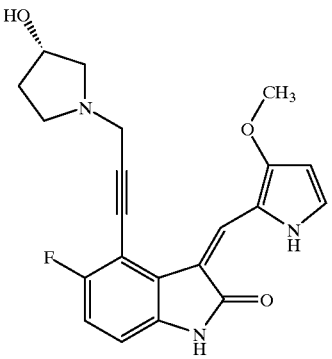

Using Method C above, (S)-3-hydroxy-1-prop-2-ynyl-pyrrolidine (60 mg, 0.48 mmol) (Example 96A) was coupled with (Z)-1,3-dihydro-5-fluoro-4-iodo-3-[(3-methoxy-1H-pyrrol-2-yl)methylene]-2H-indol-2-one (60 mg, 0.16 mmol) (Starting Material 6) using $(Ph_3P)_4Pd$ (18 mg, 0.02 mmol) and a catalylic amount of CuI in a mixture of DMF (4 mL) and $Et_3N$ (4 mL) as solvent at 80° C. for 6 hrs. Upon completion, the reaction mixture was diluted with EtOAc and extracted with $H_2O$. The organic layer was dried over $Na_2SO_4$ and concentrated. (S)-(Z)-1,3-Dihydro-5-fluoro-4-[3-(3-hydroxy-pyrrolidin-1-yl)-1-propynyl]-3-[(3-methoxy-1H-pyrrol-2-yl)methylene]-2H-indol-2-one was obtained after silica gel column chromatography with a 0–20% MeOH in $CH_2Cl_2$ gradient and precipitation out of THF with excess of pentane. (Yield 42 mg, 71%).

Example 97A

N-Boc-3-pyrrolidinone

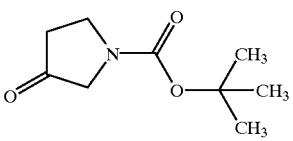

N-Boc-3-pyrrolidinone was prepared according to the procedure of Y. Narukawa et al., 'General and Efficient Synthesis of 2-Alkylcarbapenems: Synthesis of Dethiacarba Analogs of Clinically Useful Carbapenems via Palladium-Catalyzed Cross-Coupling Reaction', Tetrahedron, 1997, 53, 539–556.

Example 97B rac-N-Boc-3-hydroxy-3-ethynyl-pyrrolidine

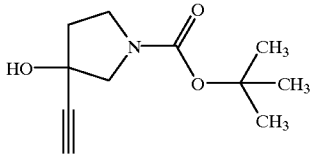

Ethynyl magnesium chloride (0.5 M in THF, 210 mL, 105 mmol) was diluted with THF (100 mL) and cooled in an ice-water bath. A solution of N-Boc-3-pyrrolidinone (9.21 g, 50 mmol) (Example 97A above) in THF (100 mL) was added dropwise with cooling. The mixture was stirred for 2 h and aqueous ammonium chloride solution (100 mL, 15% W/V) was then added. The mixture was then extracted with ether (2×400 mL). The ether layers were washed with saturated aqueous sodium chloride solution (200 mL), combined, dried (MgSO$_4$), filtered and concentrated. The residue was chromatographed (Biotage Flash 40S, EtOAc-hexanes as solvent) to give rac-N-Boc-3-hydroxy-3-ethynyl-pyrrolidine as a pate yellow oil that crystallized on standing. (Yield 10.13 g, 96.4%).

Example 97C rac-3-Hydroxy-3-ethynyl-pyrrolidine

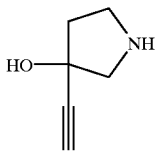

rac-N-Boc-3-hydroxy-3-ethynyl-pyrrolidine (2.02 g, 9.56 mmol) (Example 97B above) was dissolved in CH$_3$CN (20 mL). p-Toluenesulfonic acid monohydrate (3.64 g, 19.12 mmol) was added and mixture stirred at room temperature. The reaction was followed by TLC until no more starting material was observed. Excess solid potassium carbonate was added to remove acid and neutralize the salt. The suspension was filtered and the residue washed with 10% methanol in dichloromethane. The filtrate and the residue wash was combined and concentrated to yield crude product. The crude product was then filtered through a plug of silica gel and eluted with triethylamine-methanol-dichloromethane mixture (1:3:16, V/V/V). The combined etuate was concentrated and crystallized from methanol-dichloromethane-hexanes to give pure rac-3-Hydroxy-3-ethynyl-pyrrolidine as prisms. (0.24 g, yield 22.6%).

Example 97D rac-(Z)-3-[(4-Acetyl-1H-pyrrol-2-yl)methylene]-1,3-dihydro-5-fluoro-4-[(3-hydroxy-pyrrolidin-3-yl)ethynyl]-2H-indol-2-one (LLLL)

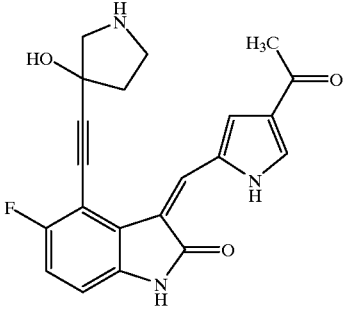

Using Method C above, rac-3-hydroxy-3-ethynyl-pyrrolidine (35.1 mg, 0.32 mmol) (Example 97C) was coupled with (Z)-3-[(4-acetyl-1H-pyrrol-2-yl)methylene]-1,3-dihydro-5-fluoro-4-iodo-2H-indol-2-one (50 mg, 0.13 mmol) (see Example 90B) using (Ph$_3$P)$_4$Pd (15 mg) and CuI (3.0 mg) as catalyst in DMF (3 mL) and Et$_3$N (3 mL) as solvent at 85° C. for 5 h. (Yield 10 mg, 21%).

Example 98 rac-(Z)-3-[(4-Acetyl-1H-pyrrol-2-yl)methylene]-1,3-dihydro-5-fluoro-4-[(3-hydroxy-pyrrolidin-3-yl)ethynyl]-2H-indol-2-one hydrochloride salt (MMMM)

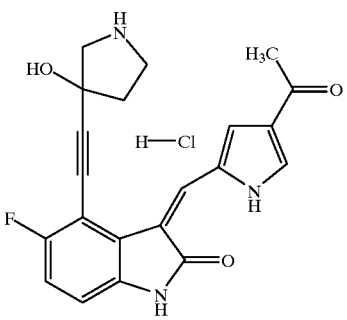

Using Method C above, N-Boc-3-hydroxy-3-ethynyl-pyrrolidine (0.2 g, 0.95 mmol) (Example 97B) was coupled with (Z)-3-[(4-acetyl-1H-pyrrol-2-yl)methylene]-1,3-dihydro-5-fluoro-4-iodo-2H-indol-2-one (0.15 g, 0.38 mmol) (Example 90B) using (Ph$_3$P)$_4$Pd (60 mg) and CuI (13.5 mg) as catalyst in DMF (8 mL) and Et₃N (8 mL) as solvent at 85° C. for 8 h. To the resulting compound in CH₂Cl₂ (6 mL) was added a 1:1 mixture of trifluoroacetic acid/CH₂Cl₂ (6 mL) and 3 drops of water at 0° C. and the mixture was stirred at 0° C. for 3 h. It was quenched with conc. NH₄OH (6 mL) and diluted with EtOAc. The organic layer was washed with brine and dried with MgSO₄. The product was purified via flash column chromatography (10% MeOH in CH₂Cl₂). To the free base in methanol (2 mL) was added 4N HCl in dioxane (0.04 mL). Evaporation of solvent to dryness gave the hydrochloride salt. (Yield 65.6 mg, 41%).

Example 99A (3R,5S)-N-Boc-3-(tert-Butyldimethylsiloxy)-5-hydroxymethylene-pyrrolidine

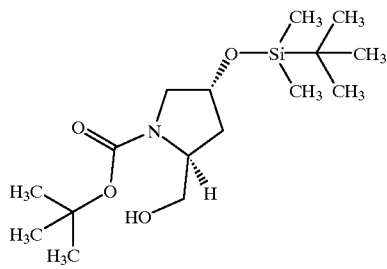

A solution of trans-L-hydroxy-proline (2.00 g, 15.24 mmol) (Aldrich) and imidazole (2.20 g, 32.01 mmol) (Aldrich) in CH₂Cl₂ (60 mL) was treated with tert-butyldimethylsilyl chloride (4.60 g, 30.48 mmol) (Aldrich). After stirring overnight the mixture was poured into brine and extracted with CH₂Cl₂. The organic layer was dried over Na₂SO₄ and concentrated. The residue was then directly-dissolved in 50 mL of MeOH and the resulting solution was heated at reflux for 4.5 hrs and then stirred at room temperature for another 17 hr. The solvent was then evaporated in vacuo and the resulting intermediate was diluted in 60 mL of THF cooled at 0° C. and BF₃.Et₂O (15.30 mmol, 1.92 mL) (Aldrich) and BH₃.DMS (22.90 mmol, 2.30 mL) (Aldrich) were added. The resulting mixture was then heated at reflux for 1.5 hrs, cooled to room temperature, quenched with MEOH, and concentrated. The residue was partitioned between CH₂Cl₂ and ammonium hydroxide. After 4 hrs of vigorous stirring the two layers were separated and the aquous layer was extracted twice more with CH₂Cl₂ and the combined organic layer was dried over Na₂SO₄ and concentrated. The residue was directly dissolved in 35 mL of CH₂Cl₂ and then Et₃N (3.08 g, 30.60 mmol), a catalytic amount of DMAP (Fluka) and di-tert-butyl-dicarbnonate (3.30 g, 15.30 mmol) (Ruka) were added at 0° C. The reaction was slowly allowed to warm up to room temperature, stirred for 2.5 hrs, and then poured in H₂O. The aqueous layer was separated and extracted twice more with CH₂Cl₂ and the combined organic layer was dried over Na₂SO₄ and concentrated. (3R,5S)-N-Boc-3-(tert-Butyldimethylsiloxy)-5-hydroxymethylene-pyrrolidine was obtained after silica gel column chromatography with a 0–50% EtOAc in hexanes gradient. (Yield 2.10 g, 42% overall).

Example 99B (3R,5S)-N-Boc-3-tert-Butyldimethylsiloxy-5-ethynyl-pyrrolidine

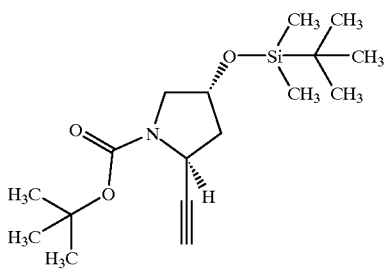

(3R,5S)-N-Boc-3-(tert-Butyldimethylsiloxy)-5-hydroxymethylene-pyrrolidine (1.30 g, 3.92 mmol) (Example 99A above), as a solution in a small volume of CH₂Cl₂, was transferred via cannula under argon to a solution of oxallyl chloride (0.65 g, 5.09 mmol) (Aldrich), DMSO (0.92 g, 11.76 mmol) and Et₃N (1.59 g, 15.68 mmol) in 60 mL of CH₂Cl₂ at −78° C. After 10 min the mixture was poured in H₂O. The aqueous layer was extracted twice more with CH₂Cl₂ and combined CH₂Cl₂ layer was extracted with aqueous saturated solution of NaHCO₃, dried over Na₂SO₄ and evaporated in vacuo. The residue was directly treated according to method X with potassium tert-butoxide (660 mg, 5.88 mmol) and diazomethyl-phosphonic-acid-dimethylester (880 mg, 5.88 mmol) in 60 mL of THF. The reaction was allowed to warm up to room temperature slowly and stirred for a total of 17.5 hrs. (3R,5S)-N-Boc-3-tert-Butyldimethylsiloxy-5-ethynyl-pyrrolidine was obtained after silica gel column chromatography with a 0–20% Et₂O in hexanes gradient. (Yield 720 mg, 56%).

Example 99C (3R,5S)-N-Boc-3-Hydroxy-5-ethynyl-pyrrolidine

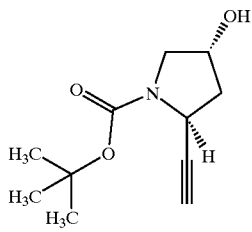

(3R,5S)-N-Boc-3-tert-Butyldimethylsiloxy-5-ethynyl-pyrrolidine (700 mg, 2.15 mmol) (Example 99B above) was

87 dissolved in a mixture of THF (20 mL) and H₂O (1 mL). TBAF (1M in THF) (Aldrich) was added (2.15 mL, 2.15 mmol) at 0° C. and the reaction mixture was allowed slowly to warm up to room temperature. After 21 hr at room temperature and 2 hrs at 50° C. the mixture was concentrated to a small volume diluted with EtOAc and washed with brine. The organic layer was dried over Na₂SO₄ and concentrated. (3R,5S)-N-Boc-3-Hydroxy-5-ethynyl-pyrrolidine was obtained after silica gel column chromatography with a 0–100% EtOAc in hexanes gradient. (Yield 390 mg, 81%).

Example 99D (Z)-1,3-Dihydro-5-fluoro-4-[(2S,4R)-(4-hydroxy-pyrrolidin-2-yl)-ethynyl]-3-[(3-methoxy-1H-pyrrol-2-yl)methylene]-2H-indol-2-one (NNNN)

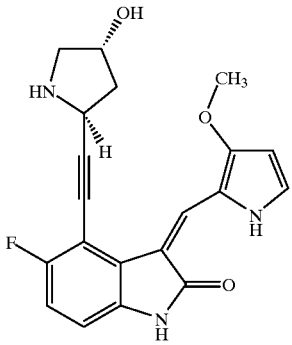

Using Method C above, (3R,5S)-N-Boc-3-Hydroxy-5-ethynyl-pyrrolidine (98 mg, 0.47 mmol) (Example 99C above) was coupled with (Z)-1,3-dihydro-5-fluoro-4-iodo-3-[(3-methoxy-1H-pyrrol-2-yl)methylene]-2H-indol-2-one (60 mg, 0.16 mmol) (Starting Material 6) using (Ph₃P)₄Pd (18 mg, 0.02 mmol) and a catalytic amount of CuI in a mixture of DMF (5 mL) and Et₃N (5 mL) as solvent at 80° C. for 6 hrs. Upon completion, the reaction mixture was diluted with EtOAc and extracted with H₂O. The organic layer was dried over Na₂SO₄, concentrated and the residue was chromatographed on a silica gel column with a 0–100% EtOAc in hexanes gradient. The intermediate that resulted from this operation was directly dissolved in 5 mL of a 50% trifluoroacetic acid in CH₂Cl₂ solution that contained 0.2 mL of H₂O at 0° C. and stirred for 2 hrs. Upon completion, the reaction mixture was diluted with EtOAc and extracted with ammonium hydroxide. The organic layer was dried over Na₂SO₄ and concentrated. (Z)-1,3-Dihydro-5-fluoro-4-[(2S,4R)-(4-hydroxy-pyrrolidin-2-yl)-ethynyl]-3-[(3-methoxy-1H-pyrrol-2-yl)methylene]-2H-indol-2-one was obtained after silica gel column chromatography with 0–20% MeOH in CH₂Cl₂ gradient and precipitation out of THF with excess of pentane. (Yield 12 mg, 31%).

88

Example 100

(Z)-1,3-Dihydro-5-fluoro-4-[(2S,4R)-(4-hydroxy-pyrrolidin-2-yl)-ethynyl]-3-[(3-methoxy-1H-pyrrol-2-yl)methylene]-2H-indol-2-one hydrochloride salt (OOOO)

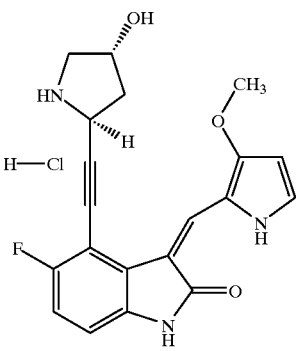

A solution of (Z)-1,3-dihydro-5-fluoro-4-[(2S,4R)-(4-hydroxy-pyrrolidin-2-yl)-ethynyl]-3-[(3-methoxy-1H-pyrrol-2-yl)methylene]-2H-indol-2-one (30 mg, 0.06 mmol) (Example 99D above) in DMF (3 mL) was treated with aqueous HCl under vigorous stirring. The solution was lyophilized and the residue was perceipitated from a mixture of CH₂Cl₂/MeOH (3:1) with excess of pentanes. (Yield 30 mg, 91%).

Example 101A

N-Boc-4-hydroxy-4-ethynyl-piperidine

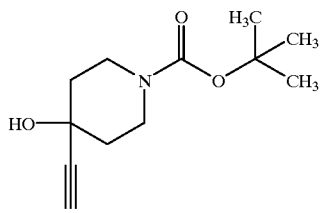

A solution of ethynylmagnesium chloride in THF (100 mL, 50 mmol) was diluted with THF (50 mL) and cooled in an ice-water bath. A solution of Boc-4-piperidone (5.06 g, 25.4 mmol) (Aldrich) in THF (50 mL) was added dropwise over 15 min. The mixture was stirred with cooling for 3 h. Aqueous ammonium chloride solution (100 mL, 15% W/V) was then added and the resulting mixture extracted with ether (2×200 mL). The ether layers were washed with saturated aqueous sodium chloride solution (200 mL), then combined, dried (MgSO₄), filtered and concentrated. The residue was purified by chromatography (Biotage 40M, ethyl acetate-hexanes 1:3, V/V as solvent) to give N-Boc-4-hydroxy-4-ethynyl-piperidine as a colorless oil that solidified on standing. (Yield 5.39 g, 94.2%).

Example 101B (Z)-1,3-Dihydro-5-fluoro-4-[(4-hydroxy-piperidin-4-yl)-ethynyl]-3-[(3-methoxy-1H-pyrrol-2-yl)methylene]-2H-indol-2-one hydrochloride salt (PPPP)

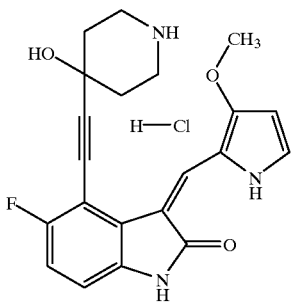

Using Method C above, N-Boc-4-hydroxy-4-ethynyl-piperidine (74.3 mg, 0.33 mmol) (Example 101A above) was coupled with (Z)-1,3-dihydro-5-fluoro-4-iodo-3-[(3-methoxy-1H-pyrrol-2-yl)methylene]-2H-indol-2-one (50 mg, 0.13 mmol) (Starting Material 6) using (Ph₃P)₄Pd (15 mg) and CuI (3 mg) as catalyst in DMF (4 mL) and Et₃N (4 mL) as solvent at 85° C. for 5 h. To the resulting compound in CH₂Cl₂ (5 mL) was added a 1:1 mixture of trifluoroacetic acid/CH₂Cl₂ (5 mL) and 2 drops of water at 0° C. and the mixture was stirred at 0° C. for 1.5 h. The mixture was then quenched with conc. NH₄OH (5 mL) and diluted with EtOAc. The organic layer was washed with brine and dried with MgSO₄. The product was purified via flash column chromatography (20% MeOH in CH₂Cl₂). To free base in methanol (2 mL) was added 4N HCl in dioxane (0.01 mL). Evaporation of solvent to dryness gave the hydrochloride salt. (Yield 12 mg, 24%).

Example 102A (4S,5R)-N-Boc-2,2,5-trimethyl-oxazolidine-4-carbaldehyde

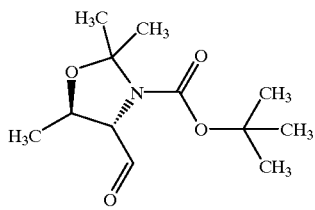

(4S,5R)-N-Boc-2,2,5-trimethyl-oxazolidine-4-carbaldehyde was prepared according to the procedure of P. Garner, The Synthesis and Configurational Stability of Differentially Protected α-Hydroxy-γ-amino Aldehydes. *J. Org. Chem.* 1987, 52, 2361–2364.

Example 102B (4R,5R)-N-Boc-2,2,5-Trimethyl-4-ethynyl-oxazolidine

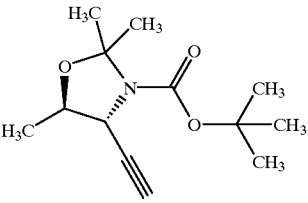

To a solution of (4S,5R)-N-Boc-2,2,5-trimethyl-oxazolidine-4-carbaldehyde (1.52 g, 5.43 mmol) (Example 102A above) and dimethyl(1-diazo-2-oxopropyl) phosphonate (1.57 g, 8.15 mmol) in dry MeOH (30 mL) was added K₂CO₃ at 0° C. The mixture was stirred at 0° C. for 30 min and room temperature for 20 h. After addition of saturated aqueous NH₄Cl and EtOAc, the organic layer was separated and aqueous layer was extracted with EtOAc (3×). The ethyl acetate layers were combined and dried with MgSO₄. The crude material was purified by flash column chromatography eluting with EtOAc/hexanes (1:6) to give (4R,5R)-N-Boc-2,2,5-Trimethyl-4-ethynyl-oxazolidine. (Yield 0.97 g, 65%).

Example 102C (Z)-4-[(3R,4R)-3-Amino-4-hydroxy-1-pentynyl]-1,3-dihydro-5-fluoro-3-[(3-methoxy-1H-pyrrol-2-yl)methylene]-2H-indol-2-one (QQQQ)

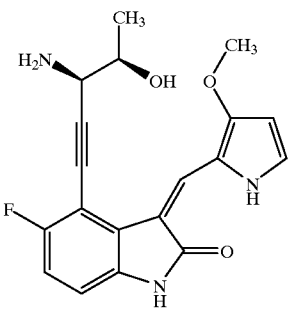

Using Method C above, (4R,5R)-N-Boc-2,2,5-trimethyl-4-ethynyl-oxazolidine (0.18 g, 0.65 mmol) (Example 102B) was coupled with (Z)-1,3-dihydro- 5-fluoro-4-iodo-3-[(3-methoxy-1H-pyrrol-2-yl)methylene]-2H-indol-2-one (0.1 g, 0.26 mmol) (Starting Material 6) using (Ph₃P)₄Pd (30 mg) and CuI (6 mg) as catalyst in DMF (6 mL) and Et₃N (6 mL) as solvent at 85° C. for 1 day. To the resulting compound in CH₂Cl₂ (6 mL) was added a 1:1 mixture of trifluoroacetic acid/CH₂Cl₂ (6 mL) and 3 drops of water at 0° C. and the mixture was stirred at 0° C. for 1.5 h. The mixture was then quenched with conc. NH₄OH (6 mL) and diluted with EtOAc. The organic layer was washed with brine and dried with MgSO₄. (Z)-4-[(3R,4R)-3-Amino-4-hydroxy-1-pentynyl]-1,3-dihydro-5-fLuoro-3-[(3-methoxy-1H-pyrrol-2-yl)methylene]-2H-indol-2-one was purified via flash column chromatography (10% MeOH in CH₂Cl₂). (Yield 44 mg, 48%).

Example 103A (3S,5S)-N-Boc-5-ethynyl-3-hydroxy-pyrrolidine

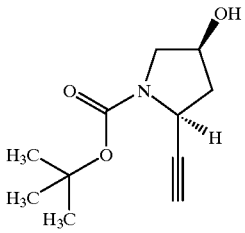

To a solution of (3R,5S)-N-Boc-3-Hydroxy-5-ethynyl-pyrrolidine (200 mg, 0.95 mmol) (Example 99C), benzoic acid (138 mg, 0.11 mmol) and triphenyl phosphine (373 mg, 1.42 mmol) in 15 mL of THF was added diisopropyl azodicarboxylate (287 mg, 1.42 mmol) at 0° C. The mixture was allowed to slowly warm up to room temperature and stirred for 18 hrs. The reaction mixture was then concentrated and the residue was directly passed through a silica gel column with a 0–30% EtOAc in hexanes gradient. The intermediate benzoate ester was dissolved in 6 mL of MeOH and then $K_2CO_3$ (260 mg, 1.89 mmol) was added. The mixture, after overnight stirring, was filtered and concentrated to a residue which after silica gel column chromatography with a 0–70% EtOAc in hexanes gradient afforded (3S,5S)-N-Boc-5-ethynyl-3-hydroxy-pyrrolidine. (Yield 170 mg, 85%).

Example 103B (Z)-1,3-Dihydro-5-fluoro-4-[(2S,4S)-(4-hydroxy-pyrrolidin-2-yl)-ethynyl]-3-[(3-methoxy-1H-pyrrol-2-yl)methylene]-2H-indol-2-one (RRRR)

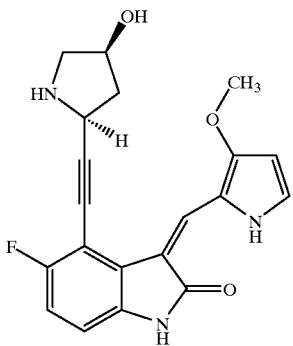

Using Method C above, (3S,5S)-N-Boc-3-Hydroxy-5-ethynyl-pyrrolidine (132 mg, 0.62 mmol) (Example 103A above) was coupled with (Z)-1,3-dihydro-5-fluoro-4-iodo-3-[(3-methoxy-1H-pyrrol-2-yl)methylene]-2H-indol-2-one (80 mg, 0.21 mmol) (Starting Material 6) using $(Ph_3P)_4Pd$ (24 mg, 0.02 mmol) and a catalytic amount of CuI in a mixture of DMF (5 mL) and $Et_3N$ (5 mL) as solvent at 80° C. for 5.5 hrs. Upon completion, the reaction mixture was diluted with EtOAc and extracted with $H_2O$. The organic layer was dried over $Na_2SO_4$, concentrated, and the residue was chromatographed on a silica gel column with a 0–100% EtOAc in hexanes gradient. The resulting intermediate was dissolved in 4 mL of a 50% trifluoroacetic acid in $CH_2Cl_2$ solution that contained 0.2 mL of $H_2O$ at 0° C. and stirred for 2 hrs. Upon completion, the reaction mixture was diluted with EtOAc and extracted with ammonium hydroxide. The organic layer was dried over $Na_2SO_4$ and concentrated. (Z)-1,3-Dihydro-5-fluoro-4-[(2S,4S)-(4-hydroxy-pyrrolidin-2-yl)-ethynyl]-3-[(3-methoxy-1H-pyrrol-2-yl)methylene]-2H-indol-2-one was obtained after silica gel column chromatography with a 0–20% MeOH in $CH_2Cl_2$ gradient and precipitation out of THF with excess of pentane. (Yield 45 mg, 58%).

Example 104A (R)-N-Boc-2-amino-but-3-yn-1-ol

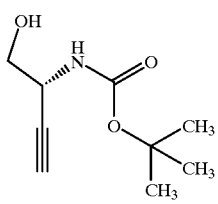

A solution of (R)-N-Boc-2,2-dimethyl-4-ethynyl-oxazolidine (200 mg, 0.89 mmol) (Example 91A above) in a mixture of MeOH (10 mL) and water (1 mL) was treated with p-toluenesulfonic acid monohydrate (16 mg, 0.09 mmol). After stirring at reflux overnight a thermodynamic mixture of starting material and product was obtained (appr. 1:1). The solvent was concentrated and the product was separated from the starting material via silica gel column chromatography with a 0–60–100% EtOAc in hexanes gradient. The recovered starting material was subjected to the above process for two more times yielding (R)-N-Boc-2-amino-but-3-yn-1-ol. (Yield 150 mg, 91%).

Example 104B (R)-N-Boc-2-amino-1-(-tert-butyldimethylsilyloxy)-but-3-yne

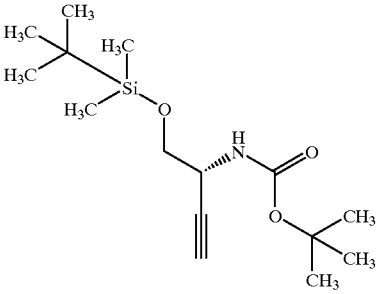

To a solution of (R)-N-Boc-2-amino-but-3-yn-1-ol (150 mg, 0.81 mmol) (Example 104B) and imidazole (110 mg, 1.62 mmol) (Aldrich) in $CH_2Cl_2$ (10 mL) was added at 0° C. tert-butyldimethylsilyl chloride (146 mg, 0.97 mmol) (Fluka). After 5 min the reaction mixture was poured into $H_2O$ and extracted with $CH_2Cl_2$. The $CH_2Cl_2$ layer was dried over $Na_2SO_4$ and concentrated to a residue which after silica gel column chromatography with a 0–30% $Et_2O$ in hexanes gradient afforded the product. (Yield 210 mg, 83%).

Example 104C (R)-2-(N-Boc-N-methylamino)-1-(tert-butyldimethylsilyloxy)-but-3-yne

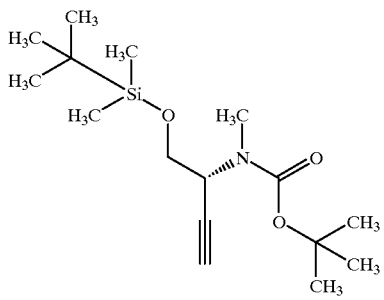

(R)-2-(N-Boc-N-methylamino)-1-(tert-butyldimethylsilyloxy)-but-3-yne was synthesized according to Method Y above by the treatment of (R)-N-Boc-2-amino-1-(-tert-butyldimethylsilyloxy)-but-3-yne (200 mg, 0.67 mmol) (Example 104B) with NaH (21 mg, 0.87 mmol) and MeI (189 mg, 1.34 mmol) in THF (12 mL). The product was obtained after silica gel column chromatography with a 0–10% EtOAc in hexanes gradient. (Yield 200 mg, 95%).

Example 104D (R)-(Z)-1,3-Dihydro-5-fluoro-4-[4-hydroxy-3-methylamino-1-butynyl]-3-[(3-methoxy-1H-pyrrol-2-yl)methylene]-2H-indol-2-one (SSSS)

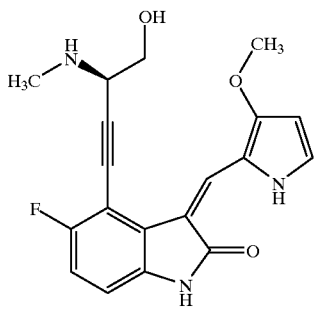

Using Method C above, (R)-2-(N-Boc-N-methylamino)-1-(tert-butyldimethylsilyloxy)-but-3-yne (130 mg, 0.42 mmol) (Example 104C) was coupled with (Z)-1,3-dihydro-5-fluoro-4-iodo-3-[(3-methoxy-1H-pyrrol-2-yl)methylene]-2H-indol-2-one (80 mg, 0.21 mmol) (Starting Material 6) using $(Ph_3P)_4Pd$ (24 mg, 0.02 mmol) and a catalytic amount of CuI in a mixture of DMF (5 mL) and $Et_3N$ (5 mL) as solvent at 80° C. for 5 hrs. Upon completion, the reaction mixture was diluted with EtOAc and extracted with $H_2O$. The organic layer was dried over $Na_2SO_4$, concentrated, and the residue was chromatographed on a silica gel column with a 40–100% EtOAc in hexanes gradient. The intermediate that resulted from this operation was dissolved directly in 10 mL of a 50% trifluoroacetic acid in $CH_2Cl_2$ solution that contained 0.5 mL of $H_2O$ at 0° C. and stirred for 2.5 hrs. Upon completion, the reaction mixture was diluted with EtOAc and extracted with ammonium hydroxide. The organic layer was dried over $Na_2SO_4$ and concentrated. (R)-(Z)-1,3-Dihydro-5-fluoro-4-[4-hydroxy-3-methylamino-1-butynyl]-3-[(3-methoxy-1H-pyrrol-2-yl)methylene]-2H-indol-2-one was obtained after silica gel column chromatography with a 0–10% MeOH in $CH_2Cl_2$ gradient and precipitation out of THF with excess of pentane. (Yield 28 mg, 38%).

Example 105A 4R-(1R-Hydroxy-prop-2-ynyl)-2,2,5R-trimethyl-oxazolidine-3-carboxylic acid tert-butyl ester

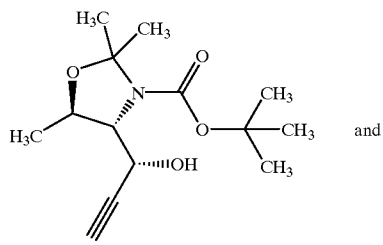

and 4R-(1S-Hydroxy-prop-2-ynyl)-2,2,5R-trimethyl-oxazolidine-3-carboxylic acid tert-butyl ester

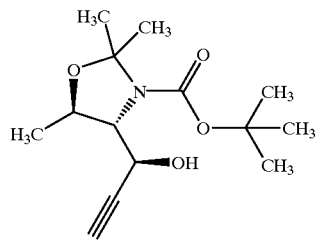

To a solution of ethynylmagnesium chloride (130.8 mL, 0.5M in THF solution, 65.4 mmol) was added (4R,5R)-N-boc-2,2,5-trimethyl-4-ethynyl-oxazolidine (3.0 g, 10.7 mmol) (Example 102A) in THF (20 mL). The mixture was stirred at room temperature for 4.5 h. The reaction was quenched with EtOH (11 mL) and saturated aqueous $NH_4Cl$ (18.4 mL) and stirred at room temperature overnight. The resulting mixture was acidified with aqueous 2N HCl (16 mL). The aqueous layer was extracted with $CH_2Cl_2$ (3×) and the combined organic layers were washed with saturated aqueous $NaHCO_3$, brine and dried with $MgSO_4$. The crude material was purified by flash column chromatography eluting with EtOAc/hexanes (1:6) to give 4R-(1S-hydroxy-prop-2-ynyl)-2,2,5R-trimethyl-oxazolidine-3-carboxylic acid tert-butyl ester (yield 0.86 g, 26%) and 4R-(1R-hydroxy-prop-2-ynyl)-2,2,5R-trimethyl-oxazolidine-3-carboxylic acid tert-butyl ester (yield 1.7 g, 52%).

Example 105B (Z)-4-[(3S,4S,5R)-4-Amino-3,5-dihydroxy-1-hexynyl]-1,3-dihydro-5-fluoro-3-[(3-methoxy-1H-pyrrol-2-yl)methylene]-2H-indol-2-one (TTTT)

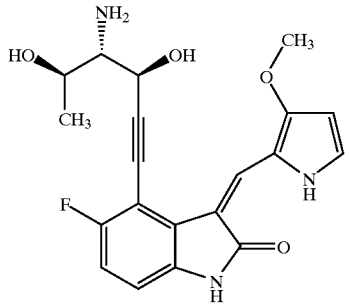

Using Method C above, 4R-(1S-hydroxy-prop-2-ynyl)-2,2,5R-trimethyl-oxazolidine-3-carboxylic acid tert-butyl ester (0.2 g, 0.65 mmol) (Example 105A above) was coupled with (Z)-1,3-dihydro-5-fluoro-4-iodo-3-[(3-methoxy-1H-pyrrol-2-yl)methylene]-2H-indol-2-one (0.1 g, 0.26 mmol) (Starting Material 6) using $(Ph_3P)_4Pd$ (30 mg) (Aldrich) and CuI (6 mg) as catalyst in DMF (5 mL) and $Et_3N$ (5 mL) as solvent at 85° C. for 18 h. To the resulting compound in $CH_2Cl_2$ (10 mL) was added a 1:1 mixture of trifluoroacetic acid/$CH_2Cl_2$ (10 mL) and 5 drops of water at 0° C. and the mixture was stirred at 0° C. for 1.5 h. The mixture was then quenched with conc. $NH_4OH$ (10 mL) and diluted with EtOAc. The organic layer was washed with brine and dried with $MgSO_4$. The product was purified via flash column chromatography (10% MeOH in $CH_2Cl_2$). (Yield 30 mg, 30%).

Example 106

(Z)-4-[(3R,4S,5R)-4-Amino-3,5-dihydroxy-1-hexynyl]-1,3-dihydro-5-fluoro-3-[(3-methoxy-1H-pyrrol-2-yl)methylene]-2H-indol-2-one (UUUU)

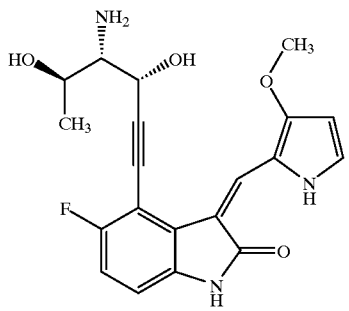

Using Method C above, 4R-(1R-Hydroxy-prop-2-ynyl)-2,2,5R-trimethyl-oxazolidine-3-carboxylic acid tert-butyl ester (0.2 g, 0.65 mmol) (Example 105A above) was coupled with (Z)-1,3-dihydro-5-fluoro-4-iodo-3-[(3-methoxy-1H-pyrrol-2-yl)methylene]-2H-indol-2-one (0.1 g, 0.26 mmol) (Starting Material 6) using $(Ph_3P)_4Pd$ (30 mg) and CuI (6 mg) as catalyst in DMF (5 mL) and $Et_3N$ (5 mL) as solvent at 85° C. for 18 h. To above compound in $CH_2Cl_2$ (10 mL) was added a 1:1 mixture of trifluoroacetic acid/$CH_2Cl_2$ (10 mL) and 5 drops of water at 0° C. and the mixture was stirred at 0° C. for 1.5 h. The mixture was then quenched with conc. $NH_4OH$ (10 mL) and diluted with EtOAc. The organic Layer was washed with brine and dried with $MgSO_4$. The product was purified via flash column chromatography (10% MeOH in $CH_2Cl_2$). (Yield 35 mg, 35%).

Example 107 rac-(Z)-1,3-Dihydro-5-fluoro-4-[(3-hydroxy-pyrrolidin-3-yl)ethynyl]-3-[(3-methoxy-1H-pyrrol-2-yl)methylene]-2H-indol-2-one hydrochloride salt (VVVV)

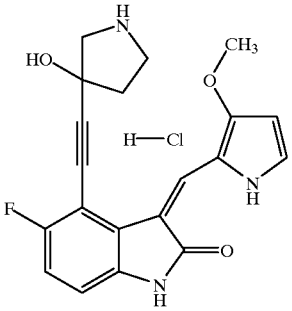

Using Method C above, rac-N-boc-3-hydroxy-3-ethynyl-pyrrolidine (70.7 mg, 0.33 mmol) (see Example 97B) was coupled with (Z)-1,3-dihydro-5-fluoro-4-iodo-3-[(3-methoxy-1H-pyrrol-2-yl)methylene]-2H-indol-2-one (0.10 g, 0.26 mmol) (Starting Material 6) using $(Ph_3P)_4Pd$ (31 mg) and CuI (6.0 mg) as catalyst in DMF (5 mL) and $Et_3N$ (5 mL) as solvent at 85° C. for 1 day. To the resulting compound in $CH_2Cl_2$ (5 mL) was added a 1:1 mixture of trifluoroacetic acid/$CH_2Cl_2$ (5 mL) and 2 drops of water at 0° C. and the mixture was stirred at 0° C. for 1.5 h. The mixture was then quenched with conc. $NH_4OH$ (5 mL) and diluted with EtOAc. The organic layer was washed with brine and dried with $MgSO_4$. The product was purified via flash column chromatography (10% MeOH in $CH_2Cl_2$). To free base in methanol (3 mL) was added 4N HCl in dioxane (0.03 mL). Evaporation of solvent to dryness gave the hydrochloride salt. (Yield 54.5 mg, 55%).

Example 108A

N-Boc-N-ethylpropargylamine

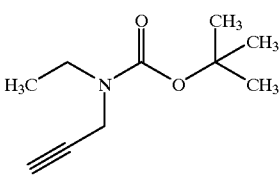

Di-tert-butyl dicarbonate (42.8 g, 196 mmol) in dichloromethane (100 mL) was added dropwise to a solution of propargylamine (11.02 g, 200 mmol) in dichloromethane (200 mL) at room temperature with magnetic stirring. After 2 h, the reaction mixture was washed with aqueous 1N hydrochloric acid (300 mL) and saturated aqueous sodium bicarbonate solution (300 mL). The aqueous layers were washed with dichloromethane (300 mL). The dichloromethane solutions were combined, dried (MgSO₄), filtered and concentrated. The residue was purified by flash chromatography (Biotage 40S, EtOAc-hexanes V/V 1:9 as solvent) to give crude N-Boc-propargylamine. (32.32 g). The crude N-Boc-propargylamine (3.1 g, 20 mmol) was dissolved in dry dimethylformamide (20 mL) with magnetic stirring and cooled in an ice-water bath. Sodium hydride (0.61 g, 24 mmol) was added in small portions. After stirring for 15 min., iodoethane (3.74 g, 24 mmol) was added. The mixture was allowed to warm to room temperature and stirred for 3 h. then diluted with ether and extracted with water and saturated brine. The aqueous layers were back washed with ether and the ether layers were combined, dried (MgSO₄), filtered and concentrated. The residue was purified by flash chromatography (Biotage 40M, ethyl acetate-hexanes as solvent to give N-Boc-N-ethylpropargylamine. (Yield 3.19 g, 87%).

Example 108B (Z)-1,3-Dihydro-4-(3-ethylamino-1-proynyl)-5-fluoro-3-[(3-methoxy-1H-pyrrol-2-yl)methylene]-2H-indol-2-one hydrochloride salt (WWWW)

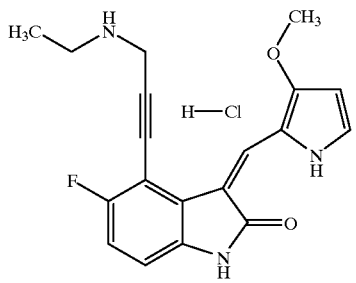

Using Method C above, N-Boc-N-ethylpropargylamine (0.12 g, 0.63 mmol) (Example 108A above) was coupled with (Z)-1,3-dihydro-5-fluoro-4-iodo-3-[(3-methoxy-1H-pyrrol-2-yl)methylene]-2H-indol-2-one (0.1 g, 0.26 mmol) (Starting Material 6) using (Ph₃P)₄Pd (40.0 mg) and CuI (9.0 mg) as catalyst in DMF (5 mL) and Et₃N (5 mL) as solvent at 85° C. for 1 day. To the resulting compound in CH₂Cl₂ (6 mL) was added a 1:1 mixture of trifluoroacetic acid/CH₂Cl₂ (6 mL) and 3 drops of water at 0° C. and the mixture was stirred at 0° C. for 1 h. The mixture was quenched with conc. NH₄OH (6 mL) and diluted with EtOAc. The organic layer was washed with brine and dried with MgSO₄. The product was purified via flash column chromatography (10% MeOH in CH₂Cl₂). To the free base in methanol (2 mL) was added 4N HCl in dioxane (0.04 mL). Evaporation of solvent to dryness gave the hydrochloride salt. (Yield 49 mg, 50%).

Example 109

(S)-(Z)-3-[(4-Acetyl-1H-pyrrol-2-yl)methylene]-1,3-dihydro-5-fluoro-4-[(pyrrolidin-2-yl)ethynyl]-2H-indol-2-one (XXXX)

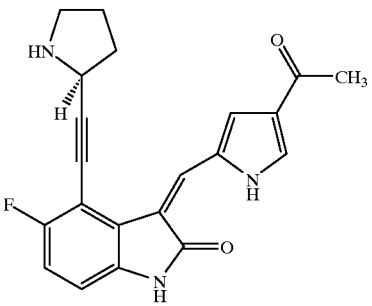

Using Method C above, (S)-N-Boc-2-Ethynyl-pyrrolidine (220 mg, 1.13 mmol) (Example 87B) was coupled with (Z)-3-[(4-acetyl-1H-pyrrol-2-yl)methylene]-1,3-dihydro-5-fluoro-4-iodo-2H-indol-2-one (150 mg, 0.38 mmol) (Example 90B) using (Ph₃P)₄Pd (44 mg, 0.04 mmol) and a catalylic amount of CuI in a mixture of DMF (5 mL) and Et₃N (5 mL) as solvent at 80° C. for 7 hrs. Upon completion, the reaction mixture was diluted with EtOAc and extracted with H₂O. The organic layer was dried over Na₂SO₄, concentrated and the residue was chromatographed on a silica gel column with a 0–5% MeOH in CH₂Cl₂ gradient. The intermediate that resulted from this process was dissolved in 6 mL of a 50% trifluoroacetic acid in CH₂Cl₂ solution that contained 0.3 mL of H₂O at 0° C. and stirred for 2 hrs. Upon completion, the reaction mixture was diluted with EtOAc and extracted with ammonium hydroxide. The organic layer was dried over Na₂SO₄ and concentrated. The (S)-(Z)-3-[(4-Acetyl-1H-pyrrol-2-yl)methylene]-1,3-dihydro-5-fluoro-4-[(pyrrolidin-2-yl)ethynyl]-2H-indol-2-one was obtained after silica gel column with a 0–10% MeOH in CH₂Cl₂ gradient and precipitation out of THF with excess of pentane. (Yield 56 mg, 41%).

Example 110

(S)-(Z)-3-[(4-Acetyl-1H-pyrrol-2-yl)methylene]-1,3-dlhydro-5-fluoro-4-[(pyrrolidin-2-yl)ethynyl]-2H-indol-2-one hydrochloride salt (YYYY)

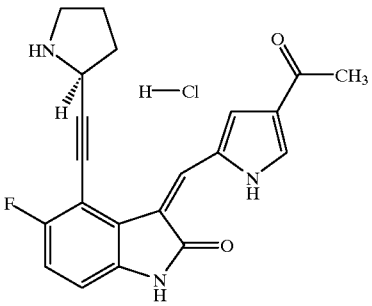

A solution of (S)-(Z)-3-[(4-acetyl-1H-pyrrol-2-yl)methylene]-1,3-dihydro-5-fluoro-4-[(pyrrolidin-2-yl)ethynyl]-2H-indol-2-one (25 mg, 0.07 mmol) (Example 109 above) in dioxane (3 mL) was treated with aqueous HCl under vigorous stirring. (S)-(Z)-3-[(4-Acetyl-1H-pyrrol-2-yl)methylene]-1,3-dihydro-5-fluoro-4-[(pyrrolidin-2-yl)ethynyl]-2H-indol-2-one hydrochloride salt was obtained upon lyophilization of this solution. (Yield 24 mg, 76%).

Example 111

(Z)-3-[(4-Acetyl-1H-pyrrol-2-yl)methylene]-1,3-dihydro-5-fluoro-4-[(2S,4R)-(4-hydroxy-pyrrolidin-2-yl)ethynyl]-2H-indol-2-one (ZZZZ)

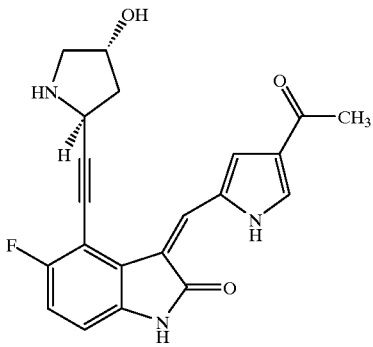

Using Method C above, (3R,5S)-N-Boc-3-Hydroxy-5-ethynyl-pyrrolidine (240 mg, 1.13 mmol) (Example 99C above) was coupled with (Z)-3-[(4-acetyl-1H-pyrrol-2-yl)methylene]-1,3-dihydro-5-fluoro-4-iodo-2H-indol-2-one (150 mg, 0.38 mmol) (Example 90B) using $(Ph_3P)_4Pd$ (43 mg, 0.04 mmol) and a catalyic amount of CuI in a mixture of DMF (5 mL) and $Et_3N$ (5 mL) as solvent at 80° C. for 5 hrs. Upon completion, the reaction mixture was diluted with EtOAc and extracted with $H_2O$. The organic layer was dried over $Na_2SO_4$, concentrated and the residue was chromatographed on a silica gel column with a 0–100% EtOAc in hexanes gradient. The resulting intermediate was dissolved in 6 mL of a 50% trifluoroacetic acid in $CH_2Cl_2$ solution that contained 0.4 mL of $H_2O$ at 0° C. and stirred for 2 hrs. Upon completion, the solution was poured in ammonium hydroxide and extracted with a 5:1 (V/V) mixture of EtOAc and DMF. The organic layer was dried over $Na_2SO_4$ and concentrated. (Z)-3-[(4-Acetyl-1H-pyrrol-2-yl)methylene]-1,3-dihydro-5-fluoro-4-[(2S,4R)-(4-hydroxy-pyrrolidin-2-yl)ethynyl]-2H-indol-2-one was obtained after silica gel column chromatography with a 0–10% MeOH in $CH_2Cl_2$ gradient and trituration with $CH_2Cl_2$. (Yield 50 mg, 35%).

Example 112

(Z)-3-[(4-Acetyl-1H-pyrrol-2-yl)methylene]-1,3-dihydro-5-fluoro-4-[(2S,4R)-(4-hydroxy-pyrrolidin-2-yl)ethynyl]-2H-indol-2-one hydrochloride salt (AAAAA)

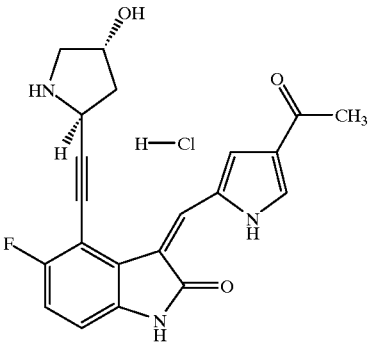

A solution of (Z)-3-[(4-Acetyl-1H-pyrrol-2-yl)methylene]-1,3-dihydro-5-fluoro-4-[(2S,4R)-(4-hydroxy-pyrrolidin-2-yl)ethynyl]-2H-indol-2-one (20 mg, 0.06 mmol) (Example 111 above) in a mixture of DMF/dioxane (2/7 mL respectively) was treated with aqueous HCl under vigorous stirring. (Z)-3-[(4-Acetyl-1H-pyrrol-2-yl)methylene]-1,3-dihydro-5-fluoro-4-[(2S,4R)-(4-hydroxy-pyrrolidin-2-yl)ethynyl]-2H-indol-2-one hydrochloride salt was obtained after lyophilization and treatment with THF and pentane. (Yield 20 mg, 91%).

Example 113

(Z)-3-[(4-Acetyl-1H-pyrrol-2-yl)methylene]-1,3-dihydro-4-[(3-ethylamino)-1-propynyl]-5-fluoro-2H-indol-2-one hydrochloride salt (BBBBB)

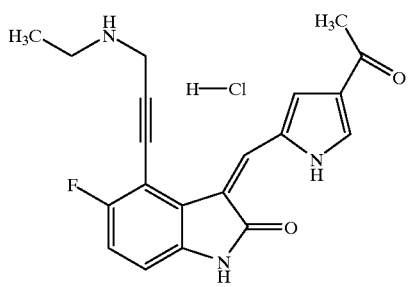

Using Method C above, N-Boc-N-ethylpropargylamine (0.12 g, 0.63 mmol) (Example 108A above) was coupled with (Z)-3-[(4-acetyl-1H-pyrrol-2-yl)methylene]-1,3-dihydro-5-fluoro-4-iodo-2H-indol-2-one (0.1 g, 0.25 mmol) (Example 90B) using $(Ph_3P)_4Pd$ (40.0 mg) and CuI (9.0 mg) as catalyst in DMF (5 mL) and $Et_3N$ (5 mL) as solvent at 85° C. for 12 h. To the resulting compound in $CH_2Cl_2$ (6 mL) was added a 1:1 mixture of trifluoroacetic acid/$CH_2Cl_2$ (6 mL) and 3 drops of water at 0° C. and the mixture was stirred at 0° C. for 1 h. The mixture was quenched with conc. $NH_4OH$ (6 mL) and diluted with EtOAc. The organic layer was washed with brine and dried with $MgSO_4$. The product was purified via flash column chromatography (10% MeOH in CH₂Cl₂). To the free base in methanol (2 mL) was added 4N HCl in dioxane (0.05 mL). Evaporation of solvent to dryness gave the hydrochloride salt. (Yield 41 mg, 42%).

Example 114

(Z)-3-[(4-Acetyl-1H-pyrrol-2-yl)methylene]-1,3-dihydro-5-fluoro-4-[(4-hydroxy-piperldin-4-yl)ethynyl]-2H-indol-2-one hydrochloride salt (CCCCC)

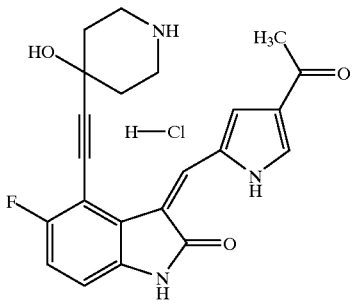

Using Method C above, N-Boc-4-hydroxy-4-ethynyl-piperidine (0.21 g, 0.95 mmol) (Example 101A above) was coupled with (Z)-3-[(4-acetyl-1H-pyrrol-2-yl)methylene]-1,3-dihydro-5-fluoro-4-iodo-2H-indol-2-one (0.15 g, 0.38 mmol) (Example 90B) using (Ph₃P)₄Pd (60 mg) and CuI (13.5 mg) as catalyst in DMF (8 mL) and Et₃N (8 mL) as solvent at 85° C. for 5 h. To the resulting compound in CH₂Cl₂ (6 mL) was added a 1:1 mixture of trifluoroacetic acid/CH₂Cl₂ (6 mL) and 3 drops of water at 0° C. and the mixture was stirred at 0° C. for 3 h. The mixture was then quenched with conc. NH₄OH (6 mL) and diluted with EtOAc. The precipitated product was filtered and washed with methanol. To the free base in methanol (2 mL) was added 4N HCl in dioxane (0.04 mL). Evaporation of solvent to dryness gave the desired hydrochloride salt. (Yield 57 mg, 36%).

Example 115A (S)-N-Boc-2-amino-but-3-yn-1-ol

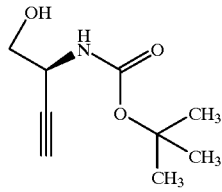

A solution of (S)-N-Boc-2,2-dimethyl-4-ethynyl-oxazolidine (200 mg, 0.89 mmol) (Example 93A above) in a mixture of MeOH (25 mL) and water (2 mL) was treated with p-toluenesulfonic acid monohydrate (16 mg, 0.09 mmol) according to the procedure that described above in Example 104A. (Yield 120 mg, 73%).

Example 115B (S)-N-Boc-2-amino-1-(-tert-butyldimethylsilyloxy)-but-3-yne

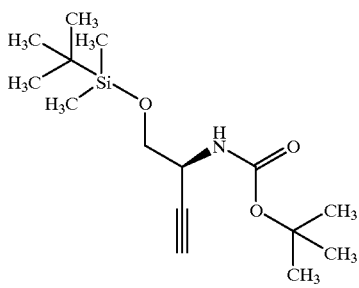

(S)-N-Boc-2-amino-1(-tert-butyldimethylsilyloxy)-but-3-yne was prepared by the treatment of (S)-N-Boc-2-amino-but-3-yn-1-ol (120 mg, 0.65 mmol) (Example 115A above) with imidazole (110 mg, 1.29 mmol) (Aldrich) and tert-butyldimethylsilyl chloride (120 mg, 0.77 mmol) (Fluka) in CH₂Cl₂ (10 mL) according to the procedure described above in Example 104B. (Yield 190 mg, 98%).

Example 115C (S)-2-(N-Boc-N-Methylamino)-1-(-tert-butyldimethylsilyloxy)-but-3-yne

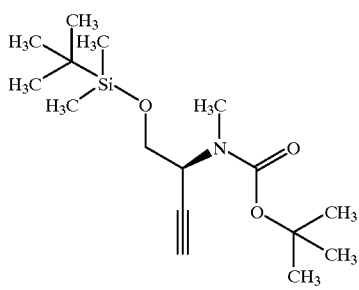

(S)-2-(N-Boc-N-Methylamino)-1-(-tert-butyldimethylsityloxy)-but-3-yne was synthesized according to Method Y above by the treatment of (S)-N-Boc-2-amino-1-(-tert-butyldimethylsilyloxy)-but-3-yne (190 mg, 0.64 mmol) (Example 115B) with NaH (18 mg, 0.76 mmol) and MeI (180 mg, 1.27 mmol) in THF (5 mL). The product was obtained after silica gel column chromatography with a 0–10% EtOAc in hexanes gradient. (Yield 190 mg, 95%).

Example 115D (S)-(Z)-1,3-Dihydro-5-fluoro-4-[3-methylamino-4-hydroxy-1-butynyl]-3-[(3-methoxy-1H-pyrrol-2-yl)methylene]-2H-indol-2-one (DDDDD)

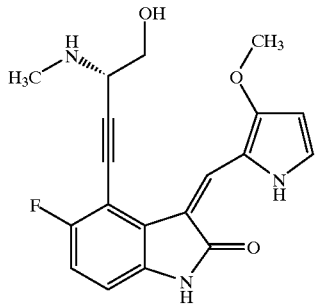

Using Method C above, (S)-2-(N-Boc-N-methylamino)-1-(tert-butyldimethylsilyloxy)-but-3-yne (190 mg, 0.61 mmol) (Example 115C above) was coupled with (Z)-1,3-dihydro-5-fluoro-4-iodo-3-[(3-methoxy-1H-pyrrol-2-yl)methylene]-2H-indol-2-one (80 mg, 0.21 mmol) (Starting Material 6) using $(Ph_3P)_4Pd$ (24 mg, 0.02 mmol) and a catalylic amount of CuI in a mixture of DMF (5 mL) and $Et_3N$ (5 mL) as solvent at 80° C. for 5.5 hrs. Upon completion, the reaction mixture was diluted with EtOAc and extracted with $H_2O$. The organic layer was dried over $Na_2SO_4$, concentrated and the residue was chromatographed on a silica gel column with a 40–100% EtOAc in hexanes gradient. The resulting intermediate was dissolved directly in 6 mL of a 50% trifluoroacetic acid in $CH_2Cl_2$ solution that contained 0.5 mL of $H_2O$ at 0° C. and stirred for 2 hrs. Upon completion, the reaction mixture was diluted with EtOAc and extracted with ammonium hydroxide. The organic layer was dried over $Na_2SO_4$ and concentrated. (S)-(Z)-1,3-Dihydro-5-fluoro-4-[3-methylamino-4-hydroxy-1-butynyl]-3-[(3-methoxy-1H-pyrrol-2-yl)methylene]-2H-indol-2-one was obtained after silica gel column chromatography with a 0–10% MeOH in $CH_2Cl_2$ gradient and precipitation out of THF with excess of pentane. (Yield 32 mg, 42%).

Example 116A

5-Formyl-4-methyl-1H-pyrrole-3-carboxylic acid ethyl ester

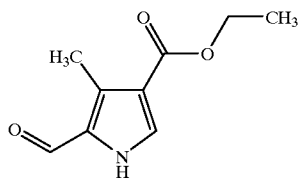

5-Formyl-4-methyl-1H-pyrrole-3-carboxylic acid ethyl ester was prepared according to the procedure of J. B. Paine, III, et al., 5-Unsubstituted 2-Pyrrolecarboxaldehydes for Porphyrin Synthesis and the Cyanovinyl Protecting Group. *J. Org. Chem.* 1988, 53, 2787–2795.

Example 116B (Z)-5-(5-Fluoro-4-iodo-2-oxo-1,2-dihydro-indol-3-ylidenemethyl)-4-methyl-1H-pyrrole-3-carboxylic acid ethyl ester

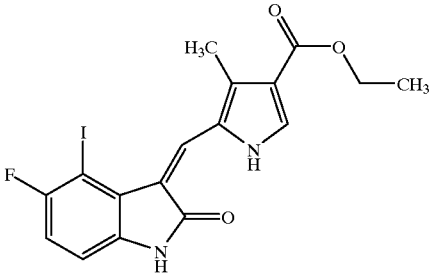

A suspension of 1,3-dihydro-5-fluoro-4-iodo-2H-indol-2-one (0.5 g, 1.8 mmol) (Example 2A) and 5-formyl-4-methyl-1H-pyrrole-3-carboxylic acid ethyl ester (0.39 g, 2.17 mmol) (Example 116A above) in 1% piperidine in 2-propanol (6 mL) was heated at 80° C. for 3 h. The precipitate was collected and washed with water to give (Z)-5-(5-Fluoro-4-iodo-2-oxo-1,2-dihydro-indol-3-ylidenemethyl)-4-methyl-1H-pyrrole-3-carboxylic acid ethyl ester. (Yield 0.67 g, 85%).

Example 116C (Z)-5-[[4-(3-Ethylamino-prop-1-ynyl)-5-fluoro-2-oxo-1,2-dihydro-indol-3-ylidene]methyl]-4-methyl-1H-pyrrole-3-carboxylic acid ethyl ester hydrochloride salt (EEEEE)

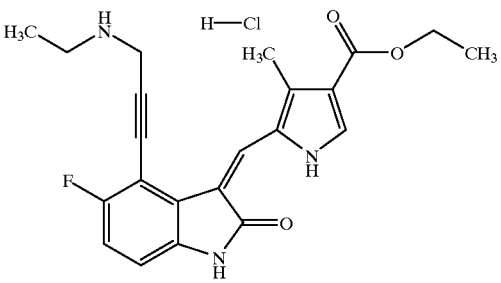

Using Method C above, N-Boc-N-ethylpropargylamine (0.16 g, 0.85 mmol) (Example 108A above) was coupled with 5-(5-fluoro-4-iodo-2-oxo-1,2-dihydro-indol-3-ylidenemethyl)-4-methyl-1H-pyrrole-3-carboxylic acid ethyl ester (Example 116B above) (0.15 g, 0.34 mmol) using $(Ph_3P)_4Pd$ (60.0 mg) and CuI (13.5 mg) as catalyst in DMF (8 mL) and $Et_3N$ (8 mL) as solvent at 81° C. for 6 h. To the resulting compound in $CH_2Cl_2$ (8 mL) was added a 1:1 mixture of trifluoroacetic acid/$CH_2Cl_2$ (8 mL) and 4 drops of water at 0° C. and the mixture was stirred at 0° C. for 1 h. The mixture was quenched with conc. $NH_4OH$ (6 mL) and diluted with EtOAc. The precipitated product was filtered and washed with methanol. To the free base in methanol (3 mL) was added 4N HCl in dioxane (0.03 mL). Evaporation of solvent to dryness yielded the hydrochloride salt. (Yield 50 mg, 33%).

Example 117A (2R,3R)-N-Boc-3-amino-pent-4-yne-2-ol

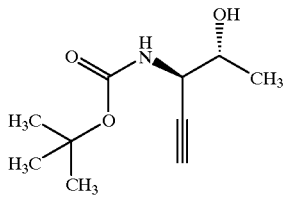

A solution of (4R,5R)-N-boc-4-ethynyl-2,2,5-trimethyl-oxazolidine (1.60 g 6.69 mmol) (Example 102B) and p-toluenesulfonic acid monohydrate (130 mg 0.67 mmol) in MeOH (70 mL) was heated at refluxed. After stirring overnight the solvent was concentrated and the residue was chromatographed directly on a silica gel column with a 0–40% EtOAc in hexanes gradient. This afforded the product (Yield 1.10 g, 83%) as well as recovered starting material (220 mg, 14%).

Example 117B (2R,3R)-N-Boc-3-amino-2-(-tert-butyldimethylsilyloxy)-pent-4-yne

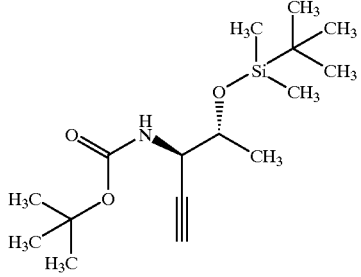

(2R,3R)-N-Boc-3-amino-2-(-tert-butyldimethylsilyloxy)-pent-4-yne was prepared by the treatment of (2R,3R)-N-Boc-3-amino-pent-4-yn-2-ol (1.10 g, 5.02 mmol) (Example 117A above) with imidazole (680 mg, 10.04 mmol) and tert-butyldimethylsilyl chloride (800 mg, 5.52 mmol) in 35 mL of $CH_2Cl_2$. After 24 hrs stirring at room temperature, the mixture was concentrated to a residue which upon silica gel column chromatography with a 0–20% EtOAc in hexanes gradient yielded (2R,3R)-N-Boc-3-amino-2-(-tert-butyldimethylsilyloxy)-pent-4-yne. (Yield 1.30 g, 83%).

Example 117C (2R,3R)-3-(N-Boc-N-methylamino)-2-(-tert-butyldimethylsilyloxy)-pent-4-yne

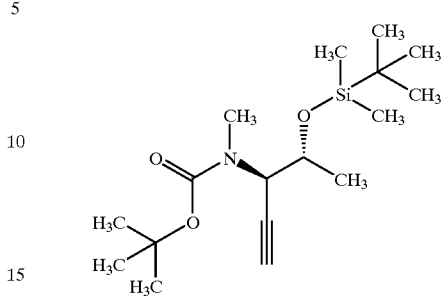

(2R,3R)-3-(N-Boc-N-methylamino)-2-(-tert-butyldimethylsilyloxy)-pent-4-yne was synthesized according to Method Y above by the treatment of (2R,3R)-N-Boc-3-amino-2-(-tert-butyldimethylsilyloxy)-pent-4-yne (400 mg, 1.27 mmol) (Example 117B) with NaH (36 mg, 1.52 mmol) and MeI (360 mg, 2.54 mmol) in THF (30 mL). The product was obtained after silica gel column chromatography with a 0–10% $Et_2O$ in hexanes gradient. (Yield 370 mg, 89%).

Example 117D (Z)-1,3-Dihydro-5-fluoro-4-[(3R,4R)-4-hydroxy-3-methylamino-1-pentynyl]-3-[(3-methoxy-1H-pyrrol-2-yl)methylene]-2H-indol-2-one (FFFFF)

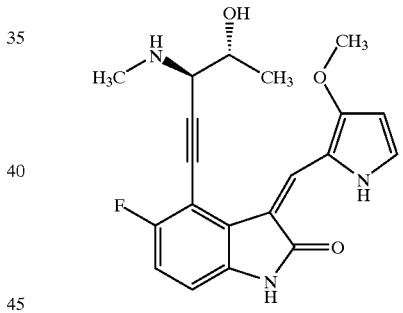

Using Method C above, (2R,3R)-3-(N-Boc-N-methylamino)-2-(tert-butyldimethylsilyloxy)-pent-4-yne (370 mg, 1.13 mmol) (Example 117C above) was coupled with (Z)-1,3-dihydro-5-fluoro-4-iodo-3-[(3-methoxy-1H-pyrrol-2-yl)methylene]-2H-indol-2-one (150 mg, 0.39 mmol) (Starting Material 6) using $(Ph_3P)_4Pd$ (45 mg, 0.04 mmol) and a catalytic amount of CuI in a mixture of DMF (5 mL) and $Et_3N$ (5 mL) as solvent at 80° C. for 5 hrs. Upon completion, the reaction mixture was diluted with EtOAc and extracted with $H_2O$. The organic layer was dried over $Na_2SO_4$, concentrated and the residue was chromatographed on a silica gel column with a 0–40% EtOAc in hexanes gradient. The resulting intermediate was dissolved in 5 mL of a 50% trifluoroacetic acid in $CH_2Cl_2$ solution that contained 0.5 mL of $H_2O$ at 0° C. and stirred for 2 hrs. Upon completion, the reaction mixture was diluted with EtOAc and extracted with ammonium hydroxide. The organic layer was dried over $Na_2SO_4$ and concentrated. (Z)-1,3-Dihydro-5-fluoro-4-[(3R,4R)-4-hydroxy-3-methylamino-1-pentynyl]-3-[(3-methoxy-1H-pyrrol-2-yl)methylene]-2H-

Example 118

(Z)-1,3-Dihydro-5-fluoro-4-[(3R,4R)-4-hydroxy-3-methylamino-1-pentynyl]-3-[(3-methoxy-1H-pyrrol-2-yl)methylene]-2H-indol-2-one hydrochloride salt (GGGGG)

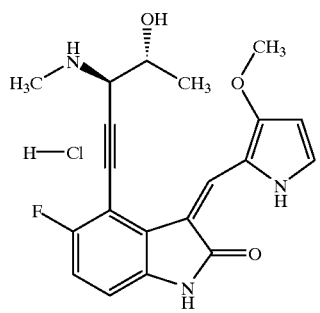

A solution of (Z)-1,3-dihydro-5-fluoro-4-[(3R,4R)-4-hydroxy-3-methylamino-1-pentynyl]-3-[(3-methoxy-1H-pyrrol-2-yl)methylene]-2H-indol-2-one (35 mg, 0.07 mmol) (Example 117C) in dioxane (5 mL) was treated with aqueous HCl under vigorous stirring. (Z)-1,3-Dihydro-5-fluoro-4-[(3R,4R)-4-hydroxy-3-methylamino-1-pentynyl]-3-[(3-methoxy-1H-pyrrol-2-yl)methylene]-2H-indol-2-one hydrochloride salt was obtained upon lyophilization and precipitation out of a (1:3, V/V) mixture of MeOH/CH$_2$Cl$_2$ with excess of hexanes. (Yield 32 mg, 83%).

Example 119A

4-Methyl-N-(prop-2-ynyl)-benzenesulfonamide

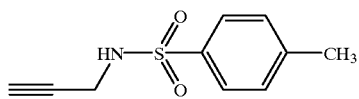

To solution of propargylamine (2.00 g, 36.29 mmol) and Et$_3$N (7.30 g, 72.59 mmol) in CH$_2$Cl$_2$ was added in small portions p-toluenesulfonyl chloride (6.90 g, 36.29 mmol) (J. T. Baker) at 0° C. After 5 min the mixture was filtered and the filtrate was concentrated to a residue that upon direct application on a silica gel column with a 0–40% EtOAc in hexanes gradient yielded 4-Methyl-N-(prop-2-ynyl)-benzenesulfonamide. (Yield 7.30 g, 96%).

Example 119B (Z)-N-[3-[5-Fluoro-3-[(3-methoxy-1H-pyrrol-2-yl)methylene]-2-oxo-2,3-dihydro-1H-indol-4-yl]-prop-2-ynyl]-4-methyl-benzenesulfonamide (HHHHH)

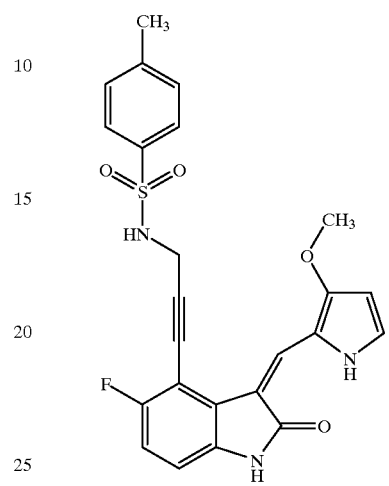

Using Method C above, 4-Methyl-N-(prop-2-ynyl)-benzenesulfonamide (130 mg, 0.62 mmol) (Example 119A above) was coupled with (Z)-1,3-dihydro- 5-fluoro-4-iodo-3-[(3-methoxy-1H-pyrrol-2-yl)methylene]-2H-indol-2-one (80 mg, 0.21 mmol) (Starting Material 6) using (Ph$_3$P)$_4$Pd (24 mg, 0.02 mmol) and a catalytic amount of CuI in a mixture of DMF (5 mL) and Et$_3$N (5 mL) as solvent at 80° C. for 5 hrs. Upon completion, the reaction mixture was diluted with EtOAc and extracted with H$_2$O. The organic layer was dried over Na$_2$SO$_4$ and concentrated. (Z)-N-[3-[5-Fluoro-3-[(3-methoxy-1H-pyrrol-2-yl)methylene]-2-oxo-2,3-dihydro-1H-indol-4-yl]-prop-2-ynyl]-4-methyl-benzenesulfonamide was obtained after HPLC purification with 40% EtOAc in hexanes and precipitation out of THF with excess of hexanes. (Yield 42 mg, 44%).

Example 120A

N-(Prop-2-ynyl)-methanesulfonamide

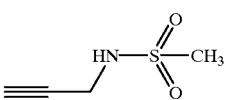

To a solution of propargylamine (2.00 g, 36.29 mmol) and Et$_3$N (7.30 g, 72.59 mmol) in dichloromethane was added dropwise methanesulfonyl chloride (4.10 g, 36.29 mmol) at 0° C. After 5 min the mixture was filtered and the filtrate was concentrated to a residue that upon direct application on a silica gel column with a 0–70% EtOAc in hexanes gradient afforded N-(Prop-2-ynyl)-methanesulfonamide. (Yield 2.00 g, 42%).

Example 120B (Z)-N-[3-[5-Fluoro-3-[(3-methoxy-1H-pyrrol-2-yl)methylene]-2-oxo-2,3-dihydro-1H-indol-4-yl]-prop-2-ynyl]-methanesulfonamide (IIIII)

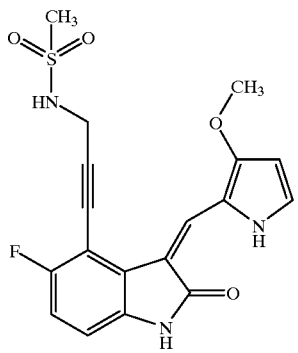

Using Method C above, N-(Prop-2-ynyl)-methanesulfonamide (80 mg, 0.62 mmol) was coupled with (Z)-1,3-dihydro-5-fluoro-4-iodo-3-[(3-methoxy-1H-pyrrol-2-yl)methylene]-2H-indol-2-one (80 mg, 0.21 mmol) (Starting Material 6) using $(Ph_3P)_4Pd$ (24 mg, 0.02 mmol) and a catalytic amount of CuI in a mixture of DMF (5 mL) and $Et_3N$ (5 mL) as solvent at 80° C. for 5 hrs. Upon completion, the reaction mixture was diluted with EtOAc and extracted with $H_2O$. The organic layer was dried over $Na_2SO_4$ and concentrated. (Z)-N-[3-[5-Fluoro-3-[(3-methoxy-1H-pyrrol-2-yl)methylene]-2-oxo-2,3-dihydro-1H-indol-4-yl]-prop-2-ynyl]-methanesulfonamide was obtained after HPLC purification with 40% EtOAc in hexanes and precipitation out of THF with excess of pentane. (Yield 48 mg, 59%).

Example 121

(S)-(Z)-5-[[5-Fluoro-2-oxo-4-[(pyrrolidin-2-yl)ethynyl]-1,2-dihydro-indol-3-ylidene]methyl]-4-methyl-1H-pyrrole-3-carboxylic acid ethyl ester (JJJJJ)

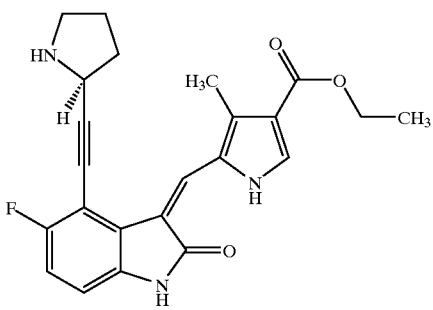

Using Method C above, (S)-N-Boc-2-Ethynyl-pyrrolidine (106 mg, 0.55 mmol) (Example 87B) was coupled with (Z)-5-(5-fluoro-4-iodo-2-oxo-1,2-dihydro-indol-3-ylidenemethyl)-4-methyl-1H-pyrrole-3-carboxylic acid ethyl ester (80 mg, 0.18 mmol) (Example 116B) using $(Ph_3P)_4Pd$ (21 mg, 0.02 mmol) and a catalytic amount of CuI in a mixture of DMF (5 mL) and $Et_3N$ (5 mL) as solvent at 80° C. for 5 hrs. Upon completion, the reaction mixture was diluted with EtOAc and extracted with $H_2O$. The organic layer was dried over $Na_2SO_4$, concentrated and the residue was chromatographed on a silica gel column with a 0–40% EtOAc in hexanes gradient. The resulting intermediate was dissolved in 5 mL of a 50% trifluoroacetic acid in $CH_2Cl_2$ solution that contained 0.5 mL of $H_2O$ at 0° C. and stirred for 2 hrs. Upon completion, the reaction mixture was diluted with EtOAc and extracted with ammonium hydroxide. The organic layer was dried over $Na_2SO_4$ and concentrated. (S)-(Z)-5-[[5-Fluoro-2-oxo-4-[(pyrrolidin-2-yl)ethynyl]-1,2-dihydro-indol-3-ylidene]methyl]-4-methyl-1H-pyrrole-3-carboxylic acid ethyl ester was obtained after silica gel column chromatography with a 0–100% EtOAc in hexanes-30% THF in EtOAc gradient and precipitation out of THF with excess of hexanes. (Yield 21 mg, 28%).

Example 122

(S)-(Z)-5-[[5-Fluoro-2-oxo-4-[(pyrrolidin-2-yl)ethynyl]-1,2-dihydro-indol-3-ylidene]methyl]-4-methyl-1H-pyrrole-3-carboxylic acid ethyl ester hydrochloride salt (KKKKK)

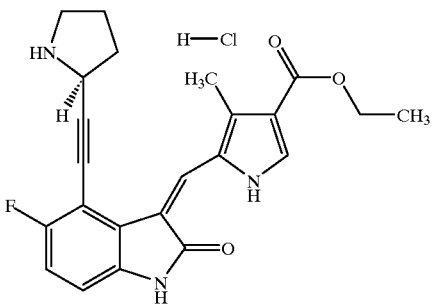

A solution of (S)-(Z)-5-[[5-Fluoro-2-oxo-4-[(pyrrolidin-2-yl)ethynyl]-1,2-dihydro-indol-3-ylidene]methyl]-4-methyl-1H-pyrrole-3-carboxylic acid ethyl ester (14 mg, 0.03 mmol) (from Example 121 above) in dioxane (10 mL) was treated with aqueous HCl under vigorous stirring. (S)-(Z)-5-[[5-Fluoro-2-oxo-4-[(pyrrolidin-2-yl)ethynyl]-1,2-dihydro-indol-3-ylidene]methyl]-4-methyl-1H-pyrrole-3-carboxylic acid ethyl ester hydrochloride salt was obtained upon lyophilization. (Yield 12 mg, 79%).

Example 123A

[2R-Hydroxy-1S-(1R-hydroxy-ethyl)-but-3-ynyl]-carbamic acid tert-butyl ester

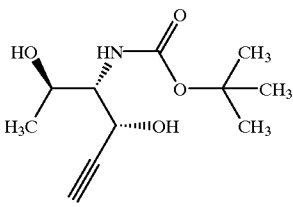

To a solution of 4R-(1R-hydroxy-prop-2-ynyl)-2,2,5R-trimethyl-oxazolidine-3-carboxylic acid tert-butyl ester (1.02 g, 3.79 mmol) (Example 105A above) in MeOH (20 mL) was added $BCl_3$ (1.0 M in $CH_2Cl_2$, 2.6 mL, 2.6 mmol) by injection. The reaction mixture was stirred at r.t. for 2 h. The reaction was quenched by adding AcOEt (150 mL) and washed with $H_2O$, brine, and dried over $Na_2SO_4$. After concentration, [2R-hydroxy-1S-(1R-hydroxy-ethyl)-but-3- ynyl]-carbamic acid tert-butyl ester was obtained as a colorless oil which was used in the next step without further purification. (Yield 0.85 g, 98.1%).

Example 123B (4R-Ethynyl-2,2,6R-trimetyl-[1,3]dioxan-5S-yl)-carbamic acid tert-butyl ester

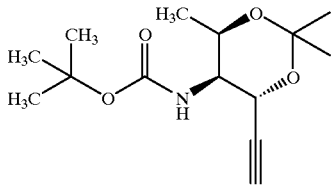

To a solution of [2R-hydroxy-1S-(1R-hydroxy-ethyl)-but-3-ynyl]-carbamic acid tert-butyl ester (0.80 g, 3.5 mmol) (Example 123A above) in a mixture of acetone (20 mL) and 2,2-dimethoxypropane (5 mL) (Aldrich) was added camphor sulfonic acid (50 mg) (Aldrich). The reaction mixture was stirred at r.t. for 2 h. The reaction was quenched by adding AcOEt (150 mL) and washed with $H_2O$, brine, and dried over $Na_2SO_4$. After concentration, the crude product was purified by flash column chromatography (25% AcOEt in hexanes) to give (4R-ethynyl-2,2,6R-trimetyl-[1,3]dioxan-5S-yl)-carbamic acid tert-butyl ester (yield 0.52 g, 55.3%) and 4R-(1S-hydroxy-prop-2-ynyl)-2,2,5R-trimethyl-oxazolidine-3-carboxylic acid tert-butyl ester as colorless oil. (Yield 0.22 g, 23.4%).

Example 123C

Ethyl-(4R,5S,6R-4-ethynyl-2,2,6-trimethyl-[1,3]-dioxan-5-yl)-carbamic acid tert-butyl ester

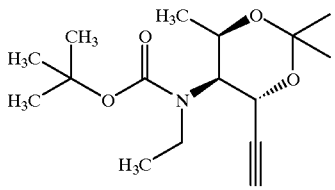

To a solution of (4R-ethynyl-2,2,6R-trimetyl-[1,3]dioxan-5S-yl)-carbamic acid tert-butyl ester (0.50 g, 1.86 mmol) (Example 123C) in DMF (5 mL) was added NaH (95%, 56.3 mg, 2.23 mmol). The reaction mixture was stirred at r.t. for 15 min followed by addition of EtI (0.35 g, 2.23 mmol). After stirring at r.t. for 2 h, the reaction was quenched by sat. $NH_4Cl$. The organic layer was extracted by AcOEt (150 mL) and washed with $H_2O$, brine, and dried over $Na_2SO_4$. After concentration, ethyl-(4R,5S,6R-4-ethynyl-2,2,6-trimethyl-[1,3]-dioxan-5-yl)-carbamic acid tert-butyl ester was obtained as a colorless oil which was used in the next step without further purification. (Yield 0.53 g, 95.9%).

Example 123D (Z)-1,3-Dihydro-4-[(3R,4S,5R)-3,5-dihydroxy-4-ethylamino-1-hexynyl]-5-fluoro-3-[(3-methoxy-1H-pyrrol-2-yl)methylene]-2H-indol-2-one (LLLLL)

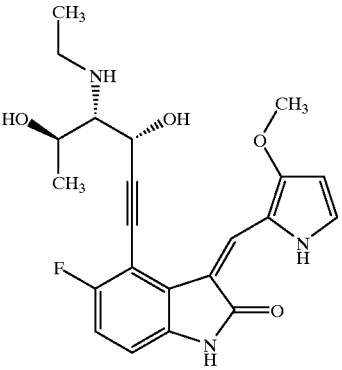

and

Example 123E (R)-(Z)-1,3-Dihydro-4-[(5-ethylamino-6-methyl)-6H-pyran-2-yl]-5-fluoro-3-[(3-methoxy-1H-pyrrol-2-yl)methylene)]-2H-indol-2-one (MMMMM)

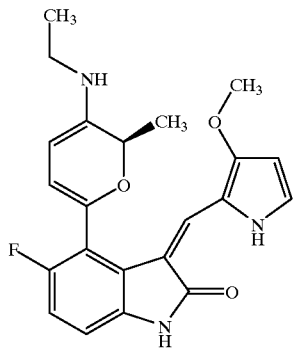

Using Method C above, Ethyl-[(3R,4S,5R)-4-ethynyl-2,2,6-trimethyl-[1,3]-dioxan-5-yl]-carbamic acid tert-butyl ester (148.5 mg, 0.50 mmol) (Example 123C above) was coupled with (Z)-1,3-dihydro-5-fluoro-4-iodo-3-[(3-methoxy-1H-pyrrol-2-yl)methylene]-2H-indol-2-one (96 mg, 0.25 mmol) (Starting Material 6) using $(Ph_3P)_4Pd$ (23.1 mg, 8 mol %) and CuI (5 mg) as catalyst in DMF (5 mL) and $Et_3N$ (5 mL) as solvent at 85° C. for 5 h to give the coupling product (137.2 mg, 99.2% after flash column purification). This coupling product (125 mg) was then treated with 50% of trifluoroacetic acid/$CH_2Cl_2$ (5 mL) and 0.5 mL of water at r.t. for 1 h. The reaction mixture was concentrated to about 2 mL and diluted with AcOEt (50 mL) and then quenched with 2 N NaOH. The organic layer was washed with brine and dried with $Na_2SO_4$. After concentration, the crude product (113.6 mg) was triturated with AcOEt/hexanes and the precipitate was collected by filtration to offer (Z)-1,3-Dihydro-4-[(3R,4S,5R)-3,5-dihydroxy-4-ethylamino-1-hexynyl]-5-fluoro-3-[(3-methoxy-1H-pyrrol-2-yl) methylene]-2H-indol-2-one (LLLLL) as a brown-orange solid. (Yield 29.5 mg, 31.6%). The filtrate was then purified via flash column chromatography (5%–10% MeOH in $CH_2Cl_2$) to give (R)-(Z)-1,3-Dihydro-4-[(5-ethylamino-6-methyl)-6H-pyran-2-yl]-5-fluoro-3-[(3-methoxy-1H-pyrrol-2-yl)methylene)]-2H-indol-2-one (MMMMM). (Yield 33.6 mg, 37.6%).

Example 124A

[2S-Hydroxy-1S-(1R-hydroxy-ethyl)-but-3-ynyl]-carbamic acid tert-butyl ester

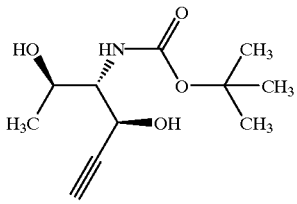

To a solution of 4R-(1S-Hydroxy-prop-2-ynyl)-2,2,5R-trimethyl-oxazolidine-3-carboxylic acid tert-butyl ester (1.40 g, 5.20 mmol) (Example 105A above) in MeOH (30 mL) was added BCl$_3$ (1.0 M in CH$_2$Cl$_2$, 4.6 mL, 4.6 mmol) by injection. The reaction mixture was stirred at r.t. for 1.5 h. The reaction was quenched by adding AcOEt (150 mL) and washed with H$_2$O, brine, and dried over Na$_2$SO$_4$. After concentration, [2S-hydroxy-1S-(1R-hydroxy-ethyl)-but-3-ynyl]-carbamic acid tert-butyl ester was obtained as a colorless oil which was used in the next step without further purification. (Yield 0.90 g, 75.0%).

Example 124B

[2S-(tert-Butyl-dimethyl-silanyloxy)-1S-[1R-(tert-butyl-dimethyl-silanyloxy)-ethyl]-but-3-ynyl]-carbamic acid tert-butyl ester

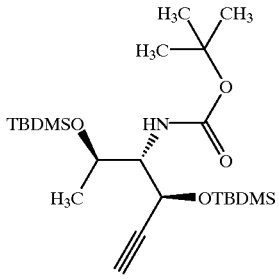

To a solution of [2S-hydroxy-1S-(1R-hydroxy-ethyl)-but-3-ynyl]-carbamic acid tert-butyl ester (0.90 g, 3.9 mmol) (Example 124A above) in DMF (3 mL) were added imidazole (1.6 B, 23.6 mmol) and tert-butyl-dimethyl-silanyl chloride (1.42 g, 9.4 mmol). The reaction mixture was stirred at r.t. for 2 h. The reaction was quenched by adding ice water and extracted by AcOEt (150 mL), washed with H$_2$O, brine, and dried over Na$_2$SO$_4$. After concentration, the crude product was purified by flash column chromatography (2.5% AcOEt in hexanes) to give [2S-(tert-butyl-dimethyl-silanyloxy)-1S-[1R-(tert-butyl-dimethyl-silanyloxy)-ethyl]-but-3-ynyl]-carbamic acid tert-butyl ester as a colorless oil. (Yield 1.34 g, 78.8%).

Example 124C

[2S-(tert-Butyl-dimethyl-silanyloxy)-1S-[1R-(tert-butyl-dimethyl-silanyloxy)-ethyl]-but-3-ynyl]-ethyl-carbamic acid tert-butyl ester

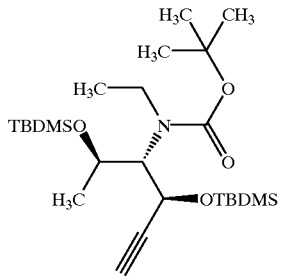

To a solution of [2S-(tert-butyl-dimethyl-silanyloxy)-1S-[1R-(tert-butyl-dimethyl-silanyloxy)-ethyl]-but-3-ynyl]-carbamic acid tert-butyl ester (0.39 g, 0.85 mmol) (Example 124B above) in DMF (3 mL) was added NaH (95%, 32.0 mg, 1.28 mmol). The reaction mixture was stirred at r.t. for 15 min followed by addition of EtI (0.26 g, 1.70 mmol). After stirring at r.t. for 3.5 h, the reaction was quenched by sat. NH$_4$Cl. The organic layer was extracted by AcOEt (150 mL) and washed with H$_2$O, brine, and dried over Na$_2$SO$_4$. After concentration, the crude product was purified by flash column chromatography (2.5% AcOEt in hexanes) to give [2S-(tert-butyl-dimethyl-silanyloxy)-1S-[1R-(tert-butyl-dimethyl-silanyloxy)-ethyl]-but-3-ynyl]-ethyl-carbamic acid tert-butyl ester (0.2 g, 48.5%) as a colorless oil.

Example 124D (Z)-1,3-Dihydro-4-[(3S,4S,5R)-3,5-dihydroxy-4-ethylamino-1-hexynyl]-5-fluoro-3-[(3-methoxy-1H-pyrrol-2-yl)methylene]-2H-indol-2-one (NNNNN)

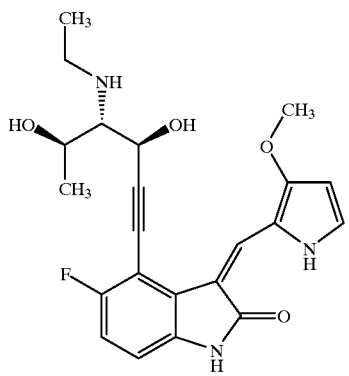

Using Method C above, [2S-(tert-butyl-dimethyl-silanyloxy)-1S-[1R-(tert-butyl-dimethyl-silanyloxy)-ethyl]-but-3-ynyl]-ethyl-carbamic acid tert-butyl ester (200 mg, 0.40 mmol) (Example 124C above) was coupled with (Z)-1,3-dihydro-5-fluoro-4-iodo-3-[(3-methoxy-1H-pyrrol-2-yl)methylene]-2H-indol-2-one (77 mg, 0.20 mmol) (Starting Material 6) using (Ph$_3$P)$_4$Pd (23 mg, 10 mol %) and CuI (3 mg) as catalyst in DMF (5.5 mL) and Et$_3$N (5.5 mL) as solvent at 85° C. for 5 h to give the coupling product (147 mg, 99.3% after flash column purification). This coupling product (146 mg) was then treated with 50% of trifluoroacetic acid/CH$_2$Cl$_2$ (5 mL) at r.t. for 1 h. The reaction mixture was concentrated to about 2 mL and diluted with AcOEt (50 mL) and then quenched with sat. NaHCO₃. The organic layer was washed with brine and dried with Na₂SO₄. After concentration, the crude product (130 mg) was then dissolved in 1.6 mL of THF. To this solution 0.19 mL of 1M tetrabutylammonium fluoride/THF was added and the reaction mixture was stirred at r.t. for 2.5 h. The reaction mixture was diluted with AcOEt, washed with brine and dried with Na₂SO₄. After concentration, the crude product was then purified via flash column chromatography (10% MeOH in CH₂Cl₂) to give (Z)-1,3-Dihydro-4-[(3S,4S,5R)-3,5-dihydroxy-4-ethylamino-1-hexynyl]-5-fluoro-3-[(3-methoxy-1H-pyrrol-2-yl)methylene]-2H-indol-2-one. (Yield 17 mg, 22%)

Example 125A

N-Boc-1-prop-2-ynylamino-propan-2-ol

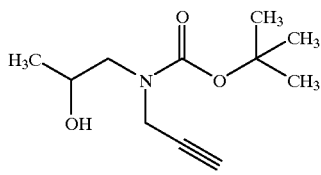

Propylene oxide (4.80 g, 82 mmol) (Aldrich) was added to a solution of propargylamine (9.06 g, 164 mmol) in methanol (30 mL) at room temperature. Mixture was stirred for 16 h then concentrated under reduced pressure. The residue was dissolved in dichloromethane (60 mL). A solution of di-tert-butyl dicarbonate (16.16 g, 74 mmol) in dichloromethane (10 mL) was added dropwise at room temperature with magnetic stirring. After 4 h, the mixture was diluted with ether (200 mL) and extracted with aqueous 1N hydrochloric acid (2×100 mL) and saturated aqueous sodium bicarbonate solution (100 mL). The aqueous layers were washed with ether (200 mL). The organic layers were combined, dried (MgSO₄), filtered, and concentrated. The residue was purified by flash chromatography (Biotage 40M, ethyl acetate-hexanes, 1:3, V/V, as solvent, 25 mL/fraction) to give pure N-Boc-1-prop-2-ynylamino-propan-2-ol. (Yield 5.25 g, 30%).

Example 125B rac-(Z)-1,3-Dihydro-5-fluoro-4-[3-(2-hydroxy-propylamino)-1-propynyl]-3-[(3-methoxy-1H-pyrrol-2-yl)methylene]-2H-indol-2-one hydrochloride salt (OOOOO)

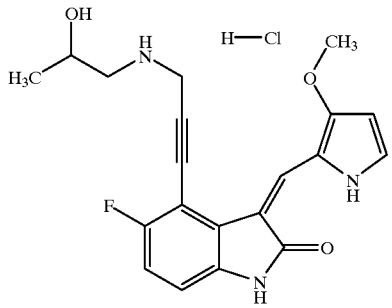

Using Method C above, N-Boc-1-prop-2-ynylamino-propan-2-ol (0.14 g, 0.65 mmol) (Example 125A above) was coupled with (Z)-1,3-dihydro-5-fluoro-4-iodo-3-[(3-methoxy-1H-pyrrol-2-yl)methylene]-2H-indol-2-one (0.1 g, 0.26 mmol) (Starting Material 6) using (Ph₃P)₄Pd (30.0 mg) and CuI (5.0 mg) as catalyst in DMF (5 mL) and Et₃N (5 mL) as solvent at 85° C. for 5 h. To the resulting compound in CH₂Cl₂ (6 mL) was added a 1:1 mixture of trifluoroacetic acid/CH₂Cl₂ (6 mL) and 3 drops of water at 0° C. and the mixture was stirred at 0° C. for 2 h. The mixture was then quenched with conc. NH₄OH (6 mL) and diluted with EtOAc. The organic layer was washed with brine and dried with MgSO₄. The resulting product was purified via flash column chromatography (10% MeOH in CH₂Cl₂). To the free base in methanol (3 mL) was added 4N HCl in dioxane (0.04 mL). Evaporation of solvent to dryness gave rac-(Z)-1,3-Dihydro-5-fluoro-4-[3-(2-hydroxy-propylamino)-1-propynyl]-3-[(3-methoxy-1H-pyrrol-2-yl)methylene]-2H-indol-2-one hydrochloride salt. (Yield 39 mg, 35%).

Example 126 rac-(Z)-3-[(4-Acetyl-1H-pyrrol-2-yl)methylene]-1,3-dihydro-5-fluoro-4-[3-(2-hydroxy-propylamino)-1-propynyl]-2H-indol-2-one hydrochloride salt (PPPPP)

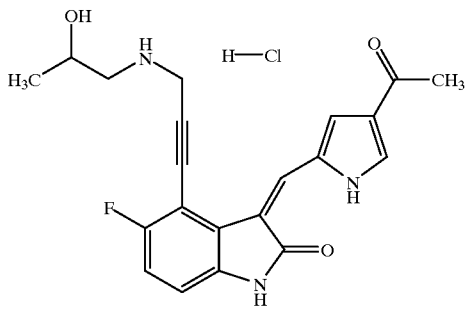

Using Method C above, N-Boc-1-prop-2-ynylamino-propan-2-ol (0.13 g, 0.63 mmol) (Example 125A above) was coupled with (Z)-3-[(4-acetyl-1H-pyrrol-2-yl)methylene]-1,3-dihydro-5-fluoro-4-iodo-2H-indol-2-one (0.1 g, 0.25 mmol) (Example 90B) using (Ph₃P)₄Pd (30.0 mg) and CuI (5.0 mg) as catalyst in DMF (5 mL) and Et₃N (5 mL) as solvent at 85° C. for 5 h. To the resulting compound in CH₂Cl₂ (6 mL) was added a 1:1 mixture of trifluoroacetic acid/CH₂Cl₂ (6 mL) and 3 drops of water at 0° C. and the mixture was stirred at 0° C. for 2 h. The mixture was then quenched with conc. NH₄OH (6 mL) and diluted with EtOAc. The organic layer was washed with brine and dried with MgSO₄. The resulting product was purified via flash column chromatography (10% MeOH in CH₂Cl₂). To the free base in methanol (2 mL) was added 4N HCl in dioxane (0.06 mL). Evaporation of solvent to dryness gave rac-(Z)-3-[(4-Acetyl-1H-pyrrol-2-yl)methylene]-1,3-dihydro-5-fluoro-4-[3-(2-hydroxy-propylamino)-1-propynyl]-2H-indol-2-one hydrochloride salt. (Yield 39 mg, 35%).

Example 127A (Z)-3-[(4-Acetyl-1H-pyrrol-2-yl)methylene]-1,3-dihydro-4-[(3R,4S,5R)-3,5-dihydroxy-4-ethylamino-1-hexynyl]-5-fluoro-2H-indol-2-one (QQQQQ)

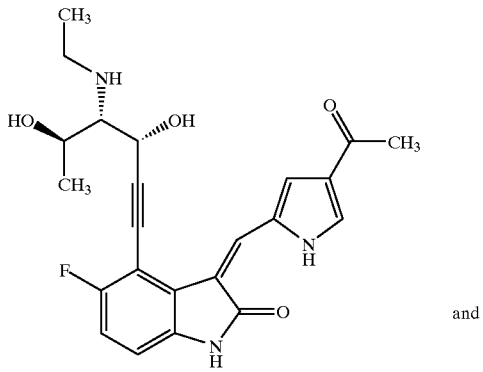

and

Example 127B (R)-(Z)-3-[(4-Acetyl-1H-pyrrol-2-yl)methylene]-1,3-dihydro-4-[(5-ethylamino-6-methyl)-6H-pyran-2-yl]-5-fluoro-2H-indol-2-one (RRRRR)

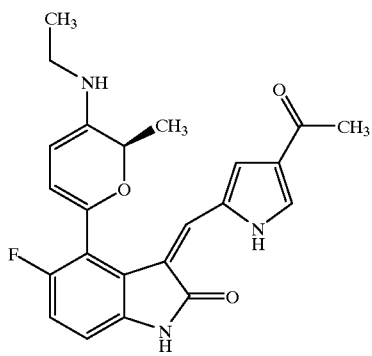

Using Method C above, Ethyl-(4R,5S,6R-4-ethynyl-2,2,6-trimethyl-[1,3]-dioxan-5-yl)-carbamic acid tert-butylester (165 mg, 0.56 mmol) (Example 123C) was coupled with (Z)-3-[(4-acetyl-1H-pyrrol-2-yl)methylene]-1,3-dihydro-5-fluoro-4-iodo-2H-indol-2-one (122 mg, 0.31 mmol) (Example 90B) using (Ph₃P)₄Pd (28.7 mg, 8 mol %) and CuI (5 mg) as catalyst in DMF (6 mL) and Et₃N 15 (6 mL) as solvent at 85° C. for 5 h to give the coupling product (161.2 mg, 92.0% after flash column purification). This coupling product (150 mg) was then treated with 50% of trifluoro-acetic acid/CH₂Cl₂ (5 mL) and 0.5 mL of water at r.t. for 1 h. The reaction mixture was concentrated to about 2 mL and diluted with AcOEt (50 mL) and then quenched with 2 N NaOH. The organic layer was washed with brine and dried with Na₂SO₄. After concentration, the crude product (136.5 mg) was triturated with AcOEt/hexanes and the precipitate was collected by filtration to offer (Z)-3-[(4-Acetyl-1H-pyrrol-2-yl)methylene]-1,3-dihydro-4-[(3R,4S,5R)-3,5-dihydroxy-4-ethylamino-1-hexynyl]-5-fluoro-2H-indol-2-one (QQQQQ) as a brown-orange solid. (Yield 63.0 mg, 55.9%)

The above filtrate was then purified via flash column chromatography (5%–10% MeOH in CH₂Cl₂) to give (R)-(Z)-3-[(4-Acetyl-1H-pyrrol-2-yl)methylene]-1,3-dihydro-4-[(5-ethylamino-6-methyl)-6H-pyran-2-yl]-5-fluoro-2H-indol-2-one (RRRRR). (Yield 36.5 mg, 33.8%).

Example 128

(Z)-3-[(4-Acetyl-1H-pyrrol-2-yl)methylene]-4-[(3R,4S,5R)-4-amino-3,5-dihydroxy-1-hexynyl]-1,3-dihydro-5-fluoro-2H-indol-2-one (SSSSS)

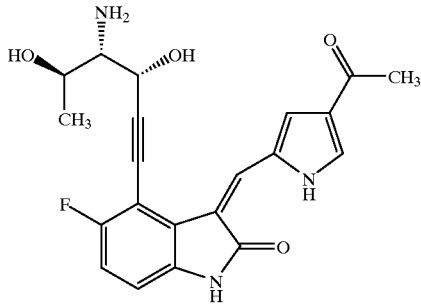

Using Method C above, 4R-(1R-Hydroxy-prop-2-ynyl)-2,2,5R-trimethyl-oxazolidine-3-carboxylic acid tert-butyl ester (151 mg, 0.56 mmol) (Example 105A above) was coupled with (Z)-3-[(4-acetyl-1H-pyrrol-2-yl)methylene]-1,3-dihydro-5-fluoro-4-iodo-2H-indol-2-one (122 mg, 0.31 mmol) (Example 90B) using (Ph₃P)₄Pd (28.7 mg, 8 mol %) and CuI (3 mg) as catalyst in DMF (6 mL) and Et₃N (6 mL) as solvent at 85° C. for 5 h to give the coupling product (108 mg, 65%) after flash column purification. This coupling product (108 mg) was then treated with 50% of trifluoro-acetic acid/CH₂Cl₂ (5 mL) and 0.5 mL of water at r.t. for 1 h. The reaction mixture was concentrated to about 2 mL and diluted with AcOEt (50 mL) and then quenched with 2 N NaOH. The organic layer was washed with brine and dried with Na₂SO₄. After concentration, the crude product was purified with flash column purification (10% MeOH in CH₂Cl₂) to yield (Z)-3-[(4-Acetyl-1H-pyrrol-2-yl)methylene]-4-[(3R,4S,5R)-4-amino-3,5-dihydroxy-1-hexynyl]-1,3-dihydro-5-fluoro-2H-indol-2-one as a yellow solid. (16.0 mg, 20.2%).

Example 129

(Z)-3-[(4-Acetyl-1H-pyrrol-2-yl)methylene]-4-[(3S,4S,5R)-4-amino-3,5-dihydroxy-1-hexynyl]-1,3-dihydro-5-fluoro-2H-indol-2-one (TTTTT)

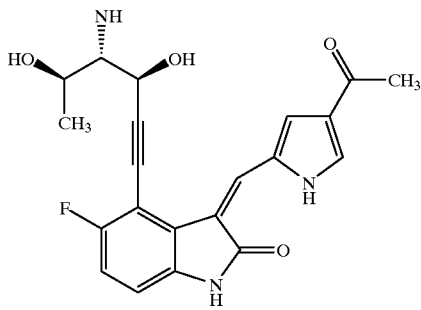

Using Method C above, 4R-(1S-Hydroxy-prop-2-ynyl)-2,2,5R-trimethyl-oxazolidine-3-carboxylic acid tert-butyl ester (151 mg, 0.56 mmol) (Example 105A above) was coupled with (Z)-3-[(4-acetyl-1H-pyrrol-2-yl)methylene]-1,3-dihydro-5-fluoro-4-iodo-2H-indol-2-one (122 mg, 0.31 mmol) (Example 90B) using (Ph₃P)₄Pd (28.7 mg, 8 mol %) and CuI (3 mg) as catalyst in DMF (6 mL) and Et₃N (6 mL) as solvent at 85° C. for 5 h to give the coupling product (136 mg, 80.0%) after flash column purification. This coupling product (135 mg) was then treated with 50% of trifluoroacetic acid/CH₂Cl₂ (5 mL) and 0.5 mL of water at r.t. for 1 h. The reaction mixture was concentrated to about 2 mL and diluted with AcOEt (50 mL) and then quenched with 2 N NaOH. The organic layer was washed with brine and dried with Na₂SO₄. After concentration, the crude product (136.5 mg) was triturated with AcOEt/hexanes and the precipitate was collected by filtration to yield (Z)-3-[(4-Acetyl-1H-pyrrol-2-yl)methylene]-4-[(3S,4S,5R)-4-amino-3,5-dihydroxy-1-hexynyl]-1,3-dihydro-5-fluoro-2H-indol-2-one as a yellow solid. (Yield 88.0 mg, 88.0%).

Example 130

Antiproliferative Activity

The antiproliferative activity of the compounds of the invention is demonstrated below. These effects indicate that the compounds of the present invention are useful in treating cancer, in particular solid tumors such as breast and colon tumors.

CDK2 FlashPlate Assay

To determine inhibition of CDK2 activity, purified recombinant retinoblastoma (Rb) protein was coated on 96 well FlashPlates (New England Nuclear, Boston, Mass.). Rb is a natural substrate for phosphorylation by CDK2 (Herwig and Strauss *Eurr. J. Biochem.*, Vol. 246 (1997) pp. 581–601 and references therein). Recombinant active human Cyclin E/CDK2 complexes were partially purified from extracts of insect cells. The active Cyclin E/CDK2 was added to the Rb-coated FlashPLates along with $^{33}$P-ATP and dilutions of test compounds. Plates were incubated for 25 minutes at room temperature with shaking, then washed and counted in the Topcount scintillation counter (Packard Instrument Co., Downers Grove, Ill.). Dilutions of test compounds were tested in duplicate in each assay. The percent inhibition of Rb phosphorylation, which is a measure of the inhibition of CDK2 activity, was determined according to the following formula:

$$100 \times \left[1 - \frac{\text{test compound} - \text{nonspecific}}{\text{total} - \text{nonspecific } s}\right]$$

where "test compound" refers to the average counts per minute of the test duplicates, "nonspecific" refers to the average counts per minute when no Cyclin E/CDK2 was added, and "total" refers to the average counts per minute when no compound was added.

The results of the foregoing in vitro experiments are set forth in Tables I A and I B below.

Each of the compounds in Table I A had IC$_{50}$ less than 4.0 µM.

TABLE 1A

| Compound | CDK2 IC$_{50}$ (µM) |
|---|---|
| A | <4.0 |
| B | <4.0 |
| C | <4.0 |

TABLE 1A-continued

| Compound | CDK2 IC$_{50}$ (µM) |
|---|---|
| D | <4.0 |
| E | <4.0 |
| F | <4.0 |
| G | <4.0 |
| H | <4.0 |
| I | <4.0 |
| J | <4.0 |
| K | <4.0 |
| L | <4.0 |
| M | <4.0 |
| N | <4.0 |
| O | <4.0 |
| Q | <4.0 |
| R | <4.0 |
| Example 21 | <4.0 |
| U | <4.0 |
| V | <4.0 |
| W | <4.0 |
| X | <4.0 |
| Y | <4.0 |
| AA | <4.0 |
| BB | <4.0 |
| DD | <4.0 |
| FF | <4.0 |
| HH | <4.0 |
| II | <4.0 |
| JJ | <4.0 |
| KK | <4.0 |
| LL | <4.0 |
| MM | <4.0 |
| NN | <4.0 |
| OO | <4.0 |
| PP | <4.0 |
| QQ | <4.0 |
| RR | <4.0 |
| TT | <4.0 |
| UU | <4.0 |
| VV | <4.0 |
| WW | <4.0 |
| XX | <4.0 |
| ZZ | <4.0 |
| AAA | <4.0 |
| BBB | <4.0 |

TABLE 1B

| Compound | % Inhibition | CDK2 Concentration (µM) |
|---|---|---|
| Z | >90 | ⊠1.0 |
| EE | >60 | ⊠1.0 |
| YY | >90 | ⊠1.0 |

Cell-Based Assays

The estrogen receptor negative epithelial breast carcinoma line (MDA-MB-435) was purchased from American Type Cell Culture Collection (ATCC; Rockville, Md.) and was grown in the medium recommended by ATCC. For analysis of the effect of the test compounds on growth of these cells, the cells were plated at 2000 cells per well in a 96-well tissue culture plate, and were incubated overnight at 37° C. with 5% CO₂. The next day, the test compounds were dissolved in 100% dimethyl sulfoxide (DMSO) to yield a 10 mM stock solution. Each compound was diluted with sterile medium to 1 mM in a sufficient quantity to yield a final concentration of 120 ▼M. The compounds were then serially diluted in medium with 1.2% DMSO. One-fourth final volume of the diluted compounds was transferred to 96 well plates. Test compounds were assayed in duplicate. DMSO was added to a row of "control cells" such that the final concentration of DMSO in each well was 0.3%. Wells to which no cells were added served as the "blank." Wells to which no inhibitor was added served as "no inhibitor control". The plates were returned to the incubator, and 5 days post addition of test compound, were analyzed as described below.

3-(4,5-Dimethylthiazole-2-yl)-2,5-diphenyl-2H-tetrazolium bromide (thiazolyl blue; MTT) was added to each well to yield a final concentration of 1 mg/mL. The plates were then incubated at 37° C. for 3 hours. The plates were centrifuged at 1000 rpm for 5 minutes prior to aspiration of the MTT-containing medium. The MTT-containing medium was then removed and 100 µL 100% ethanol was added to each well to dissolve the resulting formazan metabolite. To ensure complete dissolution, plates were shaken for 15 minutes at room temperature. Absorbencies were read in a microtiter plate reader (Molecular Dynamics) at a wavelength of 570 nm with a 650 nm reference. Percent inhibition was calculated by subtracting the absorbance of the blank (no cell) wells from all wells, then subtracting the division of the average absorbance of each test duplicate by the average of the controls from 1.00. Inhibitory concentrations ($IC_{50}$) were determined from the linear regression of a plot of the logarithm of the concentration versus the percent inhibition.

The colon carcinoma line SW480 also was obtained from the ATCC and was tested according to the same protocol provided above with the following modification: cell line SW480 was plated at 1000 cells per well and analyzed at 4 days post addition of test compound.

The results of the foregoing in Vitro tests are set forth below in Tables II and III.

TABLE II

Antiproliferative Activity In Cell Line MDA-MB435*

| Compound | MDA-MB435 $IC_{50}$ (µM) |
|---|---|
| OO | <3.5 |
| PP | <3.5 |
| QQ | <3.5 |
| RR | <3.5 |
| TT | <3.5 |
| UU | <3.5 |
| VV | <3.5 |
| WW | <3.5 |
| XX | <3.5 |
| YY | <3.5 |
| AAA | <3.5 |
| BBB | <3.5 |

*Most of the data reflect the results of one experiment. In those cases where an experiment was repeated, the above data is an average of the results of the separate experiments.

TABLE III

Antiproliferative Activity In Cell Line SW480

| Compound | SW480 $IC_{50}$ (µM) |
|---|---|
| OO | <1.0 |
| PP | <1.0 |
| RR | <1.0 |
| CCC | <1.0 |

Example 131

Tablet Formulation

| Item | Ingredients | Mg/Tablet | | | | | |
|---|---|---|---|---|---|---|---|
| 1 | Compound 1* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound 1 represents a compound of the invention.

Manufacturing Procedure:

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 132

Capsule Formulation

| Item | Ingredients | mg/Capsule | | | | |
|---|---|---|---|---|---|---|
| 1 | Compound 1* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound 1 represents a compound of the invention.

Manufacturing Procedure:

1. Mix Items 1, 2 and 3 in a suitable mixer for 15 minutes.
2. Add Items 4 & 5 and mix for 3 minutes.
3. Fill into a suitable capsule.

Example 133

Injection Solution/Emulsion Preparation

| Item | Ingredient | mg/mL |
|---|---|---|
| 1 | Compound 1* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound 1 represents a compound of the invention.

Manufacturing Procedure:

1. Dissolve item 1 in item 2.
2. Add items 3, 4 and 5 to item 6 and mix until dispersed, then homogenize.

Example 134

Injection Solution/Emulsion Preparation

| Item | Ingredient | mg/mL |
|---|---|---|
| 1 | Compound 1* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound 1 represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. The compound 1,3-dihydro-5-fluoro-4-iodo-2H-indol-2-one.

2. The compound 1,3-dihydro-4-iodo-5-nitro-2H-indol-2-one.

3. The compound 4-bromo-1,3-dihydro-5-nitro-2H-indol-2-one.

* * * * *

UNITED STATES PATENT AND TRADEMARK OFFICE
CERTIFICATE OF CORRECTION

PATENT NO.     : 6,303,793 B1
DATED          : October 16, 2001
INVENTOR(S)    : Yi Chen and Kin-Chun Luk It is certified that error appears in the above-identified patent and that said Letters Patent is hereby corrected as shown below:

<u>Title page,</u>
Item [75], the Inventors read: "Yi Chen, Nutley; Apostolos Dermatakis, North Brunswick; Jin-Jun Liu, Warren; Kin-Chun Luk, North Caldwell, all of NJ (US)". The Inventors should read as follows: -- Yi Chen, Nutley; Kin-Chun Luk, North Caldwell, both of NJ (US) --.

Signed and Sealed this

Sixth Day of August, 2002

Attest:

Attesting Officer

JAMES E. ROGAN
*Director of the United States Patent and Trademark Office*